US011311511B2

(12) United States Patent
Mahdavi et al.

(10) Patent No.: US 11,311,511 B2
(45) Date of Patent: Apr. 26, 2022

(54) BIOFILM INHIBITING COMPOSITIONS ENHANCING WEIGHT GAIN IN LIVESTOCK

(71) Applicant: Akeso Biomedical, Inc., Cambridge, MA (US)

(72) Inventors: Jafar Mahdavi, Lund (SE); Dlawer Ala'Aldeen, Watford (GB); Panos Soultanas, Nottingham (GB)

(73) Assignee: AKESO BIOMEDICAL, INC., Waltham, MA (US)

( * ) Notice: Subject to any disclaimer, the term of this patent is extended or adjusted under 35 U.S.C. 154(b) by 0 days.

(21) Appl. No.: 16/877,190

(22) Filed: May 18, 2020

(65) Prior Publication Data

US 2020/0316008 A1 Oct. 8, 2020

Related U.S. Application Data

(60) Division of application No. 15/860,989, filed on Jan. 3, 2018, now Pat. No. 10,653,658, which is a continuation-in-part of application No. 15/234,941, filed on Aug. 11, 2016, now Pat. No. 10,555,531, which is a continuation-in-part of application No. PCT/US2015/044603, filed on Aug. 11, 2015.

(60) Provisional application No. 62/334,746, filed on May 11, 2016, provisional application No. 62/296,386, filed on Feb. 17, 2016.

(51) Int. Cl.

| | |
|---|---|
| *A61K 31/295* | (2006.01) |
| *A01N 55/02* | (2006.01) |
| *A61P 31/04* | (2006.01) |
| *A23K 20/10* | (2016.01) |
| *A23K 50/30* | (2016.01) |
| *A23K 50/75* | (2016.01) |
| *A23K 50/10* | (2016.01) |
| *A01N 59/16* | (2006.01) |
| *A23K 20/20* | (2016.01) |
| *A01N 37/44* | (2006.01) |
| *A01N 37/10* | (2006.01) |
| *A61K 35/12* | (2015.01) |
| *A01N 43/40* | (2006.01) |
| *A61K 35/37* | (2015.01) |
| *A01N 37/36* | (2006.01) |
| *A61K 35/36* | (2015.01) |
| *C09D 5/14* | (2006.01) |
| *A61L 2/16* | (2006.01) |

(52) U.S. Cl.
CPC ............ *A61K 31/295* (2013.01); *A01N 37/10* (2013.01); *A01N 37/36* (2013.01); *A01N 37/44* (2013.01); *A01N 43/40* (2013.01); *A01N 55/02* (2013.01); *A01N 59/16* (2013.01); *A23K 20/10* (2016.05); *A23K 20/30* (2016.05); *A23K 50/10* (2016.05); *A23K 50/30* (2016.05); *A23K 50/75* (2016.05); *A61K 35/12* (2013.01); *A61K 35/36* (2013.01); *A61K 35/37* (2013.01); *A61L 2/16* (2013.01); *A61P 31/04* (2018.01); *C09D 5/14* (2013.01)

(58) Field of Classification Search
None
See application file for complete search history.

(56) References Cited

U.S. PATENT DOCUMENTS

| | | | |
|---|---|---|---|
| 2,946,722 | A | 7/1960 | Hoffman |
| 3,259,500 | A | 7/1966 | Barnhart |
| 3,491,187 | A | 1/1970 | Ely |
| 3,558,778 | A | 1/1971 | Klingbail |
| 4,053,592 | A | 10/1977 | Smith |
| 4,171,379 | A | 10/1979 | Dickerson |
| 4,504,471 | A | 3/1985 | Takagi |
| 5,879,697 | A | 3/1999 | Ding |
| 6,024,979 | A | 2/2000 | Danielson |
| 6,139,879 | A | 10/2000 | Taylor |
| 6,773,737 | B1 | 8/2004 | Roselle |
| 7,247,338 | B2 | 7/2007 | Pui |
| 7,431,939 | B1 | 10/2008 | Buddington |
| 8,028,646 | B2 | 10/2011 | Pui |

(Continued)

FOREIGN PATENT DOCUMENTS

| | | |
|---|---|---|
| CA | 710277 | 5/1965 |
| CN | 1069192 | 2/1993 |

(Continued)

OTHER PUBLICATIONS

Akiyama, et al., "Adherence characteristics and susceptibility to antimicrobial agents of *Staphylococcus aureus* strains isolated from skin infections and atopic dermatitis," J Dermatol Sci., 23(3):155-60 (2000).

(Continued)

*Primary Examiner* — Joseph R Kosack
(74) *Attorney, Agent, or Firm* — Pabst Patent Group LLP

(57) ABSTRACT

A method of enhancing the growth of an animal, as well as treating or preventing antimicrobial infections is provided. The method includes causing the animal to ingest or absorb an effective amount of one or more Fe III complex compounds, including but not limited to Fe III complexes comprising ligands bound to the iron center such as amino acids or α-hydroxy acids. The compounds are also useful for inhibiting, reducing, or preventing biofilm formation or buildup on a surface; the treatment of, inhibition of growth of, and inhibition of colonization by, bacteria, both in biological and non-biological environments; disinfecting surfaces, potentiating the effects of antibiotics and other anti-microbial agents, and increasing the sensitivity of bacteria and other microorganisms, to anti-microbial agents are also provided.

12 Claims, 8 Drawing Sheets

(56) References Cited

U.S. PATENT DOCUMENTS

| | | |
|---|---|---|
| 8,178,709 B2 | 5/2012 | Nelson |
| 9,655,912 B2 | 5/2017 | Mahdavi |
| 9,961,886 B2 | 5/2018 | Dlawer |
| 9,975,914 B2 | 5/2018 | Dlawer |
| 10,106,567 B2 | 10/2018 | Dlawer |
| 2002/0192202 A1 | 12/2002 | Naidu |
| 2003/0054090 A1 | 3/2003 | Hansen |
| 2004/0265427 A1 | 12/2004 | Boren |
| 2005/0123620 A1 | 6/2005 | Chiou |
| 2005/0193955 A1 | 9/2005 | Robbins |
| 2006/0057252 A1 | 3/2006 | Morimoto |
| 2006/0134227 A1 | 6/2006 | Bortz |
| 2006/0204554 A1 | 9/2006 | Cecava |
| 2007/0249553 A1 | 10/2007 | Newell |
| 2007/0269495 A1 | 11/2007 | Ashmead |
| 2008/0194679 A1 | 8/2008 | Ashmead |
| 2009/0035385 A1 | 2/2009 | Bortz |
| 2009/0074925 A1 | 3/2009 | Miasnikov |
| 2009/0182044 A1 | 7/2009 | Ashmed |
| 2010/0137193 A1 | 6/2010 | Baker |
| 2010/0137198 A1 | 6/2010 | Eini |
| 2010/0178361 A1 | 7/2010 | Ueda |
| 2010/0249058 A1 | 9/2010 | Ito |
| 2012/0077884 A1 | 3/2012 | Mochizuki |
| 2012/0276280 A1 | 11/2012 | Doshi |
| 2012/0288531 A1 | 11/2012 | Tuvia |
| 2012/0315372 A1 | 12/2012 | Stark |
| 2013/0022706 A1 | 1/2013 | Bamford |
| 2013/0189374 A1 | 7/2013 | Bortz |
| 2013/0231302 A1 | 9/2013 | Raad |
| 2014/0057987 A1 | 2/2014 | Vinson |
| 2014/0134290 A1 | 5/2014 | Bamford |
| 2014/0364491 A1 | 12/2014 | Bortz |
| 2017/0042848 A1 | 2/2017 | Ala'Aldeen |
| 2017/0231302 A1 | 8/2017 | Rhodes |
| 2017/0231945 A1 | 8/2017 | Mahdavi |
| 2018/0094011 A1 | 4/2018 | Ala'Aldeen |
| 2018/0125808 A1 | 5/2018 | Ala'Aldeen |
| 2018/0139932 A1 | 5/2018 | Ala'Aldeen |
| 2018/0199550 A1 | 7/2018 | Ala'Aldeen |
| 2018/0258120 A1 | 9/2018 | Ala'Aldeen |
| 2018/0299550 A1 | 10/2018 | Pierce |

FOREIGN PATENT DOCUMENTS

| | | |
|---|---|---|
| EP | 2253681 | 11/2010 |
| EP | 2286666 | 2/2011 |
| EP | 3179870 | 6/2017 |
| JP | 2006321776 | 11/2006 |
| RU | 2156080 | 9/2000 |
| WO | 9117044 | 11/1991 |
| WO | 9606101 | 2/1996 |
| WO | 9809652 | 3/1998 |
| WO | 01028338 | 4/2001 |
| WO | 03040351 | 5/2003 |
| WO | 2005055944 | 6/2005 |
| WO | 2006046017 | 5/2006 |
| WO | 2006099153 | 9/2006 |
| WO | 2008105983 | 9/2008 |
| WO | 2012167368 | 12/2012 |
| WO | 2012168891 | 12/2012 |
| WO | 2013121214 | 8/2013 |
| WO | 2016025448 | 2/2016 |
| WO | 2017027742 | 2/2017 |
| WO | 2017165287 | 9/2017 |

OTHER PUBLICATIONS

Akiyama, et al., "Assessment of *Streptococcus pyogenes* microcolony formation in infected skin by confocal laser scanning microscopy," J Dermatol Sci., 32(3):193-9 (2003b).

Akiyama, et al., "Confocal laser scanning microscopic observation of glycocalyx production by *Staphylococcus aureus* in skin lesions of bullous impetigo, atopic dermatitis and pemphigus foliaceus," Br J Dermatol., 148(3):526-32 (2003).

Atta, et al., "Synthesis and spectroscopic investigations of iron oxide nano-particles for biomedical applications in the treatment of cancer cells", J Mol Structure, 1086:24654 (2015).

Banin, et al., "Iron and pseudomonas aeruginosa biofilm formation," PNAS, 102:11076-81 (2005).

Barco, et al., "D-(−)-Quinic acid: a Chiron store for natural product synthesis," Tetrahedron Asymmetry, 8(21):3515-45 (1997).

Bek-Thomson, et al., "Acne is not associated with yet-uncultured bacteria," J. Clin. Microbiol., 46(10):3355-60 (2008).

Bovell-Benjamin, et al., "Iron absorption from ferrous bisglycinate and ferric trisglycinate in whole maize is regulated by iron status", Am J Clin Nutr, 71:1563-1569 (2000).

Bremner, et al., "Iron metabolism in the veal calf", British Journal of Nutrition, 29(1):229-243 (1973).

Buchanan, "Beta-barrel proteins from bacterial outer membranes: structure, function and refolding," Curr. Opin. Struc. Biol., 9(40):455-61 (1999).

Burkhart, et al., "Dermatophytoma: Recalcitrance to treatment because of existence of fungal biofilm," J Am Acad Dermatol., 47(4):629-31 (2002).

Campbell and Hasinoff, "Ferrous sulfate reduces levodopa bioavailability: Chelation as a possible mechanism," Clin. Pharmacol. Ther., 45:220-5 (1989).

Carroll, et al., "Ferric Citrate as an Ingredient of Mineral Mixtures in paired-feeding experiments with growing swine", Journal of Agricultural Research, 40(10):921-926 (1930).

Cervantes, et al., "α1-2 Fucosylated Chains (H-2, H-1, and Lewisb) are the Main Human Milk Receptor Analogs for Campylobacter", Campylobacters, Helicobacters, and Related Organisms, pp. 653-658, Springer Science US (1996).

Creek, et al., "Stable isotope-assisted metabolomics for network-wide metabolic pathway elucidation," Analytical Chem., 84:8442-7 (2012).

Dasti, et al., "Campylobacter jejuni: a brief overview on pathogenicity-associated factors and disease-mediating mechanisms", Int J Med Microbiol.,300:205-211 (2010).

Fritz, et al., "Biological availability in animals of iron from common dietary sources", J Arig Food Chem., 18:647-51 (1970).

Golden, et al., "Identification of Motility and Autoagglutination Campylobacter jejuni Mutants by Random Transposon Mutagenesis," Infect Immun., 70(4):1761-71 (2002).

Gustafson, et al., "Antibiotic use in animal agriculture", J Appl Microbiol., 83:531-41 (1997).

Hedin, "*Staphylococcus epidermidis*—hospital epidemiology and the detection of methicillin resistance," Scand J Infect Dis Suppl., 90:1-59 (1993).

Hoiby, et al., "Antibiotic resistance of bacterial biofilms," Int J Antimicrob Agents, 35(4):322-32 (2010).

Humphrey, et al., "Campylobacter jejuni in dairy cows and raw milk," Epidemiol Infect., 98:263-9 (1987).

Humphrey, et al., "Isolation of Campylobacter species from non-clinical samples," Public Health Lab Serv Microbiol Digest., 13:86-8 (1996).

Humphrey, et al., "Techniques for the optimum recovery of cold injured Campylobacter jejuni from milk or water," J Appl Bacteriol. 61:125-32. (1986).

Huyer, et al., "Outer membrane porin protein of Campylobacter jejuni," FEMS Microbiol. Lett., 37(3):247-50 (1986).

Iime, Glossary of Medical education terms, http://www.iime.oeg/glossaey.htm, pp. 1-39 retrieved from the interner Mar. 24, 2011.

Ikezawa, et al., "A Role of *Staphyococcus aureus*, Interleukin-18, Nerve Growth Factor and Semaphorin 3A, an Axon Guidance Molecule, in Pathogenesis and Treatment of Atopic Dermatitis," Allergy Asthma Immunol Res., 2(4):235-46 (2010).

International Search Report for corresponding PCT/US2016/046623 dated Sep. 26, 2016.

Jacobs-Reitsma, et al., "Epidemiology of *Campylobacter* spp. at two Dutch broiler farms," Epidemiol Infect., 114:413-21 (1995).

James, et al., "Biofilms in chronic wounds," Wound Repair Regen., 16(1):37-44 (2008).

(56) References Cited

OTHER PUBLICATIONS

Jenkins, et al., "Effects of Excess Iron in Milk Replacer on Calf Performance", J. Dairy Sci., 70:2349-2354 (1987).
Kazwala, et al., "Factors responsible for the introduction and spread of Campylobacter jejuni infection in commercial poultry production," Vet Rec. 1990;126:305-6. (1990).
Kim, et al., Acidifier as an Alternative Material to Antibiotics in Animal Feed, Asian-Australasian Journal of Animal Sciences, 18(7):1048-1060 (2005).
Lai, "205874Orig1s000", Clinical pharmacology and biopharmaceutics reviews of zerenex (ferric ciltrate),pp. 1-95, XP055391980, https://www.accessdata.fda.gov/drugdatfda_does/nda/2014/205874Orig1s000ClinPharm R,pdf, (2014).
Lee, et al., "Chitin Regulation of Immune Responses: An Old Molecule With New Roles," Curr Opin Immunol., 20(6):684-9 (2008).
Leung, et al., "Atopic dermatitis," Lancet, 361(9352):151-60 (2003).
Ley, et al., "Human gut microbes associated with obesity," Nature, 444 (7122):1022-3 (2006).
Ley, et al., "Obesity alters gut microbial ecology," PNAS, 102(31):11070-5 (2005).
Lindblom, et al., "Natural Campylobacter colonization in chickens raised under different environmental conditions," J Hyg., 96:385-91 (1986).
Liu, et al., "Clinical practice guidelines by the infectious diseases society of america for the treatment of methicillin-resistant *Staphylococcus aureus* infections in adults and children," Clin Infect Dis., 52(3):e18-55 (2011).
Mahdavi, et al., "A novel O-linked glycan modulates Campylobacter jejuni major outer membrane protein-mediated adhesion to human histo-blood group antigens and chicken colonization," Open Biol., 4:130202. doi: 10.1098/rsob.130202 (2014).
Mahdavi, et al., "Helicobacter pylori SabA adhesin in persistent infection and chronic inflammation," Science, 297:573-8 (2002).
Meinersmann, et al., "Concerted evolution of duplicate fla genes in Campylobacter," Microbiology, 146(9):2283 (2000).
Menelaou, et al., "Synthesis and characterization of two new isostructural ion(III)-quinates from aqueous solutions," J Agrolimentary Processes Tech., XII:281-4 (2006).
Menelauo, et al., "pH-Specific Synthetic Chemistry and Solution Studies in the Binary System of Iron(III) with the r-Hydroxycarboxylate Substrate Quinic Acid:Potential Relevance to Iron Chemistry in Plant Fluids", Inorg Chem., 48:1844-56 (2009).
Miles and Maskell, "The antagonism of tetracycline and ferric iron in vivo", J Med Microbiol., 20:17-26 (1985).
Miller, et al., "Pumping iron: mechanisms for iron update by Campylobacter," Microbiology, 155:3157-65 (2009).
Misawa, et al., "Isolation of Campylobacter species from zoo animals and polymerase chain reaction-based randomamplified polymorphism DNA analysis", Vet Microbiol., 71:59-68 (2000).
Moran, "The role of endotoxin in infection: Helicobacter pylori and campylobacter jejuni", Subcell Biochem.,53:209-40 (2010).
Mowad, et al., "The role of extracellular polysaccharide substance produced by *Staphylococcus epidermidis* in miliaria," J Am Acad Dermatol., 33(5 Pt 1):729-33 (1995).
Muller, "Polymorphism", Inorganic Chemistry, 14-15 (1993).
Musk, et al., "Iron salts perturb biofilm formation and disrupt existing biofilms of pseudomonas aeruginosa", Chem Biol., 12:789-96 (2005).
Nusbaum, et al., "Biofilms in dermatology," Skin Therapy Lett., 17(7):1-5 (2012).
Oberhuber, et al., "Blood groups Lewis(b) and ABH expression in gastric mucosa: lack of inter-relation with Helicobacter pylori colonisation and occurrence of gastric MALT lymphoma", Gut, 41:37-42 (1997).
Otto, "*Staphylococcus epidermidis*—the 'accidental' pathogen," Nat Rev Microbiol., 7(8):555-67 (2009).
Pearson, et al., "Colonization of broiler chickens by waterborne Campylobacter jejuni," Appl Environ Microbiol., 59:987-96 (1993).
Pradines, et al., "In vitro potentiation of antibiotic activities by a catecholate iron chelator against chloroquine-resistant Plasmodium falciparum", Antimicrob Agents Chemother.,1:225-8 (2002).
Rajan, et al., "Metal chelates of L-DOPA for improved replenishment of dopaminergic pools", Brain Res., 107:317-31 (1976).
Randhawa, et al., "Mossbauer study on the thermal decomposition of some hydroxy iron III carboxylates", Journal of Radioanalytical and Nuclear Chemistry:, 220:271-273 (1997).
Refat, et al., "Preparation, structural characterization and biological evaluation of L-tyrosinate metal ion complexes," J Mole Structure, 881:28-45 (2008).
Rosa, et al., "Interrelationship of Dietary Phosphorus , Aluminum and Iron on Performane and Tissue ineral Copostition in Lambs", J. Animal Science, 55:1231-1248 (1982).
Scheltems, et al., "PeakML/mzMatch: a file format, Java library, R library, and tool-chain for mass spectrometry data analysis," Analytical Chem., 83:2786-93 (2011).
Scifinder, "CAS registry No. 61943-75-7", retrieved from https://scifinder.cas.org/scifinder/view/scifinderExplore.jsf on Jul. 18, 2019.
Shevchenko, et al., "Mass spectrometric sequencing of proteins silver-stained polyacrylamide gels," Anal Chem., 68(5):850-8 (1996).
Shiau and Su, "Ferric Citrate is Half as Effective as Ferrous Sulfate in Meeting the Iron Requirement of Juvenile Tilapia, Oreochromis niloticus x O. aureus1", J Nutrition, 133:483-88 (2003).
Skirrow, "Epidemiology of Campylobacter enteritis," Int J Food Microbiol., 12:9-16 (1991).
Sojda, et al., "Coccidiostats and coccidiosis", DeLaval, Milkproduction.com (2005).
Summer, et al., "Proposed minimum reporting standards for chemical analysis Chemical Analysis Working Group (CAWG) Metabolomics Standards Initiative (MSI)," Metavolomics, 3:211-21 (2007).
Summer, et al., "Proposed quantitative and alphanumeric metabolite identification metric," Metavolomics, 10:1047-9 (2014).
Tautenhahn, et al., "Highly sensitive feature detection for high resolution LC/MS," BMC Bioinformatics, 9:504 (2008).
The Food and Drug Administration, "Phasing Out Certain Antibiotic Use in Farm Animals", www.fda.gov/consumers/consumer-updates/phasing-out-certain-antibiotic-use-farm-a nimals :1-4 (2013).
Turnbaugh , et al., "An obesity-associated gut microbiome with increased capacity for energy harvest," Nature, 444 (7122):1027-31 (2006).
Vippagunta, et al., "Crystalline solids", Advanced Drug Delivery Reviews, 48:18 (2001).
Written Opinion for PCT/US2016/046618 dated Jul. 27, 2018.
Written Opinion for PCT/US2016/046618 dated Jul. 27, 2017.
Written Opinion for PCT/US2016/046623 dated Jul. 26, 2017.
Yamasaki, et al., "A combination of roxithromycin and imipenem as an antimicrobial strategy against biofilms formed by *Staphylococcus aureu*," J Antimicrob Chemother., 48(4):573-7 (2001).

BIOFILM INHIBITING COMPOSITIONS ENHANCING WEIGHT GAIN IN LIVESTOCK

CROSS REFERENCE TO RELATED APPLICATIONS

This applications is a divisional of U.S. Ser. No. 15/860,989, filed Jan. 3, 2015, as a continuation-in-part of U.S. Ser. No. 15/234,941, filed Aug. 11, 2016, now U.S. Pat. No. 10,555,531, issued Feb. 11, 2020, which was a continuation-in-part to International Application No. PCT/US2015/044603, filed Aug. 11, 2015, and claims benefit of and priority to U.S. Ser. No. 62/296,386 filed Feb. 17, 2016, and U.S. Ser. No. 62/334,746 filed May 11, 2016.

FIELD OF THE INVENTION

The present invention generally relates to a class of compounds that has a broad range of microbial biofilm inhibiting antimicrobial and other activities, as well as numerous other uses, especially as feed additives.

BACKGROUND OF THE INVENTION

There is a very small profit margin in the production of beef, pork, chicken, and other types of meat, including aquaculture. Profitability frequently turns on feed efficiency and rate of gain. The first criteria relates to the amount of feed intake required to produce a specified amount of weight gain. The second criteria relates to the amount of daily weight gain (frequently referred to as average daily gain, or ADG) on a specified type and/or amount of feed, whether it is forage, grazing and/or grain. Many variables affect these performance criteria, including species, age, genetics, climate, as well as type and amount of feed, forage, grass and supplementation.

Many different compositions have been used to enhance feed efficiency and ADG. Some of these, such as growth hormone, can be overused and leave residues in the meat which then impact the consumer. Others are relatively expensive for the amount of gain. Still others require extensive regulatory testing as being pharmaceutical, not merely nutritional supplements.

It is an object to provide compositions, and methods of use thereof, to improve growth performance in livestock and aquaculture.

It is a further object to provide methods to treat or prevent infections by antibiotic resistant bacteria.

It is a still further object to provide compositions, devices, and formulations utilizing antibacterial compounds to treat or prevent biofilm formation and to disinfect surfaces and materials including meat and other products harvested from livestock.

SUMMARY OF THE INVENTION

Compounds and compositions containing the compounds have been developed which are useful as selective biofilm inhibiting compounds, which can also be utilized in formulations administered to animals to increase feed efficiency and weight gain, as well as to decrease infection by and spread of disease organisms.

These compounds have the following formula:

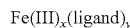

Formula I wherein
x is an integer value of 1-2,
y is an integer value of 1-3, and
each ligand present is independently a conjugate base of an α-hydroxy acid selected from citric acid, tartaric acid, lactic acid, glycolic acid, quinic acid, glycolic acid, isoleucic acid, valic acid, malic acid, and mandelic acid; or each ligand is a conjugate base of an amino acid independently selected from the group consisting of glycine, alanine, arginine, asparagine, aspartic acid, cysteine, glutamine, glutamic acid, histidine, isoleucine, leucine, lysine, methionine, phenylalanine, proline, serine, threonine, tryptophan, tyrosine, and valine; and salts and/or hydrates thereof.

Exemplary compounds include Ferric lactate (Fe-Lac), Ferric Citrate (Fe-Cit), Ferric Tartrate (Fe-Tart), Ferric Glycinate (Fe-Gly), Ferric EDTA, Ferric Malate, Ferric oxalate, Ferric Quinate (Fe-QA, also referred to herein as FeQ or QPLEX), and ferric complexes with L-tyrosine (Fe-Tyr, also referred to as TYPLEX), L-DOPA (Fe-DOPA), L-phenylalanine (Fe-Phe) and hydrates, salts, or derivatives thereof. The lactate, citrate, glycinate, tartrate, malate, oxalate, and EDTA forms have an advantage of being more water soluble, and therefore may be easier to manufacture and utilize in solution or feeds.

The compounds can be administered to an animal or human for selective inhibition of biofilm formation, as a tablet, capsule, oral solution or suspension, or incorporated into feed or feed supplement. The compositions are effective against a wide range of microbial species including *S. epidermidis, E. faecalis, E. coli, S. aureus, Campylobacter* spp. *H. pylori* and *Pseudomonas*. The compounds represent a new class of biofilm inhibitors compared to most currently in use, and are effective in treatment and prevention of microbial infections.

The compounds can also be administered in conjunction with antibiotics to reverse antibiotic resistance of bacteria, and can be used to treat antibiotic resistant bacteria by administering the compounds with antibiotics.

The compounds can be applied to a substrate such as a medical device, tubing, processing equipment, or equipment in the food, medical or computer industries where biofilm formation and bacterial contamination are an issue. The compositions may be incorporated into a coating which is sprayed on as a solution or suspension, incorporated into a laminate, film or polymer coating, or dispersed in particulate or aerosols for administration. The compounds may also be incorporated into solutions or suspensions for application as a disinfectant to an infected surface or a surface having a biofilm thereon. These may also be used as disinfectants for agricultural products such as meat.

In a particularly preferred application, the compounds are used to improve growth performance of animals such as livestock, including poultry, cattle, sheep, swine and goats, and other animals such as fish, shrimp, and other animals in aquaculture, preferably in the form of feed and formula supplements, in place of, or in combination with, existing bacteriostatic or bactericidal or growth enhancing compounds. In a preferred embodiment the compositions may be administered to animals, such as livestock, to increase growth performance. The compositions may also be used to decrease mortality adjusted feed conversion ratios (MFCR).

Examples demonstrate efficacy in enhancing weight gain in livestock including poultry (chickens) and swine.

DETAILED DESCRIPTION OF THE INVENTION

I. Definitions

Figure 1:
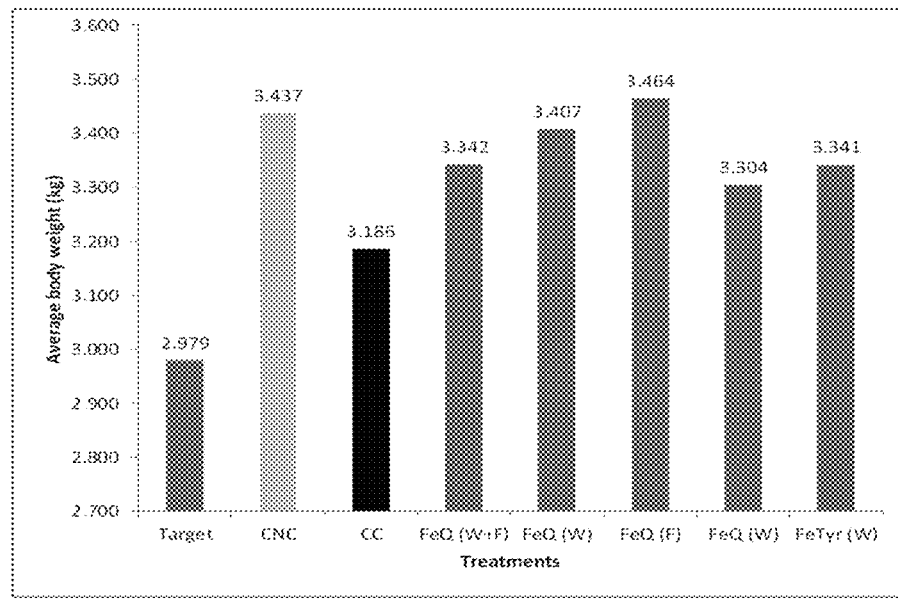
FIG. 1 is a bar graph of the average body weight at day 42 for chickens for all chicken treatment groups described in Example 1, and a comparison to a commercial control labeled "Target". Treatment group 1 is the negative control labeled "CNC". The positive control (labeled "CC") was challenged with dirty litter containing *Campylobacter* at day 20. Chickens were treated with Fe-Q or Fe-Tyr.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., C1-C30 for straight chains, and C3-C30 for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), and —CF3, —CN. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy. An "ether" is two hydrocarbons covalently linked by an oxygen. Accordingly, the substituent of an alkyl that renders that alkyl and ether is or resembles an alkoxyl, such as can be represented by one of —O-alkyl, —O— alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

"Aryl", as used herein, refers to C5-C10-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

"Biofilm" as used herein refers any group of microorganisms in which cells stick to each other on a surface.

"Cleaning formulation", as used herein, means a composition suitable for application to a surface for removing dirt and oils, for disinfecting, or a combination thereof. Cleaning formulations can be antibacterial, antimicrobial, or both. Cleaning formulations are suitable for use on the human skin, when none of the components of the composition are present at concentrations that cause significant signs of irritation when applied to human skin. As used herein, "significant signs of irritation" include erythema, redness, and/or swelling at the site of injection or at the site of application, necrosis at the site of application, exfoliative dermatitis at the site of application, and severe pain that prevents daily activity and/or requires medical attention or hospitalization. Cleaning formulations can be suitable for use in the human buccal cavity. Cleaning formulations can be suitable for use with articles that, subsequent to exposure and optionally with residual levels of cleaning composition present on and/or in the article, will then be contacted with the human skin or other part of the human body, such as wherein the article (e.g. a denture) will be contacted with the buccal cavity, or will be contacted with the eye (e.g. a contact lens). Cleaning formulations can be suitable for use with foodstuffs and/or their packaging and may, for example, be suitable for cleaning meat products and/or carcasses used in the production of meat products. Cleaning formulations may be suitable for cleaning equipment used in food production. Cleaning formulations may be suitable for use in cleaning medical devices, including implantable medical devices. Many other types of cleaning formulations may also be provided by the present invention, further examples of which are discussed in further sections of this application.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

"Inhibition" or "inhibiting" of biofilm formation as used herein refers to a decrease of biofilm associated microorganism formation and/or growth.

A "lotion" is a low- to medium-viscosity liquid formulation.

"Mortality adjusted Feed Conversion Ratio" (MFCR) is the total feed intake per pen divided by the sum of the total live weight of a pen plus the total weight of dead birds in a pen minus the total live weight of pen at the start of the period reported.

As used herein, the term "nitro" means —NO$_2$; the term "halogen" designates —F, —Cl, —Br, or —I; the term "sulfhydryl" means —SH; the term "hydroxyl" means —OH; and the term "sulfonyl" means —SO$_2$—.

"Oil" as used herein refers to a composition containing at least 95% wt. of a lipophilic substance. Examples of lipophilic substances include but are not limited to naturally occurring and synthetic oils, fats, fatty acids, lecithins, triglycerides and combinations thereof.

An "ointment" is a semisolid preparation containing an ointment base and optionally one or more active agents.

"Parenteral administration", as used herein, means administration by any method other than through the digestive tract or non-invasive topical or regional routes.

"Patient" or "subject" to be treated and/or used in accordance with any of the aspect as described herein refers to either a human or non-human animal such as a primate, non-human primate, laboratory animal, farm animal, livestock, or a domestic pet. Exemplary animals can optionally include chickens, particularly a meat-type chicken such as broiler chicken, or an egg-laying chicken such as a pullet or hen, or a breeder chicken. Also optionally included without limitation are other poultry, such as a turkey, geese, quail or ducks, or livestock, such as cattle, sheep, goats or swine, alpaca, banteng, bison, camel, cat, deer, dog, donkey, gayal, guinea pig, horse, llama, mule, rabbit, reindeer, water buffalo, yak, although the skilled person will appreciate that other animals, including zoo animals, captive animals, game animals, fish (include freshwater and saltwater fish, farmed fish, and ornamental fish), other marine and aquatic animals, including shellfish such as, but not limited to, oysters, mussels, clams, shrimps, prawns, lobsters, crayfish, crabs, cuttlefish, octopus, and squid, domestic animals such as cats and dogs, rodents (such as mice, rats, guinea pigs, hamsters), and horses, are also included, as well as any other domestic, wild and farmed animal, including mammals, marine animals, amphibians, birds, reptiles, insects and other invertebrates.

"Pharmaceutically acceptable" as used herein refers to those compounds, materials, compositions, and/or dosage forms which are, within the scope of sound medical judgment, suitable for use in contact with the tissues of human beings and animals (such as one or more of the animal "patients" or "subjects" as discussed above) without excessive toxicity, irritation, allergic response, or other problems or complications commensurate with a reasonable benefit/risk ratio.

"Pharmaceutically acceptable salt", as used herein, refers to derivatives of the compounds defined herein, wherein the parent compound is modified by making acid or base salts thereof.

"Therapeutically effective" or "effective amount" as used herein means that the amount of the composition used is of sufficient quantity to ameliorate one or more causes or symptoms of a condition, bacterial colonization, disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

The term "substituted" as used herein, refers to all permissible substituents of the compounds. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted C3-C20 cyclic, heterocyclic, substituted heterocyclic, amino acid, peptide, and polypeptide groups.

"Treatment", "treating", or "alleviating" as used in connection with a disease or infection refers to an intervention performed with the intention of altering or inhibiting the pathology of a disorder.

II. Methods of Making and Use

Iron complexes, preferably with a molecular weight of the complex less than 1,000 g/mol, are useful for:
Enhancement of animal growth;
Potentiating the effect of antibiotics and other antimicrobial agents, and addressing antibiotic resistance;
Inhibition of formation, and treatment of preformed, biofilms; treating microbial infections reducing microbial colonization; and disinfecting surfaces.

Preferred compound include compounds represented by Formula I below, particularly, ferric lactate (also referred to herein as Fe-Lac), ferric citrate (also referred to herein as Fe-Cit), ferric tartrate (also referred to herein as Fe-Tart) and ferric glycinate. Others include ferric EDTA, ferric malate, and ferric oxalate.

A. Enhancement of Animal Growth

A method of enhancing the growth of an animal, the method comprising causing the animal to ingest and/or absorb an effective amount of one or more iron compounds described herein.

Typically, in one embodiment one or more of the compounds will be presented directly to the animal for ingestion and/or absorption. However, in one alternative optional embodiment the animal may be caused to ingest or absorb one or more of the compounds by providing the animal simultaneously, separately or sequentially with components which cause the animal to form an effective amount of the one or more compounds, in situ. For example, the animal could be provided with a source of ferrous sulfate and simultaneously, separately or sequentially with a source of quinic acid or salt thereof (or other α-hydroxyacid), or could be provided with a source of ferrous sulfate and simultaneously, separately or sequentially with a source of a natural or synthetic amino acid, such as L-tyrosine, L-DOPA or L-phenylalanine.

In one embodiment the one or more compounds are a complex of an amino acid with Fe III and a complex of an α-hydroxyacid with Fe III, or salts and/or hydrates thereof. For example, one or more compounds may be selected from any one or more of the group consisting of a complex of quinic acid with Fe III, a complex of L-tyrosine with Fe III, a complex of L-DOPA with Fe III, and a complex of L-phenylalanine with Fe III, ferric lactate (also referred to herein as Fe-Lac), ferric citrate (also referred to herein as Fe-Cit), ferric tartrate (also referred to herein as Fe-Tart) and ferric glycinate (also referred to herein as Fe-Gly). Optionally, the one or more compounds is not a complex of quinic acid with Fe III.

The animal may be caused to ingest or absorb the one or more of the compounds, by providing the one or more compounds (or component parts thereof to form the compound(s) in situ) by dietary means, such as in or mixed with an animal feed, as a dietary supplement, and/or in a drinking water. A further option, in the case of marine, aquatic, amphibious or other animals that live partially or fully in water, is to add the one or more compounds (or component parts thereof to form the compound(s) in situ) into the water, such as by treatment of ponds containing farmed fish or crustaceans such as shrimp and crawfish. It should be noted that, dependent on the solubility of the one or more compounds used, it may be beneficial to introduce a co-solvent to solubilize to aid dissolution in water at an effective concentration.

1. Method of Making Fortified Animal Feed or Feed Supplement

Methods for the production of a biofilm inhibitor-fortified animal feed product or animal feed supplement product are provided. Exemplary animal feed include feed for a chicken (including a broiler chicken and an egg laying chicken). The method includes the steps of incorporating one or more of the compounds into the animal feed product or animal feed supplement product during the preparation of the feed or supplement. An animal feed for use in the methods described herein may include, one or more compounds of the compounds in an amount of 0.001 to 20 g of the one or more compounds per kg of feed, such as 0.002 to 15 g/kg, or at a level of, up to, or at least, about 0.002 g/kg, 0.005 g/kg, 0.01 g/kg, 0.02 g/kg, 0.03 g/kg, 0.04 g/kg, 0.05 g/kg, 0.1 g/kg, 0.2 g/kg, 0.3 g/kg, 0.4 g/kg, 0.5 g/kg, 1 g/kg, 2 g/kg, 3 g/kg, 4 g/kg, 5 g/kg, 10 g/kg, 15 g/kg or 20 g/kg. An animal drinking water supply of, or for use in, the first aspect may comprise, or be supplemented with, one or more compounds in an amount of 0.001 to 20 g of the one or more compounds per L of water, such as 0.002 to 15 g/L, or at a level of, up to, or at least, about 0.002 g/L, 0.005 g/L, 0.01 g/L, 0.02 g/L, 0.03 g/L, 0.04 g/L, 0.05 g/L, 0.1 g/L, 0.2 g/L, 0.3 g/L, 0.4 g/L, 0.5 g/L, 1 g/L, 2 g/L, 3 g/L, 4 g/L, 5 g/L, 10 g/L, 15 g/L or 20 g/L. The same concentrations can apply to water in which aquatic or other animals live The one or more compounds may be incorporated into the product at any stage during the production process including before one or more heating steps, such a one or more heating steps that include exposing a composition including the one or more compounds to a temperature of greater than 50° C., greater than 60° C., greater than 70° C., greater than 80° C., greater than 90° C. or greater than 100° C., and preferably wherein the temperature exposure is in a range selected from 50-200° C., 60-150° C., 70-100° C. In some embodiments, a temperature range for a heating step may be in the range of 70–90° C., such as 75-88° C., 80-87° C., 81-86° C., or 82-85° C.

Optionally, a suitable method for the production of an animal feed, such as a feed for a chicken (including a broiler chicken) may include the steps of:

(a) combining nutritional and/or other dietary components (such as one or more components selected from wheat, soy, soy oil, minerals and other additives) to form a grist or other mixture;

(b) heating the grist or other mixture in a heating step as described above, such as with steam at 85° C. for a time effective to kill any pathogens, such as *Salmonella*. A period of 5-10 minutes, such as 6-8 minutes, is one example of an effective period at 85° C., although the time can be adjusted dependent on the temperature used;

(c) cooling the heated mixture. Preferably the cooling is conducted at a rate and under conditions effective to avoid the formation of condensation, since condensation can result in the growth of pathogens including *Salmonella*.

(d) optionally pressing the cooled mixture;

(e) forming feed pellets from the cooled mixture, such as by pelletizing using an extruder that heats the feed to a suitable temperature, as discussed above, for example in the range of 82-85° C.;

(f) addition of heat sensitive additives, typically by spraying. Heat sensitive additives can include enzymes, which may (for example) be selected from the group consisting of phytase, xylase, beta-lactamase.

In accordance with the foregoing method for the production of an antibiotic fortified animal feed product, the method comprising the step of incorporating one or more of the compounds into the animal feed product at any one or more stages of the production, including during step (a), between steps (a) and (b), during step (b), between steps (b) and (c), during step (c), between steps (c) and (d), during step (d), between steps (d) and (e), during step (e), between steps (e) and (f), during step (f), or after step (f).

The one or more compounds may be included in an animal feed, or in an animal feed supplement or premix, for the feed of commercial birds such as chickens, turkeys, pheasants, and ducks. In one option, the one or more compounds may be included in, or used to supplement, a poultry feeds, which can be a "complete" feed. A complete feed is designed to contain all the protein, energy, vitamins, minerals, and other nutrients necessary for proper growth, egg production (if the bird is an egg layer), and health of the birds.

Chickens used in optimized commercial broiler production are typically fed different diets depending upon their age. For example, chickens for broiler production may be raised using three diets. These diets are typically called a "starter", "grower" and "finisher". "Pre-starter" diets are also possible. According, the compounds disclosed herein may be included in a starter diet only, a grower diet only, a finisher diet only, a combination of any two or a combination of all three.

The "starter", "grower" and "finisher" are typically distinguished by crude protein content, which is often provided by ingredients such as soybean meal (SBM). For example, a starter diet for a broiler chicken may optionally contain crude protein contents of around 22-25% by weight, such as 22%, 23%, 24% or 25%, with 23 or 25% being preferred. In a further example, a grower diet for a broiler chicken may optionally contain crude protein contents of around 21-23% by weight, such as 21%, 22% or 23%, with 22% being preferred. In a further example, a finisher diet for a broiler chicken may optionally contain crude protein contents of around 19-23% by weight, such as 19%, 20%, 21%, 22% or 23%, with 19%, 20%, or 21% being preferred.

Additionally or alternatively, the "starter", "grower" and "finisher" may be distinguished by metabolizable energy (ME) content, which is typically lowest for the starter diet and highest for the finisher diet, with the grower diet having a level between the two. For example, a starter diet for a broiler chicken may have an ME of about 3000 or 3025 kcal/kg (±50, 40, 30, 20, 10, 5 or less kcal/kg). In a further example, a grower diet for a broiler chicken may have an ME of about 3100 or 3150 kcal/kg (±50, 40, 30, 20, 10, 5 or less kcal/kg). In a further example, a grower diet for a broiler chicken may have an ME of about 3200 kcal/kg (±50, 40, 30, 20, 10, 5 or less kcal/kg).

An animal feed or animal feed supplement fortified as described herein may either be a vegetarian or non-vegetarian product. A vegetarian product contains no meat or fish products. A non-vegetarian diet may contain either, or both, fish product (such as fish meal) or meat product (such as meat derivatives, bone meal, etc.).

Similar feed compositions can be made for feeding swine, other types of poultry (ducks, turkeys, pigeons), rabbits, as well as other types of livestock such as sheep, goats, and cattle.

Feed compositions are well known for other species of animals, including ruminants such as cattle, sheep and goats, swine, horses, fish and crustaceans (shrimp, crawfish, etc.). Many of these are specific for the age of the animal, such as while still nursing, at weaning, at time of maximum weight gain, during reproduction, and for maintenance. An appropriate amount of compound can be added for purposes such as maximizing weight gain or maintaining or restoring gastrointestinal balance (especially during times of stress such as following antibiotic treatment and at weaning).

2. Method of Making Animal Fortified Drinking Water

Methods for the production of biofilm inhibitor-fortified animal drinking water are also provided. The methods include the addition of one or more of the compounds into an animal drinking water supply. Suitable concentrations of the one or more compounds in a drinking water supply are typically in a concentration effective to produce the effect of enhanced growth in an animal when compared to growth of the animal on drinking water not containing the compounds. A determination of a suitable concentration may take into account the amount of drinking water consumed by the animal. For example, a broiler chicken in the UK (or at an equivalent temperature to those used in the UK) typically consumes a daily amount of drinking water dependent on its age that can be calculated by reference to the age of the chicken in days multiplied of approximately 4-10 mL, such as 5-9 ml, 6-8 mL, for example about 7.14 mL. Thus, for example, a 42 day old broiler chicken may have a daily water consumption of 168 mL to 420 mL per day, more typically around 300 mL per day ±30%, 20%, 15%, 10%, 5%, 4%, 3%, 2%, or 1%. Broiler chicken reared at different temperatures may consume more (e.g. in southern USA, where temperatures in the summer will be high and water consumption could be higher, particularly in sheds where temperature is not controlled), or less water.

The animal may ingest or absorb an effective amount of one or more of the compounds on a regular and repeated basis. For example, the animal may ingest or absorb an effective amount of one or more compounds weekly, every other day, every day, or more than once every day during the performance of the method or use. In one option, the one or more compounds are included in the an animal feed, an animal feed supplement, and/or in drinking water and the animal ingests the one or more compounds when they eat and/or drink, and optionally every time they eat and/or drink. This ingestion or absorption an effective amount of one or more compounds may continue through a period of time of the animal's growth that may correspond to a period of time that is, is up to, or is at least, 5%, 10%, 25%, 30%, 40%, 50%, 60%, 70%, 80%, 90%, 95% or substantially 100% of the life of the animal from birth to death. The ingestion or absorption an effective amount of one or more compounds may start on the day of the animal's birth, or at the age of 1, 2, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47 days, or more. After the animal starts to ingest or absorb the one or compounds, the animal may continue to do so on a regular and repeated basis for a period of time that can be, or be up to, or at least, 1, 2, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47 days, or more.

In the case of chickens, especially broiler chickens, the one or more compounds are preferably ingested on a repeated and regular basis in a starter diet, in a grower diet and/or in a finisher diet, as described herein.

An animal drinking water supply of, or for use in, the methods disclosed herein, can include or be supplemented with, one or more compounds in an amount of 0.001 to 20 g of the one or more compounds per L of water, such as 0.002 to 15 g/L, or at a level of, up to, or at least, about 0.002 g/L, 0.005 g/L, 0.01 g/L, 0.02 g/L, 0.03 g/L, 0.04 g/L, 0.05 g/L, 0.1 g/L, 0.2 g/L, 0.3 g/L, 0.4 g/L, 0.5 g/L, 1 g/L, 2 g/L, 3 g/L, 4 g/L, 5 g/L, 10 g/L, 15 g/L or 20 g/L. The same concentrations can apply to water in which aquatic or other animals live.

3. Additional Additives

Other additives include one or more additives selected from the list consisting of creatine, amino acids (e.g. threonine) and salt, and macro minerals, which include those selected from the group consisting of calcium, phosphorus, magnesium, sodium, potassium and chloride.

Trace Minerals, Including Zinc and/or Selenium.

Added vitamins, which include those selected from the group consisting of vitamin A, nicotinic acid, pantothenic acid, pyridoxine (B6) and biotin in maize and wheatbased feed. Additionally there is a basic requirement of broiler chickens for vitamin E at 10-15 mg/kg. The need for extra supplementation with vitamin E will depend on the level and type of fat in the diet, on the level of selenium and on the presence of pro- and antioxidants. Heat treatment of feeds can result in the destruction of up to 20% of vitamin E Choline may also be given in a complete feed.

Non-nutritive feed additives may also be included. Enzymes are routinely used in poultry feeds to improve digestibility of feed ingredients. In general, feed enzymes are available that act on carbohydrates, plant bound minerals and proteins. Non Starch Polysaccharide (NSP) enzymes are economically beneficial in wheat-based feeds. These enzymes will also allow greater flexibility in the levels of barley to be included in the ration. Phytase enzymes can be used to enhance phytate phosphorus utilization. Protease enzymes can be included to act upon vegetable products. Carbohydrase enzymes can be added, and may provide beneficial responses when used in maize-soya diets. When adding enzymes before heat processing of broiler feeds, there is the potential for a loss in enzyme activity. This may be avoided by spraying enzymes on to the feed at the end of processing.

Medicinal and prophylactic drugs (other than the compounds. below) may be added. A wide range of medicinal products, e.g. coccidiostats and antibiotics, may be administered through the feed. Antibiotic Growth Promoters/Digestion Enhancers can be included and can, for example, provide a mode of action involving modification of the gut microflora, with consequential benefits in nutrient utilization.

Prebiotics can be added, and refer to a group of substances which stimulate the growth of beneficial microorganisms, at the expense of harmful, micro-organisms. Oligosaccharides form the largest group of these products at present.

Probiotics can be added to introduce live micro-organisms into the digestive tract to assist the establishment of a stable and beneficial microflora. The objective is to provide the gut with positive, non-pathogenic micro-organisms which will then prevent colonization with pathogenic micro-organisms by competitive exclusion.

Organic Acids may be added. Organic acid products can be used to reduce bacterial contamination of the feed (e.g. after heat treatment) and can also encourage beneficial microflora to develop in the digestive tract of the bird.

Absorbents are used specifically to absorb mycotoxins. They may also have a beneficial effect on general bird health and nutrient absorption. There are a range of products available for use as absorbents, including various clays and charcoal.

Antioxidants can provide important protection against nutrient loss in broiler feeds. Some feed ingredients e.g. fish meal and fats, can be protected. Vitamin premixes should be protected by an antioxidant unless optimum storage times and conditions are provided. Additional antioxidants may be added to the final feed where prolonged storage or inadequate storage conditions are unavoidable.

Anti-Mold Agents can be added. For example, mold inhibitors may be added to feed ingredients, which have become contaminated, or to finished rations to reduce growth of fungi and production of mycotoxins.

Pelleting agents can be added, and are used to improve pellet hardness. Some examples of pellet binders are hemicellulose, bentonite and guar gum.

Other products of possible use in broiler production include essential oils, nucleotides, glucans and specialized plant extracts. In areas of the world where its use is permitted, formaldehyde can be used to treat/preserve feed.

Without limitation, exemplary "starter", "grower" and "finisher" diets include those shown in the examples.

4. Method of Feeding Animals

Although the following is specific with respect to chickens, appropriates amounts and timing of feeding are known to those skilled in the art and readily ascertainable, as demonstrated by the following examples.

The starter diet with broiler chicks may be fed for about the first 10-12 days (typically in the range of the first 7-14 days of life). This starter diet may be followed by the grower diet, which is provided to the broilers for almost 2 weeks (typically from the age of about 11-24 days, although in any case, after the end of the use of the starter diet). The finisher diet may be used for the remainder of the production period (typically from the age of about 24, or 25, days to harvest). Some broiler houses will use more or less diets (for example 4 diets), and vary the timing of diet changes. Broilers are typically harvested between 35 and 42 days, although this time can be longer or shorter. The UK market typically harvests at day 30-35. Other countries, including some European countries, harvest as early as 25 days, although more typically from 30 days onwards. Other countries, such as the US, typically harvest at 42-47 days. Non-broiler chickens, including free-range chickens, may be harvested at later ages. Any age of harvest may be used, although most typically (e.g. in the context of broiler chickens) after the start of the finisher diet, and optionally (and without limitation) on any of days 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or beyond, such as up to or about 11 weeks, 12 weeks, 13 weeks, 14 weeks, 15 weeks, 16 weeks, 17 weeks, 18 weeks, 19 weeks, 20 weeks or more.

In some embodiments methods for the production of broiler chicken or other animals may be performed on groups that are single sex (i.e. groups of solely female, or solely male animals), and/or may be performed on groups of mixed sex (i.e. mixed male and female) animals. For example, in the case of the production of broiler chickens, it may be appropriate to select and rear together a single sex group of male cockerels, and it may be suitable to harvest the cockerels at an earlier age than female or mixed sex groups. For example, a single sex cockerel group of broiler chickens may be harvested at the age of around 30 days or, in other options, at the age of any one or more of 25, 26, 27, 28, 29, 30, 31, 32, 33, 34, 35, or more days. For example, at the age of 30 days, an untreated cockerel group may have an average target weight of about 1.95 kg, whereas in the case of the enhanced growth resulting from the methods disclosed herein, it may be appropriate to harvest the cockerels at an earlier stage at the defined target weight, or to harvest at the same age and a higher average weight, or at the same age and target weight with the use of a reduced consumption of animal feed due to greater feed conversion efficiency. In a further example, a mixed sex group of broiler chickens may be harvested at the age of around 35 days or, in other options, at the age of any one or more of 25, 26, 27, 28, 29, 30, 31, 32, 33, 34, 35, 36, 37, 38, 39, 40, 41, 42, 43, 44, 45, 46, 47, 48, 49, 50 or more days. For example, at the age of 35 days, an untreated mixed sex group may have an average target weight of about 2.1-2.2 kg, whereas in the case of the enhanced growth resulting the methods disclosed herein, it may be appropriate to harvest the mixed sex group at an earlier stage at the defined target weight, or to harvest at the same age and a higher average weight, or at the same age and target weight with the use of a reduced consumption of animal feed due to greater feed conversion efficiency.

In embodiments where the animal to be grown is an egg-laying chicken, a typical process of rearing an egg-laying chicken can involve the beginning of egg production at around 23 weeks of age, and slaughter at around 60 weeks of age. The egg-laying chicken may be exposed to the one or more compounds prior to beginning egg laying, and/or during egg laying, and/or up to the time of slaughter. Treatment may, for example, last for about 5, 10, 15, 20, 25, 30, 35, 40, 45, 50, 55, or 60 weeks; the term "about" in that context can include the meaning of ±4, 3, 2, or 1 weeks of the stated value. Whereas, typically, egg laying chickens begin to lay eggs at 23 weeks of age, by taking advantage of the methods disclosed herein for enhanced growth and/or enhanced feed utilization it may be appropriate to begin egg production at an earlier age, such as at 18, 19, 20, 21 or 22 weeks of age. Further, by taking advantage of the methods disclosed herein for enhanced growth and/or enhanced feed utilization the present invention may be used to achieve an effect (compared to an untreated control group that is reared under identical conditions except for the application of the compounds) selected from:

(a) the production with eggs of improved quality. Improved quality may, for example, be selected from size, shell quality, air cell, white and yolk. The shell quality is determined from any one or more of size, visual defects, specific gravity, color, breaking strength, percent shell (shell weight×100/egg weight), shell thickness, and ultrastructure of the egg. The improved quality may be reflected in a higher proportion of eggs being categorized as US grade A or AA;

(b) the production of eggs of increased size (such as at a weight that is up to, or at least, 1%, 2%, 3%, 4%, 5%, 6%, 7%, 8%, 9%, 10%, 15%, 20% or more); and/or (c) the production of eggs in increased numbers (such as in an average daily amount, per group of at least 100 animal and/or when assessed over a period of at least 10 days, that is an amount that is up to, or at least, 1%, 2%, 3%, 4%, 5%, 6%, 7%, 8%, 9%, 10%, 15%, 20% or more). The same approach can be taken with other egg-laying animals. Eggs produced by egg-laying chickens and other animals are labelled with information to indicate the source and date/or of origin.

Also provided herein are one or more eggs, such as a box or carton of eggs, produced by the animals (especially egg-laying chickens) that have been treated by one of more of the disclosed methods. As indicated above, such eggs will typically carry a label indicating their source and/or date of origin. Also provided are downstream products, especially food products, produced from and/or containing eggs or parts thereof produced by the animals (especially egg-laying chickens) that have been treated by one or more of the disclosed methods.

In some embodiments, the disclosed methods and uses are conducted such that, during the course of the treatment, the animal ingests and/or absorbs a daily mean average total of FeQ (or an equivalent number of moles of any other one or more compounds) of, of up to, or at least, about 1 μg, 10 μg, 100 μg, 500 μg, 1 mg, 10 mg, 100 mg, 1 g, 2 g, 3 g, 4 g, or 5 g.

In an additional or alternative option, the disclosed methods and uses are conducted such that, during the course of the treatment, the animal ingests and/or absorbs a total of FeQ (or an equivalent number of moles of any other one or more compounds) of, of up to, or at least, about (a) 5 mg, 10 mg, 50 mg, 100 mg, 500 mg, 1 g, 5 g, 10 g, 50 g or 100 g per individual animal and/or (b) 1 mg, 2 mg, 3 mg, 4 mg, 5 mg, 10 mg 50 mg, 100 mg, 200 mg, 300 mg, 400 mg, 500 mg, 600 mg, 700 mg, 800 mg, 900 mg, 1 g, 1.1 g, 1.2 g, 13 g, 1.4 g, 1.5 g, 1.6 g, 1.7 g, 1.8 g, 1.9 g, 2 g, 2.1 g, 2.2 g, 2.3 g, 2.4 g, 2.5 g, 2.6 g, 2.7 g, 2.8 g, 2.9 g, 3 g, 3.5 g, 4 g, 4.5 g, 5 g, 6 g, 7 g, 8 g, 9 g, 10 g, 20, g, 30 g, 40 g, 50 g, 60 g, 70 g, 80 g, 90 g or 100 g per kg of final average body weight, as determined at the day of the final administration of the one or more compounds.

The method of enhancing the growth may be practiced on multiple animals, which may optionally be reared together and, further optionally wherein all animals reared together may be aged matched to within a month, a week, or less, such as within 6, 5, 4, 3, 2 or 1 days of each other.

For example, the method may be practiced on a group of up to, about, or at least, 2, 3, 4, 5, 6, 7, 8, 9, 10, 15, 20, 25, 30, 35, 40, 45, 50, 55, 60, 70, 80, 90, 100, 150, 200, 250, 300, 400, 500, 600, 700, 800, 900, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$ or more, and all animals in the group may be optionally age matched as indicated above. The term "about" in this context can mean within ±50%, ±40%, ±30%, ±20%, ±10%, ±5%, ±4%, ±3%, ±2%, ±1% or less of the stated value.

5. Animals to be Treated

The animals treated as disclosed herein may be healthy animals, for example, animals which are not infected with or disadvantageously colonized by bacteria or other microorganisms. In another embodiment, the animals may be unhealthy animals, for example, animals which are infected with and/or disadvantageously colonized by bacteria or other microorganisms. An example of a disadvantageous bacterial colonization is *Campylobacter* colonization in the GI tract of chickens; *Campylobacter* is not pathogenic and does not cause disease in the chicken itself (although of course it can lead to food poisoning if present in a downstream meat product produced from the chicken)—nevertheless, the *Campylobacter* colonization can be considered disadvantageous to the chicken as it reduces its ability to grow or efficiently utilize feed. As such, in one embodiment, an animal that is disadvantageously colonized by bacteria or other microorganisms is an animal which displays a reduced rate of growth, reduced body weight, reduced weight gain, or less efficient feed conversion ratio due to the colonization, compared to a control animal that differs only in that it does not have the colonization.

In some embodiments, the animal may be animal that have been exposed to the litter (including feacal matter) of one or more other animals of the same or different species. Optionally, the litter may be from unhealthy animals which, for example, animals which are infected with and/or disadvantageously colonized by bacteria or other microorganisms. In one embodiment the animals treated may be chickens, such as broiler chickens, and they may have been exposed to the litter of other chickens, such as dirty litter as described in the present examples and/or carrying one or more pathogens, such as *Actinobacillus, Bordetalla, Campylobacter, Clostridium, Corynebacterium, Escherichia coli, Globicatella, Listeria, Mycobacterium, Salmonella, Staphylococcus*, and *Streptococcus*. As such, the animals to be treated may be chickens (or other animals) that are infected and/or colonized by one or more of the foregoing pathogens.

Accordingly, in some embodiments, the disclosed methods and uses may be non-therapeutic, in the sense that the animal to be treated is healthy and/or the method and use comprises the eventual slaughter of the animal. In other embodiments, the disclosed methods and uses may include therapeutic benefits to the animals to be treated.

In one embodiment, the disclosed methods and uses of enhancing the growth of an animal can include enhancing one or more characteristics selected from the group consisting of enhancing body weight or (in the case of a group of animals) average body weight (ABW), feed intake or (in the case of a group of animals) average feed intake (AFD), weight gain or (in the case of a group of animals) average weight gain (AWG), feed conversion ratio (FCR) and/or mortality adjusted feed conversion ratio (MFCR).

In one embodiment (for example, in the context of a group of chickens grown in a pen) MFCR over a given period can be calculated as follows:

MFCR=Total feed intake of period per pen/((total live weight of pen+total weight of dead birds in pen)−total live weight of pen in previous period)

For example for period 0 to 20 day, MFCR can be calculated as:

$MFCR_{0\ to\ 20\ day}$=Total feed intake$_{0\text{-}20\ days}$/((Total body weight$_{at\ day\ 20}$+mortality weight$_{0\text{-}20\ days}$)−Total body weight$_{day\ 0}$).

The enhancement in growth of the animal may be assessed over any convenient period during the animal's growth. It may, for example, be assessed from birth to a predetermined time point, such as up to about 10, 20, 30, 40, 50, 60, 70, 80, 90, 100, 110, 120, 130, 140, 150, 160, 170, 180 or more days. The term "about" in this context can mean±5, ±4, ±3, ±2, or ±1 days. It may, for example, be assessed from birth to a predetermined time point, such as up to about 10%, 20%, 30%, 40%, 50%, 60%, 70%, 80%, 90%, 95%, 96%, 97%, 98%, 99% or 100% of the life span of the animal. It may, alternatively, not be measured from birth but be measured over a period of the animal's life lasting up to about 10, 20, 30, 40, 50, 60, 70, 80, 90, 100, 110, 120, 130, 140, 150, 160, 170, 180 or more days. Again, the term "about" in this context can mean±5, ±4, ±3, ±2, or ±1 days. It may, alternatively, not be measured from birth but be measured over a period of the animal's life representative of about 10%, 20%, 30%, 40%, 50%, 60%, 70%, 80%, 90%, 95%, 96%, 97%, 98%, or 99% of the life span of the animal.

In embodiments to enhance the growth of broiler chickens, which are typically slaughtered at the average age of 35 days (in the EU) and 47 days (in the US), enhanced growth may be measured from birth up to the age of slaughter, or may be measured up to an earlier age, such as up to 10, 11, 12, 13, 14, 15, 16, 17, 18, 19, 20, 21, 22, 23, 24, 25, 26, 27, 28, 29, 30, 31, 32, 33, 34, 36, 36, 37, 38, 39, 40, 41, 42, 43, 44, 45, 46 or 47 days. Alternatively, the enhanced growth of broiler chickens may not be measured from birth but may be over another period of the broiler chicken's life lasting, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 36, 37, 38, 39, 40, 41, 42, 43, 44, 45, 46 or 47 days.

Enhanced growth can, in some embodiments, refer to an enhancement in growth in a subject animal compared to a control which is the same breed of animal as the subject, or an enhancement in a subject group of animals compared to a control group of an equivalent number of animals of the same breed as the subject group, wherein the subject and control are the same age or average age (ideally within a margin of error of less than one day), wherein growth is measured over the same period of time (ideally within a margin of error of less than one day), and wherein the subject and control are reared under the same conditions, differing only in that the subject receives one or more of the compounds whereas the control does not.

In the disclosed methods to enhance the growth of animals, and in particular poultry, such as chickens and more preferably broiler chickens, an enhancement in the rate of growth may constitute a reduction in the MFCR of the subject by, by up to, or by at least, about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19 or 0.20. The term "about" in this context may include the meaning of $\pm 5 \times 10^{-3}$. The reduction in MFCR may, for example, be measured between days 0 to 20, or days 20 to 42 of the life of the animal(s). Under current economic conditions, it can be calculated that a reduction in MFCR of 0.1 will lead to an approximate saving in feed cost of about 4 US cents per bird over a 42 day growth period and/or about £10 GBP per tonne of animal feed used. It will be appreciated that these are substantial savings in an industry in which costs are typically controlled at a level of about 0.01 US cents per bird.

In the methods of or use of the compounds to enhance the growth of animals, and in particular poultry, such as chickens and more preferably broiler chickens, an enhancement in the rate of growth may constitute an increase in the ABW of the subject by, by up to, or by at least, about 10 g, 20 g, 30 g, 40 g, 50 g, 60 g, 70 g, 80 g, 90 g, 100 g, 110 g, 120 g, 130 g, 140 g, 150 g, 160 g, 170 g, 180 g, 190 g, 200 g, 210 g, 220 g, 230 g, 240 g, 250 g or more. The term "about" in this context may include the meaning of ±5 g, 4 g, 3 g, 2 g or 1 g. The increase in the ABW may, for example, be measured between days 0 to 20, or days 20 to 42 or the life of the animal(s). The increase in the AWG may, for example, be measured between days 0 to 20, or days 20 to 42 of the life of the animal(s), or during a period of time selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 36, 37, 38, 39, 40, 41, 42, 43, 44, 45, 46 or 47 days. In the context of animals that normally (i.e. when not treated in accordance with disclosed methods) have a higher ABW than the normal ABW of broiler chickens (i.e. when not treated in accordance with the disclosed methods), then the foregoing values may be increased proportionately. That is, for example, in the case of an animal that has a normal ABW 10-fold greater than the normal ABW of a broiler chicken, then the enhancement in the rate of growth may constitute an increase in the ABW of the subject by, by up to, or by at least, about 100 g, 200 g, 300 g, 400 g, 500 g, 600 g, 700 g, 800 g, 900 g, 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g or more, wherein the term "about" in this context may include the meaning of ±50 g, 40 g, 30 g, 20 g or 10 g.

Further, in the context enhancing the growth of animals, and in particular poultry, such as chickens and more preferably broiler chickens, an enhancement in the rate of growth may constitute an increase in the average weight gain (AWG) of the subject by, by up to, or by at least, about 10 g, 20 g, 30 g, 40 g, 50 g, 60 g, 70 g, 80 g, 90 g, 100 g, 110 g, 120 g, 130 g, 140 g, 150 g, 160 g, 170 g, 180 g, 190 g, 200 g, 210 g, 220 g, 230 g, 240 g, 250 g, 260 g, 270 g, 280 g, 290 g, 300 g or more over a period of growth, compared to a control animal or group of animals. The term "about" in this context may include the meaning of ±5 g, 4 g, 3 g, 2 g or 1 g. The increase in the AWG may, for example, be measured between days 0 to 20, or days 20 to 42 of the life of the animal(s), or during a period of time selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 36, 37, 38, 39, 40, 41, 42, 43, 44, 45, 46 or 47 days. In the context of animals that normally (i.e. when not treated in accordance with the present invention) show a higher AWG than the normal AWG of broiler chickens (i.e. when not treated in accordance with the present invention), then the foregoing values may be increased proportionately. That is, for example, in the case of an animal that has a normal AWG 10-fold greater than the normal AWG of a broiler chicken over an equivalent period of time, then the enhancement in the rate of growth provided by the present invention may constitute an increase in the AWG of the subject by, by up to, or by at least, about 100 g, 200 g, 300 g, 400 g, 500 g, 600 g, 700 g, 800 g, 900 g, 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g, 2600 g, 2700 g, 2800 g, 2900 g, 3000 g or more, wherein the term "about" in this context may include the meaning of ±50 g, 40 g, 30 g, 20 g or 10 g.

In the US, the average age of slaughter of a broiler chicken is 47 days at an average weight of 2.6 kg; at the age of 42 days, the average weight may be around 2.5 kg, and in the EU, the average age of slaughter of a broiler chicken 35 days at an average weight of 2.1-2.2 kg. It will be appreciated that, as a result of the enhanced growth provided by the methods and uses disclosed herein, it will be possible to reach the target weight and harvest the animal or animal products at an earlier stage of the animal's life than would be possible with a control. For example, in the context of a broiler chicken, it may be possible to slaughter the animal after having achieved a target body weight 1, 2, 3, 4, 5, 6, 7, 8, 9, 10 or more days earlier than a control. In that context, a target body weight of a broiler chicken may be, may be up to, or may be at least, about 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g, 2600 g, 2700 g, 2800 g, 2900 g, 3000 g, 3100 g, 3200 g, 3300 g, 3400 g, 3500 g or more. The term "about" in that context may include ±50 g, ±40 g, ±30 g, ±20 g or ±10 g of the stated value. To put it another way, the broiler chicken may be slaughtered at, or prior to, the age of 47, 46, 45, 44, 43, 42, 41, 40, 39, 38, 37, 36, 35, 34, 33, 32, 31, 30, 29, 28, 27, 26 or 25 days, ideally wherein it has reached a target body weight at the time of slaughter. Thus, for example, in one embodiment, the broiler chicken is reared to a target weight of about 2.6 kg, and the method or use includes the step of slaughtering the animal after having achieved a target body weight 1, 2, 3, 4, 5, 6, 7, 8, 9, 10 or more days earlier than the age of 47 days. In another exemplary embodiment, broiler chicken is reared to a target weight of about 2.5 kg, and the method or use includes the step of slaughtering the animal after having achieved a target body weight 1, 2, 3, 4, 5, 6, 7, 8, 9, 10 or more days earlier than the age of 42 days. In another exemplary embodiment, broiler chicken is reared to a target weight of about 2.2 kg, and the method or use includes the step of slaughtering the animal after having achieved a target body weight 1, 2, 3, 4, 5, 6, 7, 8, 9, 10 or more days earlier than the age of 35 days.

In another embodiment, the animal is reared for the same amount of time as the industry standard, but presents a greater body weight (such as about, at least, or up to, 0.1%. 0.5%. 1%. 2%. 3%, 4%, 5%, 10%, 15%, 20%, 25% or more) than the industry standard at the end of the rearing process. Thus, in the context of broiler chickens, the animal may be slaughtered at a weight of about 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g, 2600 g, 2700 g, 2800 g, 2900 g, 3000 g, 3100 g, 3200 g, 3300 g, 3400 g, 3500 g or more, wherein at the time of slaughter body weight is about, at least, or up to, 0.1%. 0.5%. 1%. 2%. 3%, 4%, 5%, 10%, 15%, 20%, 25% or more than the control. The term "about" as it is applied to weight in that context may include ±50 g, ±40 g, ±30 g, ±20 g or ±10 g of the stated value.

In yet another embodiment, as a result of the effect of the enhanced growth provided by the disclosed methods and uses, the animal is able to utilize animal feeds with greater efficiency than a control. Accordingly, in another embodiment, the disclosed methods and uses include the option of rearing an animal to reach a target body weight using less animal feed than is required for a control to reach the target weight. For example, it may be possible to rear an animal to reach the target weight using an amount of fortified animal feed as disclosed herein that is reduced in weight by 0.01%, 0.05%, 0.1%, 0.2%, 0.3%, 0.4%, 0.5%, 1%, 2%, 3%, 4%, 5%, 10%, 15%, 20%, 25% or more, compared to the amount of the same animal feed required by a control to reach the same target weight. In that context, a target body weight of a broiler chicken may be, may be up to, or may be at least, about 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g, 2600 g, 2700 g, 2800 g, 2900 g, 3000 g, 3100 g, 3200 g, 3300 g, 3400 g, 3500 g or more. The term "about" in that context may include ±50 g, ±40 g, ±30 g, ±20 g or ±10 g of the stated value.

For example, in the context of the industry standard for rearing a broiler chicken for 42 days, it is typical to provide each chicken with total of 5.2 kg of feed throughout its life (a mean average of 123.8 g of feed per day of life). In such a situation, one embodiment, involves feeding the chicken a total amount of chicken feed that is reduced from 5.2 kg, and/or reduced from a mean average of 123.8 g feed per day, by 0.01%, 0.05%, 0.1%, 0.2%, 0.3%, 0.4%, 0.5%, 1%, 2%, 3%, 4%, 5%, 10%, 15%, 20%, 25% or more, during its rearing.

Accordingly, the disclosed methods and uses may further comprise the step of rearing the animal to permit enhanced growth.

A further embodiment provides a method of preventing or reducing the colonization of the gastrointestinal tract of an animal (such as an animal described above) with *Campylobacter* and/or other bacterial or microorganisms, by causing the animal to ingest and/or absorb an effective amount of one or more compounds. In particular, it relates to reduction or prevention of colonization of the gastrointestinal tract of poultry or other animals or humans with *Campylobacter*

Accordingly, in a further embodiment, there is provided a method for disinfection of an animal comprising administering to the animal at least one or more compounds having the structure of Formula I in an effective amount to reduce the number of *Campylobacter* and/or other bacterial or microorganisms present in the gastrointestinal tract of the animal.

A further embodiment also provides a method for disinfection of an animal comprising administering to the animal at least one or more compounds below in an effective amount to prevent the *Campylobacter* and/or other bacterial or microorganisms from forming a biofilm in the gastrointestinal tract of the animal or to reduce the amount of biofilm formed by *Campylobacter* and/or other bacterial or microorganisms in the intestinal tract of the animal.

A further embodiment also provides a method for preventing or reducing transmission of *Campylobacter* infection, and/or infection by other bacteria or microorganisms, from one animal to another, for example preventing or reducing spread of *Campylobacter* and/or infection by other bacteria or microorganism, within a flock or herd of animals, for example preventing spread of *Campylobacter* infection and/or infection by other bacteria or microorganisms, within a flock of chickens, including broiler chickens; the method comprising administering to the animals, for example the herd or flock of animals, for example the flock of chickens, one or more compounds having the structure of Formula I in an effective amount to prevent the *Campylobacter* and/or other bacteria or microorganisms, from forming a biofilm in the gastrointestinal tract of the animal or to reduce the amount of biofilm formed by *Campylobacter* and/or other bacteria or microorganisms, in the intestinal tract of the animal.

These methods may allow disinfection, prevention of biofilm formation and reduction of transmission of *Campylobacter* and/or other bacteria or microorganisms, between animals by preventing or reducing adherence of *Campylobacter* and/or other bacteria or microorganisms, of the gastrointestinal tract of the animals. This is advantageous because the fewer *Campylobacter* and/or other bacteria or microorganisms, that are in the gastrointestinal tract of an animal at the time of slaughter, the lower the risk of contamination of meat from the animal with *Campylobacter* and/or other bacteria or microorganisms. The fewer *Campylobacter* and/or other bacteria or microorganisms that are in the gastrointestinal tract of an animal the lower the chance of the *Campylobacter* and/or other bacteria or microorganisms, forming a biofilm in the gastrointestinal tract of the animal. The fewer *Campylobacter* and/or other bacteria or microorganisms, that are in the gastrointestinal tract of an animal, the lower the chance that the *Campylobacter* and/or other bacteria or microorganisms, will spread from one animal to another, for example within a herd or flock of animals.

These methods may also be used to reduce the amount of colonisation of the gastrointestinal tract of any animal with *Campylobacter* and/or other bacteria or microorganisms. It can be particularly advantageous to provide the one or more compounds having the structure of Formula I to animals that will be slaughtered for human consumption. Poultry includes birds that are used for human consumption such as chickens, geese, turkeys, pheasants, and ducks. It is particularly, advantageous to use the compounds to reduce or prevent colonisation of the gastrointestinal tract of poultry, in particular chickens, and more particularly broiler chickens, egg laying chicken and/or breeder chickens, with *Campylobacter* and/or other bacteria or microorganisms because chickens are a leading source of human infection with *Campylobacter*.

The number of *Campylobacter* and/or other bacteria or microorganisms in the gastrointestinal tracts of animals may be reduced by the methods disclosed herein In one embodiment the number of colony forming units (cfu) of *Campylobacter* and/or other bacteria or microorganisms in the gastrointestinal tract of an animal treated with the compounds may be reduced by 10%, by 20%, by 30%, by 40%, by 50%, by 60%, by 70%, by 80%, by 90% or by 100%. In one embodiment *Campylobacter* and/or other bacteria or microorganisms may be substantially eradicated from the gastrointestinal tract of animals treated as disclosed herein.

10,000 cfu of *Campylobacter* are enough for successful chicken colonization. 1,000 cfu of *Campylobacter* are enough to infect a human and cause disease in a human. Therefore, an effective amount of a disclosed compound is enough of the compound to reduce the number of *Campylobacter* and/or other bacteria or microorganisms in the gastrointestinal tract of an animal, or on the surface of the bird, such as the neck skin, to a number that is unlikely to cause infection in humans, such as less than 10,000 cfu, 5,000 cfu, 1,000 cfu, 500 cfu, 400 cfu, 300 cfu, 200 cfu, 100 cfu, 90 cfu, 80 cfu, 70 cfu, 60 cfu, 50 cfu or less. The number of cfu of *Campylobacter* and/or other bacteria or microorganisms that would be ingested by a human if they ate meat from an infected animal may be related to the number of *Campylobacter* and/or other bacteria or microorganisms in the gastrointestinal tract of the animal at the time of slaughter but also depends on other factors such as the amount of contamination of the meat with the contents of the gastrointestinal tract of the animal at the time of slaughter.

An effective amount of the one or more compounds having the structure of Formula I, in this context, may be an amount that is enough of the one or more compounds to prevent colonisation of the gastrointestinal tract of the animal with *Campylobacter* and/or other bacteria or microorganisms.

In one embodiment the one or more compounds having the structure of Formula I, may make *Campylobacter* and/or other bacteria or microorganisms less virulent and less capable of infecting humans even if the total number of *Campylobacter* and/or other bacteria or microorganisms in the gastrointestinal tract does not decrease. In this embodiment administering the compound to an animal may affect the metabolism of *Campylobacter* and/or other bacteria or microorganisms and make them less adaptive to environment (for example, less motile) so that they cannot colonize the gastrointestinal tract and are less likely to be transmitted to other animals or to humans.

An effective amount of a one or more compounds provided to an animal should be enough to provide the required degree of reduction of *Campylobacter* and/or other bacterial or microorganism colonisation. This may depend on the type of compound and/or the size of the animal.

In one embodiment, the one of more compounds may be provided in an animal feed, animal drink, or other compositions in concentration within the range of about 1 μM to about 1M, preferably greater than 10 μM, 20 μM, 30 μM, 40 μM, 50 μM, 60 μM, 70 μM, 80 μM, 90 μM, 100 μM, 110 μM, 120 μM, 130 μM, 140 μM, 150 μM, 160 μM, 170 μM, 180 μM, 190 μM, 200 μM, 250 μM, 300 μM, 350 μM, 500 μM, 1 mM or more.

For example, the concentration of the one or more compounds may be:

(a) up to 1 μM, 2 μM, 3 μM, 4 μM, 5 μM, 10 μM, 15 μM, 20 μM, 25 μM, 30 μM;

(b) within a range selected from the group consisting of from 35 to 335 μM, 40 to 300 μM, 50 to 300 μM, 50 to 250 μM, 50 to 200 μM, 60 to 300 μM, 60 to 250 μM, 60 to 200 μM, 80 to 300 μM, 80 to 250 μM, 80 to 200 μM, 100 to 300 μM, 100 to 250 μM, or 100 to 200 μM; or (c) at least, or about, 345 μM, 350 μM, 360 μM, 370 μM, 380 μM, 390 μM, 400 μM, 450 μM, 0.5 mM, 1 mM, 2 mM or more.

In another embodiment, the concentration may be within a range selected from the group consisting of from about 1 μM to about 1 mM, or about 30 μM to about 0.5 mM, or about 60 μM to about 0.3 mM.

In the case of the animal drink (such as drinking water) or other composition types, optionally, the concentration of the one or more compounds in the composition may be within the range of 0.002 to 15 g/L, or at a level of, up to, or at least, about 0.002 g/L, 0.005 g/L, 0.01 g/L, 0.02 g/L, 0.03 g/L, 0.04 g/L, 0.05 g/L, 0.1 g/L, 0.2 g/L, 0.3 g/L, 0.4 g/L, 0.5 g/L, 1 g/L, 2 g/L, 3 g/L, 4 g/L, 5 g/L, 10 g/L, 15 g/L or 20 g/L In another embodiment, the one of more compounds may be provided in an animal feed, animal drink, or other composition in a unit dosage formulation, and/or at a concentration to deliver up to, or at least, about 1 ng, 10 ng, 50 ng, 100 ng, 500 ng, 1 μg, 10 μg, 50 μg, 100 μg, 500 μg, 1 mg, 10 mg, 100 mg, 500 mg, 1 g, 2 g, 3 g, 4 g, or 5 g of the one or more compounds.

The disclosed methods and uses may further comprise the step of harvesting a product from the reared animal with enhanced growth. The harvested product may be the body or part of the body of the animal. In that case, the harvesting process includes the step of slaughtering the animal and optionally preparing an animal carcass or part thereof as a product, such as a meat product. Accordingly, the harvested body or part of the body of then animal may be a non-food product, a food product, or a precursor of a food product. Carcasses and parts of carcasses may go through a process known as rendering to be made into human and non-human foodstuffs, fats, and other material that can be sold to make commercial products such as cosmetics, paint, cleaners, polishes, glue, soap and ink. Further such products that may be foodstuffs include but are not limited to blood, bone, including bone char, bone meal, etc., broths and stocks created with animal fat, bone, and/or connective tissue, carmine also known as cochineal (food dye), casein (found in milk and cheese), civet oil (food flavoring additive), gelatin, isinglass (which, may, for example be used in clarification of beer and wine), L-cysteine (which may for example used in the production of biscuits and bread), lard, meat (including fish, poultry, and game), and rennet (commonly used in the production of cheese). Meat and meat products may be of particular interest.

In one particularly preferred embodiment, the animal is a chicken, for example, a meat-type chicken such as broiler chicken, or an egg-laying chicken such as a pullet or hen, and the product is harvested from the reared animal. Most preferably, the animal is a meat-type chicken, such as broiler chicken, and the harvested product is a carcass or part of the carcass of the chicken. After slaughter to produce the carcass, it may or may not be further processed, such as to remove one or more items selected from the group consisting of feathers, offal, neck skin, head, legs, and other items, and may produce a whole dressed carcass ready for sale as a meat product, or ready to send onto further processing. In one embodiment the processed carcass may retain the neck or neck skin, or at least 50%, 60%, 70%, 80%, 90% or more thereof as determined either by length or by weight. The average weight of the neck or neck skin may be in the range of 15-25 g. Further processing may include performing a cut-up operation wherein the carcass is cut into individual parts, and may involve deboning (i.e. where the bones are removed from specific parts) to produce items like breast filets or other boneless products.

In one exemplary embodiment, a process for the slaughter and/or processing of a chicken may include any one or more of the following methodological step: (i) birds arrive at processing plant, typically in plastic crates; (ii) blue light is used to calm the birds; (iii) birds are hung; (iv) birds enter a stun tank; (v) birds are slaughtered using a neck bleed, optionally with a delay stand for bleeding out the birds; (vi) birds skin and/or feathers are heated, for example with water, to loosen pores holding the feathers; (vii) feathers are removed, e.g. using rubber fingers; (viii) an inspection is conducted to remove any birds failing a quality control assessment; (ix) drill or other implement is used to create a hole in the carcass and remove anus; (x) removal of the intestines and other internal organs, typically via the previously-created hole; (xi) optionally, the production line splits for the production of whole chickens and chicken parts; (xii) chicken parts may be cut up using an automated process and through manual labor (workers slicing); optionally including the separate liver, kidney and/or hearts; (xiii) the whole chicken carcass and/or chicken parts may be directly labeled on the floor of the processing plant, ready for the grocery store (further optionally including pricing) so the product can go directly on the store shelf.

It will be appreciated that alternative methods of stunning the bird are available, and can be substituted for the method indicated in the foregoing method and/or used more generally in accordance the methods and uses disclosed herein. Exemplary alternative methods of stunning the bird include, for example, controlled atmosphere stunning, controlled atmosphere killing, Bi-phasic $CO_2$, and controlled slow decompression.

Alternatively, the bird may not be stunned prior to slaughter, e.g. in the case of the production of a meat product in accordance with religious laws, such as Halal, Qurrbani/Udhia, and/or Shechita slaughter laws.

The processing of the carcass may be conducted at adequately low refrigeration temperatures, such as around 1, 2, 3, 4 or 5° C.

Accordingly, following the processing of the animal carcass and/or the production of parts thereof, the carcass or part thereof may be further processed to produce a value added product, and this may include one or more steps required to prepare a consumer-ready product, which may include the addition of any one or more of seasoning, breading, sauces, and marinating, as well as special packaging to meet market demands for convenient products.

Additionally, or alternatively, the harvested product may, for example, be a by-product of the animal, such as milk, eggs, wool, hair, feathers, or litter or other feacal matter and can be collected from the animal without the need to slaughter the animal. Such harvested products may then be further processed and converted into other products. For example, in the context of milk, then further dairy products can be produced (such as butter, cheese, curd, yoghurt, whey, milk powder, sour cream, dips and other cultured dairy foods, frozen desserts such as ice cream cakes other frozen desserts made with dairy ingredients). In the context of eggs, then further products (in particular food products) containing or produced with the whole or part of the collected eggs can be produced. In the context of wool, hair or feathers, then it may, for example, be possible to produce fibers or fabrics, products containing wool, hair or feathers (such as, stuffed products), or products may be chemical or enzymatic processing of the wool, hair or feathers. For example, amino acids can be produced as a degradation product from wool, hair or feathers. Chicken litter can include a mixture of feces, wasted feeds, bedding materials, and feathers can be recycled or composted and then spread on arable land as a low cost organic fertilizer.

Any and all steps within the entire process of animal rearing, animal harvesting, animal slaughter, carcass processes, animal product production, food production, wrapping, labelling, shipping, stocking and selling may benefit from the application of a surface disinfection or coating as discussed further below. For example, areas for rearing animals may contain one or more disinfected surfaces achieved using the methods, uses and compositions disclosed herein. Containers for transporting animals, apparatus used in the slaughter of animals, apparatus used in the processing and/or labelling of an animal carcass, or a part thereof may contain one or more disinfected surfaces achieved using the methods, uses and compositions disclosed herein. The animal product, including a carcass, a meat product, or any other animal product produced as disclosed herein may be disinfected using the methods, uses and compositions disclosed herein. Packing, containers and/or wrapping for containing an animal product, including a carcass, a meat product, or any other animal product may be disinfected using the methods, uses and compositions disclosed herein. These combinations of the approaches all form optional embodiments of the first aspect.

Also provided are products produced by, and/or harvested from, animals treated as disclosed herein, including any and all products discussed above, and downstream products including or produced therefrom.

For example, a meat or meat product produced in accordance with the disclosed methods is provided. For example, it can provide a carcass or part thereof that is of a greater weight than a standard carcass or part thereof, or is from an animal that is younger than a control. Additionally, or alternatively, carcass or part thereof, or any other product obtained from the animal may have a reduced level of microbial (such as bacterial, including *Campylobacter*) infection or colonization and/or a reduced incidence of biofilms therein, compared to a control.

It will be appreciated that the foregoing methods and uses for enhancing the growth of an animal may also be applied to humans, for example to increase the growth of humans (such as an aid to developing body mass) and/or improve the efficiency or FCR with which humans digest food. This could, for example, have applications for military personnel in helping to reduce the burden of carrying food and/or assist in the instance of food shortages by increasing the dietary benefit of the available food.

B. Potentiating the Effect of Antibiotics and Other Antimicrobial Agents, and Addressing Antibiotic Resistance It has been discovered that the compounds are particularly useful in treating or preventing infection by antibiotic-resistant microorganisms. The compounds may be administered in order to cause microorganisms to lose their resistance to antibiotics or to increase the sensitivity of microorganism to antimicrobial agents, to potentiate the effect of antibiotics and other antimicrobial agents, and to address antimicrobial and antibiotic resistance.

In this embodiment the one or more compounds are selected from the group consisting of a complex of an amino acid with Fe III, and a complex of an α-hydroxyacid with Fe III, or salts and/or hydrates thereof. In particularly preferred options the one or more compounds may, or may not, be selected from any one or more of the group consisting of ferric lactate, ferric citrate, ferric tartrate, a complex of quinic acid with Fe III, a complex of L-tyrosine with Fe III), a complex of L-DOPA with Fe III, and a complex of L-phenylalanine with Fe III.

In a particularly preferred embodiment, the compounds having the structure of Formula I may be used in combination with antimicrobial agents to treat or prevent infection by antibiotic resistant bacteria including *Streptococcus pneumoniae, Campylobacter, Neisseria gonorrhoeae, Salmonella* (including drug-resistant non-typhoidal *Salmonella* and drug-resistant *Salmonella* serotype *typhi*), Methicillin-resistant *Staphylococcus aureus* (MRSA), *Shigella*, Vancomycin-resistant *Enterococcus* (VRE), Vancomycin-resistant *Staphylococcus aureus* (VRSA), Erythromycin-resistant Group A *Streptococcus*, Clindamycin-resistant Group B *Streptococcus*, Carbapenem-resistant Enterobacteriaceae (CRE), drug-resistant tuberculosis, Extended spectrum Enterobacteriaceae (ESBL), multidrug-resistant *Acinetobacter* (including MRAB), *Clostridium difficile*, Enteropathogenic *E. coli* (EPEC), *Pseudomonas aeruginosa*, and Uropathogenic *E. coli* (UPEC). In another preferred embodiment. In another embodiment, the compounds may be used in combination with antimicrobial agents to treat or prevent infection by antibiotic resistant bacteria including *S. epidermidis, E. faecalis, E. coli, S. aureus*, Enteropathogenic *Escherichia coli* (EPEC), Uropathogenic *Escherichia coli* (UPEC), *Pseudomonas, Streptococcus anginosus, Salmonella*, including *Salmonella Enteritidis* and *Salmonella Typhimurium, Mycoplasma, Eimeria, Enterococci, Brachyspira*, and *Clostridium perfringen*. In a preferred embodiment, the compounds and antimicrobial agents may be administered as a pharmaceutical composition or feed additive.

Antibiotic-resistant microorganisms (and other microorganisms resistant to other forms of anti-microbial agent) may be treated with the one or more compounds and one or more antibiotics or other anti-microbial agents separately, sequentially or simultaneously. The one or more compounds are preferably administered at the same time as the one or more antibiotics or other anti-microbial agents, or preferably such that the compounds and antibiotic(s) are present at the same time. (The compounds and the antibiotics/anti-microbial agents may therefore also be administered sequentially.)

The compounds may also be used in combination with antibiotics or other anti-microbial agents to allow smaller doses of antibiotic or other anti-microbial agents to be used to treat not only antibiotic-resistant microorganisms (and/or other microorganisms resistant to other forms of anti-microbial agent), but also for the treatment of microorganisms that are not resistant to antibiotics or other anti-microbial agents. For example, the compounds could be administered to poultry prophylactically so that a lower dose of antibiotic and/or other anti-microbial agent was required to treat the birds in the event they become infected.

Pharmaceutical or veterinary product, a medical device or a dietary product, is provided, wherein the product comprises one or more compounds for use in a method of treatment or prophylaxis of a microbial infection or colonization in a patient or animal, preferably wherein, in use, the pharmaceutical or veterinary product, medical device or dietary product is administered to the patient or animal separately, simultaneously, or sequentially with the administration of one or more antimicrobials and/or antibiotics.

Likewise, one or more antimicrobials and/or antibiotics, for use in a method of treatment or prophylaxis of a microbial infection or colonization in a patient or animal are provided, preferably wherein, in use, the pharmaceutical or veterinary product, medical device or dietary product is administered to the patient or animal separately, simultaneously, or sequentially with the administration of a pharmaceutical or veterinary product, a medical device or a dietary product, wherein the product comprises one or more compounds.

The microbial infection or colonization in a patient or animal may, for example, be pathogenic or non-pathogenic microbes. Non-pathogenic microbes can, for example, cause colonization of a host without causing or producing any disease or disorder of the host. The microbial infection or colonization may be prokaryotic or eukaryotic, or a combination of both. Examples of prokaryotic microbes include bacteria and archaea. Examples of eukaryotic microbes include protists (such as algae, and slime-molds), fungi, multicellular micro-animals and plants including green algaes.

Non-limiting examples of bacteria include gram positive bacteria, gram negative bacteria, biofilm-forming bacteria, extracellular bacteria, intracellular bacteria (including facultative and obligate intracellular bacteria), aerobic bacteria, and anaerobic bacteria. Some bacterial genera of interest, without limitation, include *Bacillus, Bartonella, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yersinia*. Some bacterial species of interest, without limitation, include *Bacillus anthracia, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumonia, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Pseudomonas aeruginosa, Rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumonia, Streptococcus pyogenes, Treponema pallidum, Ureaplasma urealyticum, Vibrio cholera, Yersinia pestis, Yersinia enterocolitica, Yersinia pseudotuberculosis*.

The treatment or prophylaxis as disclosed herein may be directed to one or more microorganism that have resistance or increased tolerance to one or more antimicrobial agents. For example, the one or microorganisms may be, or include, one or more antibiotic-resistant bacteria.

Antimicrobial resistance can include the meaning of resistance of a microorganism to an antimicrobial drug that was originally effective for treatment of infections caused by it. Resistant microorganisms are able to withstand attack by antimicrobial drugs, such as antibacterial drugs (e.g. antibiotics), antifungals, antivirals, and antimalarials, so that standard treatments become ineffective and infections persist, increasing the risk of spread to others. The evolution of resistant strains is a natural phenomenon that occurs when microorganisms replicate themselves erroneously or when resistant traits are exchanged between them. The use and misuse of antimicrobial drugs accelerates the emergence of drug-resistant strains. Poor infection control practices, inadequate sanitary conditions and inappropriate food-handling encourage the further spread of antimicrobial resistance.

In one embodiment the microorganism is an antibiotic-resistant microorganism selected from the group consisting of a gram positive bacterium, a gram negative bacterium, a biofilm-forming bacterium, *Streptococcus pneumoniae, Campylobacter, Neisseria gonorrhoeae, Salmonella* (including drug-resistant non-typhoidal *Salmonella* and drug-resistant *Salmonella* serotype *typhi*), Methicillin-resistant *Staphylococcus aureus* (MRSA), *Shigella*, Vancomycin-resistant *Enterococcus* (VRE), Vancomycin-resistant *Staphylococcus aureus* (VRSA), Erythromycin-resistant Group A *Streptococcus*, Clindamycin-resistant Group B *Streptococcus*, Carbapenem-resistant Enterobacteriaceae (CRE), drug-resistant tuberculosis, Extended spectrum Enterobacteriaceae (ESBL), multidrug-resistant *Acinetobacter* (including MRAB), *Clostridium difficile*, Enteropathogenic *E. coli* (EPEC), *Pseudomonas aeruginosa, H. pylori, Streptococcus anginosus* and Uropathogenic *E. coli* (UPEC).

The compounds can also be used to increase the sensitivity of non-resistant microorganisms to antimicrobial agents, and thereby provide for a treatment that uses lower dosages of antimicrobial agents, and/or shorter treatment durations with antimicrobial agents, and/or more effective treatment outcomes with antimicrobial agents.

Accordingly, in a further embodiment the method, or the product for use, is for potentiating the antimicrobial (including antibiotic) effect of the separately, simultaneously, or sequentially administered one or more antimicrobial agents (including one or more antibiotics). For example, in a further embodiment, the amount of the separately, simultaneously, or sequentially administered one or more antimicrobial agents (including one or more antibiotics) may be less than a therapeutically effective or therapeutically optimal dose of the one or more antimicrobial agents (including one or more antibiotics) when administered to the patient or animal that is not in receipt of the product. In another embodiment, the amount of the separately, simultaneously, or sequentially administered one or more antimicrobial agents (including one or more antibiotics) may be 5%, 10%, 15%, 20%, 30%, 40%, 50%, 60%, 70%, 80% or more, less than a therapeutically effective or therapeutically optimal dose of the one or more antibiotics when administered to the patient or animal that is not in receipt of the product. In another embodiment, the treatment duration of the patient receiving the treatment or prophylaxis of the second embodiment may be 5%, 10%, 15%, 20%, 30%, 40%, 50%, 60%, 70%, 80% or more, less than the treatment duration required when the patient or animal is not in receipt of the product.

In one embodiment, at least one, or all, of the one or more antimicrobial agents is/are an antibiotic. The one or more antibiotics may, for example, be selected from the group consisting of aminoglycosides, ansaycins, carbapenems, cephalosporins, glycopeptides, lincosamides, lipopeptides, macrolides, monobactams, nitrofurans, oxazolidinones, penicillins, polypeptides, quinolones/fluoroquinolone, sulfonamides, tetracyclines, clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim; and combinations thereof.

The pharmaceutical or veterinary product may include one or more excipients, as a parenteral formulation, including a controlled release formulation, or injectable or implantable formulation. The pharmaceutical or veterinary product may be presented as a enteral formulation, including a controlled release enteral formulation, including extended release dosage forms and delayed release dosage forms. The pharmaceutical or veterinary product may be presented as a topical formulation, including as an emulsion, lotion, cream, ointment, gel, or foam.

In another embodiment, the product comprising the one or more compounds is a medical device. The device may or may not additionally include the one or more antimicrobial agents (in the embodiment that it does not, then the device and microbial agent are intended to be administered to the subject in separate compositions, either separately, simultaneously or sequentially). Medical devices can include, without limitation, wound dressings, medical implants, tubing and other surface medical devices, such as urinary catheter, stents, mucous extraction catheter, suction catheter, umbilical cannula, contact lenses, intrauterine devices, intravaginal and intraintestinal devices, endotracheal tubes, bronchoscopes, dental prostheses and orthodontic devices, surgical instruments, dental instruments, tubing, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. Devices may include electrodes, external prostheses, fixation tapes, compression bandages, and monitors of various types. Medical devices also include any device that may be placed at the insertion or implantation site such as the skin near the insertion or implantation site, and which include at least one surface which is susceptible to colonization by biofilm embedded microorganisms. In one specific embodiment, a composition is integrated into an adhesive, such as tape, thereby providing an adhesive, which can present and/or deliver the one or more compounds on at least one surface of the adhesive. In a particularly preferred embodiment the following devices may comprise, include and/or be coated with the compounds: catheters, including central venous catheters, urinary catheters, dialysis catheters, and indwelling catheters (for example, catheters for hemodialysis and for administration of chemotherapeutic agents), cardiac implants including mechanical heart valves, stents, ventricular assist devices, pacemakers, cardiac rhythm management (CRM) devices, cardiac resynchronization therapy devices (CRTs), and implantable cardioverter defibrillators (ICDs), synthetic vascular grafts, arteriovascular shunts, cerebral spinal fluid shunts, cochlear devices, prosthetic joints, orthopedic implants, internal fixation devices, bone cements, percutaneous sutures, surgical mesh and surgical patches including hernia repair meshes and patches, breast reconstruction meshes and patches, meshes and patches for breast and face lifts, slings, and meshes and patches for pelvic floor reconstruction, tracheal and ventilator tubing, wound dressings, biological implants (including allografts, xenografts and autografts), penile implants, intrauterine devices, endotracheal tubes, and contact lenses.

In another embodiment, the product comprising the one or more compounds is a dietary product. The dietary product may or may not additionally include one or more antimicrobial agents. Dietary products can include, for example, food stuffs, dietary supplements, drinks, and any other compositions taken orally, which incorporate the one or more.

The one or more compounds are selected from the group consisting of a complex of an α-hydroxyacid with Fe III, or salts and/or hydrates thereof.

A further embodiment provides a method for the preparation of a product per se, such as a pharmaceutical or veterinary product, a medical device or a dietary product, that is suitable for use in accordance with the foregoing methods and uses disclosed herein. The method may include the step of mixing, spraying, coating or blending the one or more compounds with the materials forming the formulation or device.

The administration of Components 1 and 2, one of which is an iron complex as described herein and the other an antimicrobial, may be temporally separated by up to, about, or at least, 10 seconds, 20 seconds, 30 seconds, 40 seconds, 50 seconds, 1 minute, 5 minutes 10 minutes, 20 minutes, 30 minutes 40 minutes 50 minutes 1 hour, 2 hours, 3 hours, 4 hours 5 hours, 6 hours, 7 hours 8 hours, 9 hours, 10 hours, 12 hours, 14 hours, 16 hours, 18 hours, 20 hours 22 hours 1 day, 2 days, 3 days, 4 days, 5 days, 6 days, 1 week, 2 weeks, 3 weeks, 1 month or more. Sequential administration includes the meaning of repeated and alternating administrations of Components 1 and 2 (in either order), in which the administration of either or both components may be repeated any number of times, such as twice, three times, four times, five times, 10 times, 20 times, 30 times or more.

Repeated administration of either, or both components, whether administered simultaneously, separately or sequentially, may occur as often as is therapeutically necessary, and can include continuous administration (e.g. by intravenous infusion), of administration up to, about, or at least, every 1, 2, 3, 4, 5, 6, 7, 8, 9, 10, 12, 13, 14, 15, 16, 17, 18, 19, 20, 21, 22, 24 or 24 hours, every 1, 2, 3, 4, 5, 6, 7 days, or every 1, 2, 3, 4 or more weeks, throughout the period of treatment.

The period of treatment is typically selected to achieve a therapeutically or prophylactically effective outcome, and will be judged accordingly, by the skilled professional. Example of some suitable periods for treatment can include 1, 2, 3, 4, 5, 6, 7, 8, 9, 10, 11, 12, 13 or 14 days, about 1, 2, 3, or 4 weeks, or longer.

C. Inhibition of Formation, and Treatment of Preformed, Biofilms

A third aspect of the present disclosure is, based on the surprising finding that the compounds have a broad range of action in treating and dispersing pre-existing biofilms, and inhibiting the development of biofilms, created by a wide range of bacterial and other microbial sources, and that this action is effective in a diverse array of environments.

Accordingly, this aspect provides a method of inhibiting biofilm buildup, and/or disrupting a pre-existing biofilm, in or on a subject or article in need thereof, the method comprising administering to the subject or article an effective amount of one or more compounds having the structure of Formula I.

In one embodiment, the one or more compounds or a salt and/or hydrate thereof, or a functional variant thereof, bind to major outer membrane proteins (MOMPs) or FlaA of *Campylobacter*, a synthetic human histo-blood group antigen, a mimetic of human histo-blood group antigen or a synthetic sugar. Particularly preferred compounds include Fe-Lac, Fe-Cit, Fe-Tart, or Fe-malate.

1. Organisms to be Treated, Inhibited, or Killed

"Biofilm" as used herein refers any group of microorganisms in which cells adhere to a surface in a complex structure.

Formation of a biofilm begins with the attachment of free-floating microorganisms to a surface. These first colonists adhere to the surface initially through weak, reversible adhesion via van der Waals forces. If the colonists are not immediately separated from the surface, they can anchor themselves more permanently using cell adhesion structures such as pili. Some species are not able to attach to a surface on their own but are sometimes able to anchor themselves to the matrix or directly to earlier colonists. It is during this colonization that the cells are able to communicate via quorum sensing. Once colonization has begun, the biofilm grows through a combination of cell division and recruitment. Polysaccharide matrices typically enclose bacterial biofilms. The final stage of biofilm formation is known as dispersion, and is the stage in which the biofilm is established and may only change in shape and size.

In one embodiment, a biofilm may comprise, consist essentially of, or consist of, microbial cells growing in a biofilm that are physiologically distinct from planktonic cells of the same organism, which, by contrast, are single-cells. Optionally, a biofilm may comprise, consist essentially of, or consist of, one species or strain of bacterial cell.

In an alternative option, a biofilm may comprise, consist essentially of, or consist of, more than one species or strains of bacterial cell, such as up to at least 2, 3, 4, 5, 6, 7, 8, 9, 10, 15, 20, 30, 40, 50, 60 70, 80, 90, 100, 150, 200, 250, 300, 350, 400, 450, 500, 600, 700, 800, 900, 1000 or more different species or strains of bacterial cell.

The bacterial species or strains in biofilms can include bacteria selected from one or more of gram negative, gram positive, aerobic and anaerobic bacteria and/or archaea.

Accordingly, compositions and methods for inhibiting, reducing, or removing biofilm forming bacteria and bacterial infections are provided.

The biofilm forming bacteria to be inhibited, reduced, removed, or treated may be gram-negative and/or gram-positive bacteria, such as *Pseudomonas aeruginosa, Campylobacter jejuni, Helicobacter pylori, Escherichia coli*, Enteropathogenic *Escherichia coli* (EPEC), Uropathogenic *Escherichia coli* (UPEC), *Staphylococcus epidermidis, Staphylococcus aureus*, and *Enterococcus faecalis*.

The following are representative organisms that can be killed or growth inhibited, or their ability to produce or maintain biofilms degraded, reduced, inhibited or prevented in accordance disclosed methods.

One form of biofilm of particular interest in certain embodiments is biofilm that forms dental plaque. The biofilm in dental plaque typically comprises a variety of microbial organisms, including both aerobic and anaerobic bacteria, and typically includes over 700 different species of bacteria and archaea. Dental plaque biofilms are responsible for many of the diseases common to the oral cavity including dental caries, periodontitis, gingivitis, and the less common peri-implantitis (similar to periodontitis, but with dental implants), however biofilms can be present on healthy teeth as well.

Accordingly also provided are methods and uses for preventing or inhibiting the formation of, for treating, or for reversing or removing conditions including dental plaque, dental caries, periodontitis, gingivitis, and the less common peri-implantitis. The method or use may comprise administering one or more of the disclosed compositions to the mouth of a subject, thereby to achieve the intended effect.

For example, dental products may present the buccal cavity or teeth with one or more of the compounds at a concentration within the range of about 1 µM to about 1M, such as about, or up to, 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM, 200 µM, 210 µM, 220 µM, 230 µM, 240 µM, 250 µM, 260 µM, 270 µM, 280 µM, 290 µM, 300 µM, 310 µM, 320 µM, 330 µM, 340 µM, 350 µM, 360 µM, 370 µM, 380 µM, 390 µM, 400 µM, 410 µM, 420 µM, 430 µM, 440 µM, 450 µM, 460 µM, 470 µM, 480 µM, 490 µM, 500 µM, 510 µM, 520 µM, 530 µM, 540 µM, 550 µM, 560 µM, 570 µM, 580 µM, 590 µM, 600 µM, 610 µM, 620 µM, 630 µM, 640 µM, 650 µM, 660 µM, 670 µM, 680 µM, 690 µM, 700 µM, 710 µM, 720 µM, 730 µM, 740 µM, 750 µM, 760 µM, 770 µM, 780 µM, 790 µM, 800 µM, 810 µM, 820 µM, 830 µM, 840 µM, 850 µM, 860 µM, 870 µM, 880 µM, 890 µM, 900 µM, 910 µM, 920 µM, 930 µM, 940 µM, 950 µM, 960 µM, 970 µM, 980 µM, 990 µM, 1 mM, 2 mM, 3 mM, 4 mM, 5 mM, 6 mM, 7 mM, 8 mM, 9 mM, 10 mM, 15 mM, 20 mM 25 mM, 30 mM, 35 mM, 40 mM, 45 mM, 50 mM, 60 mM, 70 mM, 80 mM, 90 mM, 100 mM, 150 mM, 200 mM, 250 mM, 300 mM, 350 mM, 400 mM, 450 mM, 500 mM, 600 mM, 700 mM, 800 mM, 900 mM, 1M or more. Optionally, the concentration may be:

(a) up to 1 µM, 2 µM, 3 µM, 4 µM, 5 µM, 10 µM, 15 µM, 20 µM, 25 µM, 30 µM;

(b) within a range selected from the group consisting of from 35 to 335 µM, 40 to 300 µM, 50 to 300 µM, 50 to 250 µM, 50 to 200 µM, 60 to 300 µM, 60 to 250 µM, 60 to 200 µM, 80 to 300 µM, 80 to 250 µM, 80 to 200 µM, 100 to 300 µM, 100 to 250 µM, or 100 to 200 µM; or (c) at least, or about, 345 µM, 350 µM, 360 µM, 370 µM, 380 µM, 390 µM, 400 µM, 450 µM, 0.5 mM, 1 mM, 2 mM or more.

Optionally the concentration of the one or more compounds may be within a range selected from the group consisting of from about 1 µM to about 1 mM, or about 30 µM to about 0.5 mM, or about 60 µM to about 0.4 mM.

In one embodiment, the biofilm is biofilm on medical devices, including contact lenses. Biofilms on contact lenses may, for example, comprise, consist essentially of, or consist of one or more bacteria selected from *Archromobacter, Delftia, Staphylococcus, Stenotrophomonas,* and *Streptococci* species, and *Pseudomonas aeruginosa.*

In another embodiment, the biofilm is biofilms formed on the skin, for example biofilms which comprise, consist essentially of, or consist of *Propionibacterium acnes*. Accordingly, methods and uses for preventing or inhibiting the formation of, for treating, or for reversing or removing acne and other microbially-induced skin conditions, including recalcitrant and/or anti-biotic resistant conditions, are provided, the method or use comprising the topical administration of a composition as disclosed further herein to the skin of a subject, thereby to achieve the intended effect.

Additional examples of biofilms contemplated herein include biofilms that comprise, consist essentially of, or consist of, epsilon proteobacteria class, such as the spirilloid *Wolinella* spp., *Helicobacter* spp., and most particularly *Campylobacter* spp. Many other types of biofilms are contemplated, further examples of which are discussed in further sections of this application.

*Campylobacter* are gram negative, spiral rod shaped bacteria with a single flagellum at one or both poles. They belong to the epsilon proteobacteria class and are closely related to *Helicobacter* and *Wolinella*. At least a dozen species of *Campylobacter* have been implicated in human disease, with *C. jejuni* and *C. coli* the most common.

*Campylobacter jejuni* is the major cause of human bacterial gastroenteritis (Pearson, et al., *Appl Environ Microbiol.,* 59:987-996 (1993)). The four major sources of infection are raw meat (particularly poultry), untreated water, raw milk, and pets (Humphrey, et al., *J Appl Bacteriol.* 61:125-132. (1986) and Skirrow, *Int J Food Microbiol.,* 12:9-16 (1991)). It has also been suggested that, although not universally the case (Humphrey, et al., *Public Health Lab Serv Microbiol Digest.,* 13:86-88.91996), Jacobs-Reitsma, et al., *Epidemiol Infect.,* 114:413-421 (1995), and Lindblom, et al., *J Hyg.,* 96:385-391 (1986)), survival in the water systems of animal husbandry facilities and animal-processing units promotes infection in animals and cross-contamination of animal carcasses (Humphrey, et al., *Epidemiol Infect.,* 98:263-269 (1987), Kazwala, et al., Vet Rec. 1990; 126:305-306. (1990) and, Pearson, et al., *Appl Environ Microbiol.,* 59:987-996 (1993)). Thus, the survival of *C. jejuni* in aquatic environments is important both directly and indirectly in the causation of human disease.

*Campylobacter* spp. have outer membrane proteins (OMPs) (Buchanan, *Curr. Opin. Struc. Biol.,* 9(40:455-461 (1999); Huyer, et al., *FEMS Microbiol. Lett.,* 37(3):247-250 (1986)]. The major outer membrane proteins (MOMPs) have unique structural features, and function as porins which are helpful for linking up the bacteria and their environment. *Campylobacter* spp. possess polar flagella which provide the necessary motility for intestinal colonization. The flagellin gene of *Campylobacter* has two similar copies: flaA and flaB. The length of coding regions for the flaA and flaB sequences are both around 1.7 kilobases, and flaA and flaB sequences locate about 180 bases apart from each other (Meinersmann, et al., *Microbiology,* 146(9):2283 (2000)).

In one embodiment the disclosed compositions bind to major outer membrane proteins (MOMPs) or FlaA of *Campylobacter* and prevent the bound MOMPs and bound FlaA from binding or associating with their ligands on: other *Campylobacter* bacteria; other species of bacteria; biofilm or biofilm components; or to surfaces. By binding to the MOMPs and FlaA, the compounds inhibit the bacteria from binding to surfaces or each other to produce biofilm. The inhibition of binding can be accomplished by interfering with the binding of natural ligands of MOMPs or FlaA or by physically inhibiting the association of the bacteria expressing MOMPs or FlaA to other organisms or surfaces.

In another embodiment, the disclosed compositions also bind to the MOMP protein of *Campylobacter* when MOMP has been mutated to prevent O-glycosylation by mutation of Thr-268 to glycine to form MOMP-T (also referred to as $MOMP^{T268G}$). Expression of the $MOMP^{T268G}$ protein has been found to increase 10-fold compared with wildtype. Treatment of the $MOMP^{T268G}$ strain with the compositions does not impact planktonic growth, but does partially inhibit biofilm formation demonstrating the compositions bind to the non-glycosylated MOMP with lower affinity.

Expression of the $MOMP^{T268G}$ protein has been found to increase 10-fold compared with wildtype. Regardless of whether MOMP is glycosylated or not, the compositions disclosed herein are still effective against mixed populations of glycosylated and non-glycosylated *Campylobacter*. In a mixed population of glycosylated and non-glycosylated forms, the wildtype glycosylated form of *Campylobacter* greatly outcompetes the mutant non-glycosylated form, and over time the non-glycosylated bacteria disappear and the glycosylated bacteria become the only bacteria present.

Biofilms are usually found on solid substrates submerged in or exposed to an aqueous solution, although they can form as floating mats on liquid surfaces. Biofilms can form on a myriad of surfaces. For example, biofilms can grow in showers very easily since they provide a moist and warm environment for the biofilm to thrive. Biofilms can form inside water and sewage pipes and cause clogging and corrosion. Biofilms on floors and counters can make sanitation difficult in food preparation areas. Biofilms can form in cooling- or heating-water systems and are known to reduce heat transfer in these systems One method, or use, includes administering an effective amount of the one or more compounds of this application to a subject in need thereof, to inhibit biofilm formations, or alternatively, to reduce and/or remove biofilm formation. The one or more compounds may be administered alone, or in combination with an antimicrobial agent, such as an antibiotic.

In certain embodiments, in the context of the treatment of subjects (such as humans or animals) it may be desirable to provide continuous delivery of one or more compounds to a subject in need thereof. For intravenous or intra-arterial routes, this can be accomplished using drip systems, such as by intravenous administration. For topical applications, repeated application can be done or a patch can be used to provide continuous administration of the compounds over an extended period of time. For example, the compounds may be delivered to a chronic wound from a wound dressing. The dressing may also contain one or more antibiotics, and if necessary the wound dressing may be changed frequently. The compounds may also be delivered in a conjugated form (for example, as shown in FIGS. 15A-C and FIGS. 16A and B) so that they are immobilized on a surface.

In other embodiments, the method includes contacting a surface with an effective amount of the compounds, to inhibit biofilm buildup, reduce built up biofilm, and/or remove built up biofilm. "Contacting" includes, but is not limited to, touching, impregnating, compounding, mixing, integrating, coating, spraying, dipping, flushing, irrigating, and wiping. In certain embodiments, it may be desirable to provide continuous delivery of one or more compounds to the surface or system being treated. The compositions can be used to coat, impregnate, flush, or rinse a surface of tubing or a medical device, especially an insertable medical device. Tubing includes, but is not limited to, disposable, permanent, and indwelling catheters, long term urinary devices, tissue bonding urinary devices, wound drain tubes, ventricular catheters, endotracheal tubes, breathing tubes, feeding tubes, dairy lines, oil and gas pipeline and drinking water lines. When an object is tubing (e.g., dental unit waterline, a dairy line, a food and beverage processing line, etc.), a composition may be poured into the tubing and both ends of the tubing clamped such that the composition is retained within the lumen of the tubing. The tubing is then allowed to remain filled with the composition for a period of time sufficient to remove substantially all of the microorganisms from at least one surface of the object, generally, for at least about 1 minute to about 48 hours. Alternatively, tubing may be flushed by pouring a composition into the lumen of the tubing for an amount of time sufficient to prevent substantial growth of all biofilm embedded microorganisms. Such flushing may be required only once, or may be required at regular intervals over the lifetime of use of the tubing. Concentrations of active components in a composition may vary as desired or necessary to decrease the amount of time the composition is in contact with a medical device.

The methods allow disinfection, inhibition, or prevention of biofilm formation on the surfaces being treated and reduction of transmission of biofilm forming microorganisms from the surface to another surface. The number of the bacterial colony forming units (cfu) on the surface being treated with the compounds may be reduced by 50%, by 60%, by 70%, by 80%, by 90% or by 100%, or, the buildup of bacterial colony forming units on the treated surface may be reduced by 50%, by 60%, by 70%, by 80%, by 90% or by 100%.

In one embodiment, compositions and articles, including but not limited to pharmaceutical and veterinary compositions, food or feed additive compositions, and dental products including chews may be prepared from the one or more compounds as defined above, optionally formulated and/or used in combination with one or more antibiotics or other anti-microbial agents, and these compositions may further be used for the treatment or prophylaxis of a microbial infection or biofilm formed by bacteria or other microorganisms, including one or more of the following: *S. epidermidis, E. faecalis, E. coli, S. aureus* including Vancomycin-resistant *Staphylococcus aureus* (VRSA) and Methicillin-resistant *Staphylococcus aureus* (MRSA), Enteropathogenic *Escherichia coli* (EPEC), Uropathogenic *Escherichia coli* (UPEC), *Pseudomonas, Streptococcus pneumoniae, Streptococcus anginosus, Neisseria gonorrhoeae, Salmonella* (including drug-resistant non-typhoidal, *Salmonella* including drug-resistant *Salmonella* serotype *typhi, Salmonella Enteritidis, Salmonella Typhimurium, Mycoplasma, Eimeria, Enterococci, Shigella*, Vancomycin-resistant *Enterococcus* (VRE), Erythromycin-resistant Group A *Streptococcus*, Clindamycin-resistant Group B *Streptococcus*, Carbapenem-resistant Enterobacteriaceae (CRE), drug-resistant tuberculosis, Extended spectrum Enterobacteriaceae (ESBL), multidrug-resistant *Acinetobacter* (including MRAB), *Clostridium difficile, Enteropathogenic E. coli* (EPEC), *Pseudomonas aeruginosa, Brachyspira, Propionibacterium acnes*, and *Clostridium perfringen.*

2. Methods of Administration

In one embodiment, the compounds and formulations, derivatives thereof and combinations thereof and be administered topically to a subject in need thereof in an effective amount to prevent or treat a microbial infection, by inhibiting buildup of biofilm or to reduce and/or remove built up biofilm.

Any suitable topical formulation can be used, for example as described in Section III.C.3 of this application, below, including emulsions (such as those described in section III.C.3(a)), lotions (such as those described in section III.C.3 (b)), creams (such as those as described in section III.C.3 (c)), ointments (such as those described in section III.C.3 (d)), gels (such as those described in section III.C.3(e)), or foams (such as those described in section III.C.3(f)).

The compositions may be used alone or in combination with known antimicrobial agents, such as those described further below in section III.B of this application.

The compositions are useful for treating topical conditions caused by biofilm buildup by microorganisms including, but not limited to gram-negative and gram-positive bacteria, including *Staphylococcus* (including, but not limited to *S. aureus* and *Staphylococcus epidermidis*), *Pseudomonas, E. coli., Streptococcus pyogenes* (Reviewed in Nusbaum, et al., *Skin Therapy Lett.*, 17(7):1-5 (2012)), *Propionibacterium acnes* and *Streptococcus anginosus.*

In some embodiments the compositions are used as a topical antibacterial medication for skin infections caused by methicillin-resistant *Staphylococcus aureus*. Methicillin-resistant *Staphylococcus aureus* (MRSA) is a bacterium that is resistant to many antibiotics. The spectrum of disease caused by MRSA appears to be similar to that of *Staphylococcus aureus* in the community. Soft tissue infections (SSTIs), specifically furuncles (abscessed hair follicles or "boils"), carbuncles (coalesced masses of furuncles), and abscesses, are the most frequently reported clinical manifestations.

The most common manifestations of community associated-MRSA are simple skin infections, such as impetigo, boils, abscesses, folliculitis, and cellulitis. Others include children with minor skin infections (such as impetigo) and secondarily infected skin lesions (such as eczema, ulcers, or lacerations). The compositions can also be used to treat MRSA infections of the CNS, which include, but are not limited to Meningitis, Brain abscess, subdural empyema, spinal epidural abscess. Reviewed in Liu, et al., *Clin Infect Dis.,* 52(3):e18-55 (2011).

Additional examples of conditions that can be treated include atopic dermatitis, acne, bullous and non-bullous impetigo, pemphigus *foliaceus*, miliaria, feruncles (also known as boils) and chronic wounds such as diabetic foot ulcers, venous insufficiency ulcers, and pressure ulcers.

In the context of treating acne, an effective concentration of 340 µM is demonstrated in Example 24, although higher or lower concentrations of the one or more compounds according to section III.A below may also be suitable for the treatment of acne and any of the other skin conditions as discussed herein. For example, the treatment of these skin conditions may utilize one or more of the compounds at a concentration within the range of about 1 µM to about 1M, such as about, or up to, 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM, 200 µM, 210 µM, 220 µM, 230 µM, 240 µM, 250 µM, 260 µM, 270 µM, 280 µM, 290 µM, 300 µM, 310 µM, 320 µM, 330 µM, 340 µM, 350 µM, 360 µM, 370 µM, 380 µM, 390 µM, 400 µM, 410 µM, 420 µM, 430 µM, 440 µM, 450 µM, 460 µM, 470 µM, 480 µM, 490 µM, 500 µM, 510 µM, 520 µM, 530 µM, 540 µM, 550 µM, 560 µM, 570 µM, 580 µM, 590 µM, 600 µM, 610 µM, 620 µM, 630 µM, 640 µM, 650 µM, 660 µM, 670 µM, 680 µM, 690 µM, 700 µM, 710 µM, 720 µM, 730 µM, 740 µM, 750 µM, 760 µM, 770 µM, 780 µM, 790 µM, 800 µM, 810 µM, 820 µM, 830 µM, 840 µM, 850 µM, 860 µM, 870 µM, 880 µM, 890 µM, 900 µM, 910 µM, 920 µM, 930 µM, 940 µM, 950 µM, 960 µM, 970 µM, 980 µM, 990 µM, 1 mM, 2 mM, 3 mM, 4 mM, 5 mM, 6 mM, 7 mM, 8 mM, 9 mM, 10 mM, 15 mM, 20 mM 25 mM, 30 mM, 35 mM, 40 mM, 45 mM, 50 mM, 60 mM, 70 mM, 80 mM, 90 mM, 100 mM, 150 mM, 200 mM, 250 mM, 300 mM, 350 mM, 400 mM, 450 mM, 500 mM, 600 mM, 700 mM, 800 mM, 900 mM, 1M or more. Optionally, the concentration may be:

(a) up to 1 µM, 2 µM, 3 µM, 4 µM, 5 µM, 10 µM, 15 µM, 20 µM, 25 µM, 30 µM;

(b) within a range selected from the group consisting of from 35 to 335 µM, 40 to 300 µM, 50 to 300 µM, 50 to 250 µM, 50 to 200 µM, 60 to 300 µM, 60 to 250 µM, 60 to 200 µM, 80 to 300 µM, 80 to 250 µM, 80 to 200 µM, 100 to 300 µM, 100 to 250 µM, or 100 to 200 µM; or (c) at least, or about, 345 µM, 350 µM, 360 µM, 370 µM, 380 µM, 390 µM, 400 µM, 450 µM, 0.5 mM, 1 mM, 2 mM or more.

Optionally the concentration of the one or more compounds may be in within a range selected from the group consisting of from about 1 µM to about 1 mM, or about 30 µM to about 0.5 mM, or about 60 µM to about 0.4 mM.

Atopic dermatitis (AD) affects 10-20% of children with 60% of cases occurring within a child's first year and 85% before the age of 5 (Krakowski, et al., *Pediatrics,* 122(4): 812-24 (2008)). Many cases persist into adulthood as evidenced by the 1-3% prevalence of AD among the adult population (Leung, et al., Lancet, 361(9352):151-60 (2003)). AD patients are colonized with *S. aureus* and this organism has been shown to exist in both dry skin as well as areas of severe dermatitis (Ikezawa, et al., *Allergy Asthma Immunol Res.,* 2(4):235-46 (2010)). Disease severity has been directly correlated to the degree of *S. aureus* colonization and therapy generally fails to improve symptoms in the presence of high *S. aureus* counts (Akiyama, et al., *J Dermatol Sci.,* 23(3):155-6 (2000)). Confocal laser scanning micro has demonstrated the presence of biofilms in skin stripping and biopsy specimens from AD patients (Akiyama, et al., Br J Dermatol., 148(3):526-32 (2003)). The presence of *S. aureus* biofilms have been shown in specimens of bullous impetigo and pemphigus *foliaceus* (Akiyama, et al., *Br J Dermatol.,* 148(3):526-32 (2003)) while biofilms containing both *S. aureus* and *Streptococcus pyogenes* have been identified in non-bullous impetigo (Akiyama, et al., *J Dermatol Sci.,* 32(3):193-9 (2003)). The difficulty in eradicating *S. aureus* colonization with conventional antibiotic therapy may be due to the presence of biofilms. Biofilm formation has also been demonstrated in a murine model inoculated with *S. aureus* isolated from a furuncle (Yamasaki, et al., *J Antimicrob Chemother.,* 48(4):573-7 (2001)).

Biofilms have been implicated in miliaria by a clinical study in which only extracellular polymeric substance (EPS) producing *S. epidermidis* was capable of inducing lesions after inoculation and occlusion (Mowad, et al., *J Am Acad Dermatol.,* 33(5 Pt 1):729-33 (1995)). Biopsy specimens revealed sweat glands blocked with EPS material, further supporting a pathogenic role for biofilms in this condition. Several factors, for example, firm adherence of dermatophytes to the nail plate, presence of dormant fungal elements, ability of yeast to form biofilms, and difficulty of eradication all suggest that biofilm involvement in onychomycosis (Burkhart, et al., *J Am Acad Dermatol.,* 47(4):629-31 (2002)).

Chronic wounds present an optimal environment for microbial proliferation. In a clinical study of 66 wounds of various etiologies, 60% of chronic wounds were shown to contain biofilms as compared to 6% of acute wounds, indicating a role of biofilms in wound chronicity. Traditional cultures identified *Staphylococcus, Pseudomonas,* and *Enterococcus* as the predominant organisms (James, et al., *Wound Repair Regen.,* 16(1):37-44 (2008).

In a preferred embodiment, the compounds may be incorporated into wound irrigation solutions. In another preferred embodiment, the compounds may be incorporated into cosmetic formulations.

Compositions of the compounds disclosed herein are also useful in oral health for both prophylaxis and treatment of infections. For example, the compounds may be used to treat or prevent infections in dental pulp by *Streptococcus anginosus,* or prevent attachment of biofilms to tooth surfaces. The compounds may be applied directly to tooth surfaces or applied to dental pulp during a procedure. The compounds may also be incorporated into dental products such as toothpaste, mouthwash, floss, toothpicks, and chewable products (including food products), a mouth shield, a dental instrument, dentures, dental retainers, dental braces including plastic braces (such as Invisalign®), bristles of toothbrushes, dental prostheses and orthodontic devices, chewable non-food items, or foods, as well as applied as coatings directly to dental tissues. The compositions may be used for dental care of both humans and animals, including pets such as dogs and cats as well as livestock and horses. For example, the compounds may be incorporated into chewable foods or toys, such as dog bones and biscuits.

In fact, in one embodiment of particular, there is provided a human or animal (especially a dog) chew composition comprising one or more compounds. Exemplary dog and other animal chews which can be modified to include the one or more compounds include those described in U.S. Pat. No. 6,086,940. Further exemplary chews include the Oravet® dental hygiene chew produced by Merial and the Kalloodles dental chews. Dental chews can be used in dogs and other animals to inhibit the production of biofilms that form plaque, and/or to reduce or treat or prophylactically treat halitosis. Chewing the chews may also help scrub away existing plaque and/or calculus. Optionally, the chews may be usefully used regularly, such as daily and optionally daily after one or more meals.

The compounds may be added to drinking water or other drinkable fluids.

Other modes of administration can include:

(i) Parenteral administration, which may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion. Parenteral administration can include the use of formulations as described herein which are formulated for controlled release including immediate release, delayed release, extended release, pulsatile release, and combinations thereof, as further herein.

(ii) The compounds can be incorporated into injectable/implantable solid or semi-solid implants, such as polymeric implants.

(iii) Enteral administration, including administration in the form of suitable oral dosage forms such as tablets, capsules, solutions, suspensions, syrups, and lozenges. Optionally, enteral administration may include administration of controlled release enteral formulations, including oral dosage forms, such as capsules, tablets, solutions, and suspensions, which are formulated for controlled release, including extended and/or delayed release.

(iv) The administration of one or more disinfecting formulations or cleaning formulations.

3. Hospital and Other Environments

Methods and uses disclosed herein may be practiced in the hospital and also in other medical and non-medical environments in order to address, inhibit, treat, ameliorate and/or disrupt biofilms. Further examples of microbial infection and colonizations and biofilm formations are discussed further below, including medical uses and methods for the treatment and/or prophylaxis of subjects (including humans and animals) in need thereof.

For example, *S. epidermidis* contributes to biofilms that grow on plastic devices placed within the body (Otto, *Nature Reviews Microbiology*, 7(8):555-567 (2009)). This occurs most commonly on intravenous catheters and on medical prostheses (Hedin, *Scandinavian Journal of Infectious Diseases Supplementum*, 90:1-59 (1993)). Infection can also occur in dialysis patients or anyone with an implanted plastic device that may have been contaminated. Another disease it causes is endocarditis. This occurs most often in patients with defective heart valves. In some other cases, sepsis can occur in hospital patients.

As a further example, Methicillin-resistant *S. aureus* (MRSA), is one of a number of greatly feared strains of *S. aureus* which have become resistant to most β-lactam antibiotics. MRSA strains are most often found associated with institutions such as hospitals, but are becoming increasingly prevalent in community-acquired infections. A recent study by the Translational Genomics Research Institute showed that nearly half (47%) of the meat and poultry in U.S. grocery stores were contaminated with *S. aureus*, with more than half (52%) of those bacteria resistant to antibiotics (ScienceDaily, 15 Apr. 2011).

In another example, *Enterococcus faecalis* causes many of the antibiotic resistant infections in hospitals, a consequence of its inherent resistance to certain antibiotics and its ability to survive and proliferate in the intestinal tract. *Escherichia coli* is one of the most frequent causes of many common bacterial infections, including cholecystitis, bacteremia, cholangitis, urinary tract infections other clinical infections such as neonatal meningitis and pneumonia. For example, the compositions can be used to treat (for example, as adjunct therapy) conditions caused by community- and/or hospital-acquired urinary tract infections (UTI's) caused by strains of *Escherichia coli* (drug resistant or otherwise) in immunocompromised patients.

In accordance with a further example, the aggressive colonization of stainless steel surfaces by *P. aeruginosa* for example, apart from being of enormous industrial significance, is also of medical relevance; *P. aeruginosa* infections are prevalent in burn units where large stainless steel tubs, known as hydrotherapy units, are often used to treat patients with severe burns.

Antibiotics are largely ineffective in clearing biofilms, although they may be combined with the compounds in order to potentiate the effect of antibiotics.

The most common treatment for these infections is to remove or replace the infected implant, though in all cases, prevention is ideal. The drug of choice is often vancomycin, to which rifampin or aminoglycoside can be added. Hand washing has been shown to reduce the spread of infection. Accordingly, compositions in accordance with the third aspect of the present disclosure may include hand wash and/or hand spray compositions, and may be used accordingly in the treatment of hands and other body surfaces.

Preliminary research also indicates *S. epidermidis* is universally found inside affected acne vulgaris pores, where *Propionibacterium acnes* is normally the sole resident (Bek-Thomson, et al., *J. Clin. Microbiol.*, 46(10):3355-3360 (2008).

a. Use as Disinfection Agent

The one or more compounds for use in the third aspect of the present disclosure can, in accordance with a further embodiment, be used as disinfection (or pesticide) agents (the United States Environmental Protection Agency, "EPA", defines biofilms as pestilent), for example, in high risk environments such as in hardware from hospitals or healthcare facilities. As such, the one or more compounds may be formulated as a disinfecting formulation or cleaning formulation.

In accordance with a further embodiment there is provided a method or use comprising the use of the disinfection agent in high-risk environments such as in hardware from hospitals or healthcare facilities, cosmetic, consumer and industrial applications, to prevent biofilm buildup or reduce biofilm from a surface of interest. In these embodiments, the compounds may, for example, be sprayed onto the surface in the form of a foam, solution or gel, or applied to the surface (wipe down) by means of a carrier for example tissue, material or other porous item containing the one or more compounds.

The World Health Organization (WHO) estimates that at any time, more than 1.4 million people worldwide are affected by infections acquired in hospitals. Cleaning, disinfection and sterilization saves lives and improves patient outcomes. Between 5% and 10% of patients admitted to modern hospitals in the developed world acquire one or more healthcare-associated infections. The Centers for Disease Control and Prevention (CDC) estimate that approximately 1.7 million healthcare-associated infections occur annually in hospitals in the United States, and are associated with nearly 100,000 deaths each year. Healthcare-associated infections are also an important problem in extended care facilities, including nursing homes and rehabilitation units. Transmission of healthcare-associated pathogens most frequently occurs via the hands of healthcare workers, who inadvertently contaminate their hands during various patient care activities. Less frequently, contaminated surfaces in healthcare facilities may contribute to the spread of healthcare-associated pathogens.

The varying levels of disinfection used in a healthcare facility may be defined by Spaulding's Classification (Sehulster, et al., Guidelines for environmental infection control in health-care facilities. Recommendations from CDC and the Healthcare Infection Control Practices Advisory Committee (HICPAC). Chicago Ill.; American Society for Healthcare Engineering/American Hospital Association; 2004.). Spaulding's levels, non-critical, semi-critical, and critical, are based on the potential for infectious disease spread via equipment, instruments, and furniture as well as the level of sterility normally required for the body part coming in contact with it. Levels of disinfection that correlate with Spaulding's classification are low, intermediate, high, and sterilization. The US Centers for Disease Control (CDC) has further delineated disinfection levels for environmental surfaces in its "Guidelines for Environmental Infection Control in Health-Care Facilities".

Critical items confer a high risk for infection if they are contaminated with any microorganism. Thus, the third aspect of the present disclosure also provides objects treated for sterilization as described herein, which objects enter sterile tissue or the vascular system and must be sterile because any microbial contamination could transmit disease. This category includes surgical instruments, cardiac and urinary catheters, implants, and ultrasound probes used in sterile body cavities. Semi critical items contact mucous membranes or nonintact skin. This category includes respiratory therapy and anesthesia equipment, some endoscopes, laryngoscope blades, esophageal manometry probes, cystoscopes, anorectal manometry catheters, and diaphragm fitting rings. These medical devices should be free from all microorganisms; however, small numbers of bacterial spores are permissible. Specific examples of critical or semi critical instruments include invasive endoscopes such as laparoscopes, and rigid instruments with no operating channel Arthroscopes and laparoscopes which are inserted into sterile body cavities as well as accessory instrumentation should be sterile. Other examples include gastroscopes, duodenoscopes, sigmoidoscopes, proctoscopes, colonoscopes, bronchoscopes, and laryngoscopes.

The compounds may also be used e as food processing aids. For example, solutions of the one or more compounds below could be sprayed on animal carcasses or products (include meat part products) derived therefrom (i.e. poultry, fish, and meat or others, for example, as described above) to prevent or inhibit colonization by bacteria, or inactivate biofilm formation. The compounds could, for example, be applied by dipping chicken (or other animal) carcasses or product derived therefrom in a container of a solution of the compounds, or by spraying an animal carcass with a solution of the compounds.

In certain embodiments, aqueous solutions of Fe-Lac, Fe-Cit, Fe-Tart, Fe-Gly, FeQ, FeTyr, FeDOPA and/or Fe-Phe may be used as food processing aids. After treatment, the compounds may, if desired, be removed by washing.

A further embodiment provides an animal carcass (such as a chicken or other poultry, fish or other meat) and/or products (include meat part products) derived therefrom which have been treated, for example by spraying or dipping, and optionally wherein the one or more compounds are subsequently removed fully or partially by washing.

b. Use as a Coating

The compounds can be incorporated into coatings used to coat medical devices, and other articles. Also provided are coated devices or articles, having a coating comprising, consisting essentially of, or consisting of, one or more of the compounds.

Suitable coating methods are known in the art. Methods for coating medical devices are disclosed for example in U.S. Publication Nos. 20030054090 and 20120276280 and U.S. Pat. Nos. 5,879,697, 7,247,338 and 8,028,646. The compounds can be applied to medical devices and other articles in any number of ways, including, but not limited to, ionic binding to a surface coating, passive adsorption, or dispersion within a polymeric base material making up the surface of the device or coated on the device surfaces (for example by dip coating, spray coating, ultrasonic spray coating, melt processing, application of films, solvent coating, etc.).

In a preferred embodiment, the one or more compounds are combined with polymers, and coated on medical devices or other articles. Suitable polymers include, but are not limited, to poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); polyhydroxyalkanoates [including poly-3-hydroxybutyrate, poly-3-hydroxybutyrate-co-3-hydroxyvalerate (PHBV), poly-4-hydroxybutyrate, poly-3-hydroxybutyrate-co-4-hydroxybutyrate]; synthetically or biologically prepared polyesters (including polyesters with one or more of the following monomeric units: glycolic, lactic; trimethylene carbonate, p-dioxanone, or □-caprolactone); poly(lactide-co-caprolactones); polyesters; polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly(lactide), poly (lactide-co-glycolide, or polycaprolcatone or combinations thereof, polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, Dacron, latex, silicones, polymeric cements, and poly(ethylene oxide).

In another preferred embodiment, the one or more compounds can be first conjugated with other agents that have an affinity for, or can react with, a surface, and thereby immobilized on a surface. For example, the compounds can be tethered to a linkage that can be photo-activated to bind to a surface, or activated via another mechanism.

Examples of devices and articles that can be coated using the compositions include tubing and other surface medical devices, such as urinary catheter, stents, mucous extraction catheter, suction catheter, umbilical cannula, contact lenses, intrauterine devices, intravaginal and intraintestinal devices, endotracheal tubes, bronchoscopes, dental prostheses and orthodontic devices, dentures, teeth, surgical instruments, dental instruments, tubing, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. Devices may include electrodes, external prostheses, fixation tapes, compression bandages, and monitors of various types. Medical devices also include any device that may be placed at the insertion or implantation site such as the skin near the insertion or implantation site, and which include at least one surface which is susceptible to colonization by biofilm embedded microorganisms. In one specific embodiment, a composition is integrated into an adhesive, such as tape, thereby providing an adhesive, which may prevent growth or proliferation of biofilm embedded microorganisms on at least one surface of the adhesive. Medical devices include surfaces of equipment in operating rooms, emergency rooms, hospital rooms, clinics, and bathrooms. In a particularly preferred embodiment the following devices may be coated with the compounds: catheters, including central venous catheters, urinary catheters, dialysis catheters, and indwelling catheters (for example, catheters for hemodialysis and for administration of chemotherapeutic agents), cardiac implants including mechanical heart valves, stents, ventricular assist devices, pacemakers, cardiac rhythm management (CRM) devices, cardiac resynchronization therapy devices (CRTs), and implantable cardioverter defibrillators (ICDs), synthetic vascular grafts, arteriovascular shunts, cerebral spinal fluid shunts, cochlear devices, prosthetic joints, orthopedic implants, internal fixation devices, bone cements, percutaneous sutures, surgical mesh and surgical patches including hernia repair meshes and patches, breast reconstruction meshes and patches, meshes and patches for breast and face lifts, slings, and meshes and patches for pelvic floor reconstruction, tracheal and ventilator tubing, wound dressings, biological implants (including allografts, xenografts and autografts), penile implants, intrauterine devices, endotracheal tubes, and contact lenses.

Other articles that can be coated as disclosed herein include articles for use in rearing animals, articles for use in the process of slaughter and/or processing the carcasses or parts thereof of animals such as animals and articles as disclosed above.

Yet further articles that can be as disclosed herein include articles for the preparation and/or containment of food stuffs or drinks, including foodstuffs comprising raw or cooked meats, eggs, dairy products or other food products. The food products may be human and/or animal food products.

Accordingly, provided is a method of disinfecting a surface, or protecting a surface against infection, in need thereof, the method comprising contacting the surface with an effective amount of one or more compounds having the structure of having the structure of Formula I, wherein the one or more compounds are coated onto the surface to be disinfected.

In some embodiments the one or more compounds may be applied to the surface in the form of a spray, an aerosol, or a foam.

The coated surface may, for example, be formed on the surface of an instrument selected from the group consisting of surgical instruments, cardiac and urinary catheters, implants, and ultrasound probes used in sterile body cavities.

The coated surface may, for example, be formed on the surface of a device selected from the group consisting of urinary catheter, stents, mucous extraction catheter, suction catheter, umbilical cannula, contact lenses, intrauterine devices, intravaginal and intraintestinal devices, endotracheal tubes, bronchoscopes, dental prostheses and orthodontic devices, surgical instruments, dental instruments, tubing, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, catheters, including central venous catheters, urinary catheters, dialysis catheters, and indwelling catheters, cardiac implants, mechanical heart valves, stents, ventricular assist devices, pacemakers, cardiac rhythm management (CRM) devices, cardiac resynchronization therapy devices (CRTs), and implantable cardioverter defibrillators (ICDs), synthetic vascular grafts, arteriovascular shunts, cerebral spinal fluid shunts, cochlear devices, prosthetic joints, orthopedic implants, internal fixation devices, bone cements, percutaneous sutures, surgical mesh and surgical patches including hernia repair mesh, breast reconstruction mesh, mesh for breast and face lifts, slings, and mesh for pelvic floor reconstruction, tracheal and ventilator tubing, wound dressings, biological implants, penile implants, intrauterine devices, endotracheal tubes, and contact lenses.

The coated surface may, for example, be formed on the surface of an article selected from the group consisting of an industrial pipeline, liquid distribution lines, oil and gas pipelines and cosmetic container.

The coated surface may, for example, be formed on the surface of, or be incorporated into, or onto, a household item, such as an item selected from the group consisting of household disinfectants; laundry detergent; cleaning supplies; equipment involved in the leeching process or mining; wound care; toothpaste; mouth wash; dental floss; toothpicks; chewable products (including food products); a mouth shield; a dental instrument; dentures; dental retainers; dental braces including plastic braces (such as Invisalign®); bristles of toothbrushes; dental prostheses and orthodontic devices; chewable non-food items, foods, or toys, such as dog bones and biscuits; a vacuum system; HVAC ((heating, ventilation and air conditioning)) systems; vacuum cleaner bags; paint covering; wall coverings; window frames; doors; door frames; cooling towers; humidifiers; vacuum cleaners; filters such as a vacuum filter, a humidifier filter, hot tub filter, or a swimming pool filter; toys; plastic bottles; water jugs; tap and water spout; washing machines; dishwashers; animal water dishes; bathroom tiles and fixtures; sinks;

showers; shower heads; toilets; toilets lids; toilet seats; sealants and grout; towels; TUPPERWARE®; dishes; cups; utensils such as forks, spoons, knives, and spatulas; bowls; food storage containers; beverage storage containers; cutting boards; dish drying trays; garbage bags; sinks; fish ponds; swimming pools; swimming pool liners; swimming pool skimmer; pond liners; bird baths; garden hose; water sprinkling lines; planters; and hot tubs.

The coated surface may, for example, be formed on the surface of, or incorporated into, or onto, an article, device or apparatus used in the rearing and/or transport of animals. In some embodiments, the device or apparatus used in the rearing and/or transport of animals may be selected from an article, device or apparatus that is for the delivery and/or containment of animal feed and/or animal drinking water.

The coated surface may, for example, be formed on the surface of, or incorporated into, or onto, an article, device or apparatus used in the rearing, housing and/or transport of animals, In some embodiments, the article, device or apparatus used in the rearing, housing and/or transport of animals can include one or more of an article, device or apparatus used in the production, creation, collection, storage, processing and/or packaging of an animal product. For example, an animal product may be a by-product of the animal (e.g. milk, eggs, or wool) or a downstream product thereof. Alternatively, an animal product may be the body or part of the body of the animal, and the harvesting process optionally includes the step of slaughtering the animal and further optionally preparing an animal carcass or part thereof as a product, such as a meat product.

A device, article, product, item, formulation, composition or coating may comprise the one or more compounds in the coating in an amount effective to prevent biofilm formation. In another embodiment, the device, article, product, item, formulation, composition or coating comprises the one or more compounds in the coating in an amount effective to treat or reduce biofilm formation.

Compositions contemplated herein also include the direct per se products of the above-defined methods and uses, and downstream product produced therefrom.

Also provided is a compound conjugated to a structure that can anchor to a surface, wherein the compound has the structure of having the structure of Formula I. It may be preferred that the compound binds to major outer membrane proteins (MOMPs) or FlaA of *Campylobacter*, a synthetic human histo-blood group antigen, a mimetic of human histo-blood group antigen or a synthetic sugar.

Also provided is a composition comprising one or more conjugated compounds as defined above, and an article coated with one or more of the conjugated compounds, or with the composition.

In one embodiment, the structure of the conjugated compound comprises hydroxyapatite or derivative thereof, and the conjugate is capable of anchoring, or is anchored to, a dental tissue.

For example, in a further embodiment, conjugated forms of the compounds, such as those shown in FIGS. 16A and B wherein the compounds are conjugated to hydroxyapatite may be applied to tooth tissues, such as tooth enamel, dentin and pulp in order to prevent dental caries and infection. In another embodiment, the compounds can be applied using photo-reactive chemistry, for example, using conjugated forms of the compounds such as those shown in FIGS. 15A and B.

4. Industrial, Cosmetic and Consumer Applications

The compositions can be used in accordance with a further embodiment, disinfect industrial surfaces, by preventing and/or removing biofilm buildup on such surfaces. In this embodiment, the formation of the biofilm may be prevented or inhibited, or a preformed biofilm may be removed by a method that comprises applying a composition comprising the one or more compounds having the structure of Formula I, onto a surface in need thereof, for example as a spray, foam, gel, powders; dish or laundry detergents (liquid or solid), surface wax, glass cleaner, etc.

An object or article that has been treated in accordance with the foregoing method is also provided.

Biofilms are continuously produced and often accumulate on numerous industrial surfaces and on biological surfaces. In an industrial setting, the presence of these biofilms causes a decrease in the efficiency of industrial machinery, requires increased maintenance, and presents potential health hazards. For example, the surfaces of water cooling towers become increasingly coated with microbially produced biofilm slime which both constricts water flow and reduces heat exchange capacity. Water cooling tower biofilms may also harbor pathogenic microorganisms such as *Legionella pneumophila*. Food preparation lines are routinely plagued by biofilm build-up both on the machinery and on the food product where biofilms often include potential pathogens. Biofilm formation comes with associated problems, such as accelerated deterioration of equipment through corrosion from cellular byproducts. There may also be a reduction in the efficacy of heat transfer and impairment of detection devices as the film disrupts transmission.

*Pseudomonas aeruginosa* readily binds to stainless steel or plastic (e.g. polyvinylchloride, polystyrene) surfaces causing major problems in both the medical and food industries, forming biofilm. Biofilms readily form on PVC and glass surfaces under the static condition, especially in the food industry.

a. Industrial Applications

The compositions and coatings disclosed herein can be used to clean, or maintain, pipelines and hoses in industries such as food and beverage industries, paper mills, sewage treatment, drainage, cooling towers and gas and oil industries by contacting a surface with biofilm growth with the composition. Industrial applications include their use in dairy lines, either as a flush or wash for such lines, or incorporated within the lines, for example as a coating; liquid distribution lines in the food and beverage manufacturing or dispensing, for example, use as a coating in feeder lines for high sugar or syrup distribution in the manufacturing of soft drinks; pulp and paper mills (for biofouling); in the manufacturing and containment of cosmetics from production line equipment down to the end consumable, either incorporated within the cosmetic or coated on the jar containing the cosmetic; in water treatment facilities; in the leaching process used in mining; to prevent corrosion caused or accelerated by organisms, in oil and gas pipelines including fracking pipes, in the souring of oil fields, in antifouling coatings (for example on submarines and boats), and in cooling towers.

b. Consumer and Light Commercial Applications

Consumer and light commercial uses of the compounds and coatings include their incorporation in general household disinfectants; laundry detergent; cleaning supplies; equipment involved in the leeching process or mining; wound care; a vacuum system; HVAC (heating, ventilation and air conditioning) systems; vacuum cleaner bags; paint covering; wall coverings; window frames; doors; door frames; cooling towers; boat hulls, humidifiers; vacuum cleaners; filters and membranes, such as a vacuum filter, a humidifier filter, hot tub filter, osmosis membranes, or a swimming pool filter; toys; plastic bottles; water jugs; toothpaste, mouthwash, a tap and water spout; incorporation into plastics for a variety of household items including the inside and outside of washing machines and dishwashers; animal water dishes; bathroom tiles and fixtures; sinks; showers; shower heads; toilets; toilets lids; toilet seats; sealants and grout; towels; TUPPERWARE®; dishes; cups; utensils such as forks, spoons, knives, and spatulas; bowls; food storage containers; beverage storage containers; cutting boards; dish drying trays; garbage bags; bathtubs including whirlpool and jacuzzi bathtubs; sinks; fish ponds and tanks; swimming pools; swimming pool liners; swimming pool skimmer; pond liners; bird baths; garden hose; water sprinkling lines; planters; and hot tubs.

c. Cosmetic Applications

Cosmetics and cosmetic applications, as well as containers for cosmetics and applicators for cosmetics that incorporate and/or are coated by, the one or more compounds having the structure of Formula I, are also provided.

Cosmetics (also known as makeup or make-up) include care substances used to enhance the appearance or odor of the human body. They are generally mixtures of chemical compounds, some being derived from natural sources (including natural oils) and many being synthetics. A cosmetic may be a substance that is suitable to be applied to the human body for cleansing, beautifying, promoting attractiveness, or altering the appearance without affecting the body's structure or functions. Although soap is traditionally not considered to be a cosmetic, for the purposes of the present description the discussion of cosmetics can also be applied to soaps.

Exemplary cosmetics include skin-care creams, lotions, powders, perfumes, lipsticks, fingernail and toe nail polish, eye and facial makeup, towelettes, permanent waves, colored contact lenses, hair colors, hair sprays and gels, deodorants, hand sanitizer, baby products, bath oils, bubble baths, bath salts, butters and many other types of products. A subset of cosmetics is called "make-up," which refers primarily to coloring products intended to alter the user's appearance. Cosmetics that are meant to be used on the face and eye area are usually applied with a brush or the fingertips.

Cosmetics may comprise a variety of organic compounds and inorganic compounds. Typical organic compounds can include modified natural oils and fats as well as a variety of petrochemically derived agents. Inorganic compounds can include processed minerals such as iron oxides, talc, and zinc oxide. The oxides of zinc and iron may be classified as pigments, i.e. colorants, and may have no solubility in solvents.

The application discloses compounds for cosmetics, cosmetic applications, cosmetic containers and/or cosmetic applicators may provide for methods to reduce, avoid, minimise or disrupt biofilms in the cosmetics, containers and/or applicators. Further, insofar as the applicant of the cosmetic to the body of the user achieves the delivery of one or more compounds, then the cosmetics may be used to treat individuals as disclosed herein, particularly in the context of treating, reducing, prevent or disrupting bacterial infections, colonization, or biofilms on the skin, hair, nails, and/or in teeth of the user.

5. Additional Medical Applications

A further use of the compounds having the structure of Formula I, and compositions comprising one or more of the compound, is to treat any medical condition associated with biofilm formation as a result of microorganisms including, but not limited to gram-negative and gram-positive bacteria, including *Pseudomonas*, *H. pylori*, *E. feacalis*, *Campylobacter*, *E. coli*, EPEC, UPEC and *Staphylococcus*.

In addition to the conditions discussed above, rarer, but more serious manifestations of MRSA can occur, such as necrotizing fasciitis and pyomyositis (most commonly found in the tropics), necrotizing pneumonia, infective endocarditis (which affects the valves of the heart), and bone and joint infections. Additional conditions include severe or extensive disease (e.g., involving multiple sites of infection) or rapid progression in presence of associated cellulitis, signs and symptoms of systemic illness, associated comorbidities or immunosuppression, extremes of age, abscess in an area difficult to drain (e.g., face, hand, and genitalia), associated septic phlebitis, and lack of response to incision and drainage alone, purulent cellulitis, hospitalized patients with complicated SSTI (cSSTI; defined as patients with deeper soft-tissue infections, surgical/traumatic wound infection, and infected ulcers and burns), osteomyelitis, device-related osteoarticular infections.

In a further embodiment, the compounds having the structure of Formula I, may also be used in the treatment of keratitis, colon cancer (where biofilms play a role), and peri-implantitis, a bacterial infection around an implant that results in inflammation of the gums, and can lead to bone loss in the jaw.

Certain strains of enterohaemorrhagic *E. coli* (EHEC) found in the gut of both animals and humans can cause disease, and can be life-threating in a small group of patients that develop haemolytic uraemic syndrome (HUS). EHEC is not treated with antibiotics because of the risks of developing HUS. The compounds may be useful in the treatment of EHEC infections both in humans and animals, and particularly in cattle.

Uropathogenic *E. coli* (UPEC) is the predominant etiologic agent that causes UTIs. Accordingly, the compositions can also be used to inhibit or reduce biofilm involved in lower urinary tract infections (UTIs). UTI's in human have been traditionally considered to be a self-limiting disease involving bacteria residing in the lumen of bladders. Intracellular bacterial community-like structures also have been identified in the urine sediments of patients with UTIs in a prospective study.

In one embodiment, the biofilm that is inhibited or disrupted is a bacterial biofilm. The bacteria forming the biofilm may be gram positive, or in an alternative embodiment may be gram negative, or the biofilm may be formed by a mixture of gram positive and gram negative bacteria.

Optionally, the biofilm may be formed by bacteria selected from the group consisting of *S. epidermidis*, *E. faecalis*, *E. coli*, *S. aureus*, *H. pylori*, *Campylobacter*, Enteropathogenic *Escherichia coli* (EPEC), Uropathogenic *Escherichia coli* (UPEC), and *Pseudomonas* or combinations thereof. Optionally, in certain embodiments, the biofilm is a biofilm that is formed by bacteria other than bacteria that comprise, consist essentially of, or consist of proteobacteria class, such as any one or more of the spirilloid *Wolinella* spp., *Helicobacter* spp., and most particularly *Campylobacter* spp.

Optionally, the one or more compounds administered to a subject (such as a human or animal) according to the methods above may be a pharmaceutical or veterinary product, and further may include one or more excipients, such as discussed in section III.C of this application, below.

In one embodiment for the treatment of biofilms in a subject (such as a human or animal), the one or more compounds is administered to a subject by one or more routes selected from: parenteral delivery, such as discussed below in section III.C.1 of this application, including a controlled release formulation, such as discussed below in section III.C.1(a) of this application, and injectable or implantable formulation, such as discussed below in section III.C.1(b) of this application; enteral delivery, such as discussed below in section III.C.2 of this application, including a controlled release enteral formulation, such as discussed below in section III.C.2(a) of this application, with further reference to extended release dosage forms and delayed release dosage forms as discussed therein; oral delivery; topical delivery, such as discussed below in section III.C.3 of this application, including as an emulsion, lotion, cream, ointment, gel, or foam as discussed in parts (a), (b), (c), (d) (e) and (f) respectively below in section III.C.3 of this application; buccal delivery; sublabial delivery; sublingual delivery; in or on a dental product, such as a toothpaste, a mouthwash, a dental floss, a mouth shield; dermal delivery; or transdermal delivery.

In some embodiment, the biofilm may be associated with a bacterial infection selected from the group consisting of impetigo, boils, abscesses, folliculitis, cellulitis, necrotizing fasciitis, pyomyositis, surgical/traumatic wound infection, and infected ulcers and burns), osteomyelitis, device-related osteoarticular infections, impetigo, secondarily infected skin lesions, meningitis, brain abscess, subdural empyema, spinal epidural abscess, arterial damage, gastritis, urinary tract infections, biliary tract infections, pyelonephritis, cystitis, sinus infections, ear infections, otitis media, otitis externa, leprosy, tuberculosis, conjunctivitis, bloodstream infections, benign prostatic hyperplasia, chronic prostatitis, lung infections including chronic lung infections of humans with cystic fibrosis, osteomyelitis, catheter infections, bloodstream infections, skin infections, acne, rosacea, dental caries, periodontitis, gingivitis, nosocomial infections, arterial damage, endocarditis, periprosthetic joint infections, open or chronic wound infections, venous stasis ulcers, diabetic ulcers, arterial leg ulcers, pressure ulcers, endocarditis, pneumonia, orthopedic prosthesis and orthopedic implant infections, peritoneal dialysis peritonitis, cirrhosis, and any other acute or chronic infection that involves or possesses a biofilm.

A further embodiment provides a method of treating a microbial infection in a subject in need thereof, the method comprising administering to the subject an effective amount of one or more compounds having the structure of Formula I. Likewise, this embodiment also provides for the use of one or more of the compounds for treating a microbial infection in a subject in need thereof.

In certain embodiments, the microbial infection is caused by bacteria, such as gram positive bacteria, or gram negative bacteria. For example, the infection may be caused by bacteria selected from the group consisting of *S. epidermidis, E. faecalis, E. coli, S. aureus, H. pylori, Campylobacter,* Enteropathogenic *Escherichia coli* (EPEC), Uropathogenic *Escherichia coli* (UPEC), and *Pseudomonas* or combinations thereof and/or optionally wherein the infection is not caused by bacteria that comprise, consist essentially of, or consist of proteobacteria class, such as any one or more of the spirilloid *Wolinella* spp., *Helicobacter* spp., and most particularly *Campylobacter* spp . . . . .

Optionally, in the treatment of a microbial infection in a subject in need thereof as disclosed herein, the one or more compounds may be administered to a subject by parenteral delivery; enteral delivery; oral delivery; topical delivery, such as in the form of an emulsion, lotion, cream, ointment, gel or foam; buccal delivery; sublabial delivery; sublingual delivery; in or on a dental product or dental device, such as a dental product, including but not limited to a toothpaste, a mouthwash, a dental floss, toothpicks, chewable products (including food products), a mouth shield, a dental instrument, dentures, dental retainers, dental braces including plastic braces (such as Invisalign®), bristles of toothbrushes, dental prostheses and orthodontic devices, chewable non-food items, foods, or toys, such as dog bones and biscuits; dermal delivery; or transdermal delivery.

In certain embodiments, the treatment of a microbial infection in a subject in need thereof may be to treat an infection is selected from the group consisting of impetigo, boils, abscesses, folliculitis, cellulitis, necrotizing fasciitis, pyomyositis, surgical/traumatic wound infection, and infected ulcers and burns), osteomyelitis, device-related osteoarticular infections, impetigo, secondarily infected skin lesions, meningitis, brain abscess, subdural empyema, spinal epidural abscess, arterial damage, gastritis, urinary tract infections, biliary tract infections, pyelonephritis, cystitis, sinus infections, ear infections, otitis media, otitis externa, leprosy, tuberculosis, conjunctivitis, bloodstream infections, benign prostatic hyperplasia, chronic prostatitis, lung infections including chronic lung infections of humans with cystic fibrosis, osteomyelitis, catheter infections, bloodstream infections, skin infections, acne, rosacea, dental caries, periodontitis, gingivitis, nosocomial infections, arterial damage, endocarditis, periprosthetic joint infections, open or chronic wound infections, venous stasis ulcers, diabetic ulcers, arterial leg ulcers, pressure ulcers, endocarditis, pneumonia, orthopedic prosthesis and orthopedic implant infections, peritoneal dialysis peritonitis, cirrhosis, and any other acute or chronic infection that involves or possesses a biofilm.

The infection may be caused by a drug-resistant strain of *E. coli*, the infection may present as a urinary tract infection. Optionally, the subject may be one that is hospitalized and/or is immunocompromised.

Optionally, the treatment of a microbial infection in a subject in need thereof may also include further administering one or more antimicrobial agents, such as one or more antibiotics, to the subject as previously disclosed.

III. Compounds and Compositions

A class of compounds with a broad range of activity, particularly against bacteria is disclosed, and compositions including these compounds. The compounds, which are further of this application, below, and compositions comprising one or more of the compounds, are presented herewith as a fourth aspect of the present disclosure. The compounds and compositions comprising one or more of the compounds can be used to inhibit or reduce biofilm formation on a surface, treat or prevent an infection, and kill some antibiotic resistant organisms. In one embodiment, compounds and compositions comprising one or more of the compounds, and methods and uses employing one or more of the compounds and/or compositions, for inhibiting, reducing, or preventing biofilm formation or buildup on a surface or to removing, dispersing, reducing, or eradicating biofilm on a surface are disclosed. In another embodiment, compounds and compositions comprising one or more of the compounds, and methods and uses employing one or more of the compounds and/or compositions, for the treatment of, inhibition of growth of, and inhibition of colonization by, bacteria, both in biological and non-biological environments are also disclosed. In a further embodiment, compounds and compositions comprising one or more of the compounds, and methods and uses employing one or more of the compounds and/or compositions, for disinfecting surfaces, both in biological and non-biological environments, and products that have been coated with, or treated by, one or more of the compounds and/or compositions are further disclosed. In still another embodiment, compounds and compositions comprising one or more of the compounds, and methods and uses employing one or more of the compounds and/or compositions, for potentiating the effects of one or more antibiotics, increasing the sensitivity of bacteria (including antibiotic-resistant bacteria) to one or more antibiotics, and also to reversing antibiotic resistance in bacteria are disclosed. In yet another embodiment, compounds and compositions comprising one or more of the compounds, and methods and uses employing one or more of the compounds and/or compositions, for enhancing the growth of animals and their efficiency of feed utilization, in particular by oral administration of feed and drink compositions are disclosed.

All methods and uses disclosed in Section II above may utilize one or more types of compounds as defined in this section III, including derivatives, hydrates, and salts as defined in sub-sections 1 and 2 below, respectively.

A. Compounds

The following compounds as described in this section of the application are provided herewith.

Compositions comprising, consisting essentially of, or consisting of, one or more of these compounds is also provided. These compositions may be used in all of the other various aspects, and methods and uses disclosed above which employ the compositions, and may comprise, consist essentially of, or consist of, one or more types of compound as defined in this section, including derivatives and salts as defined in sub-sections 1 and 2, respectively.

Without limitation, compounds of particular interest for use in accordance with the present invention include Fe III complexes comprising ligands bound to the iron centre selected from amino acids or α-hydroxy acids, including but not limited to ferric lactate (also referred to herein as Fe-Lac), ferric citrate (also referred to herein as Fe-Cit), ferric tartarate (also referred to herein as Fe-Tart), ferric glycinate (also referred to herein as Fe-Gly), ferric quinate (also referred to herein interchangeable as FeQ and Fe-QA), complexes of tyrosine with ferric ion such as ferric tyrosine (also referred to herein as FeTyr), complexes of ferric ion with DOPA (also referred to herein as FeDOPA), and the complex of ferric ion with phenylalanine (also referred to herein as Fe-Phe). Further, compounds which are structural and/or functional variants, derivatives and/or analogs of the foregoing compounds, as further described below in this section, are of particular interest.

The ligands that may be used in such complexes include ligands based on amino acids, α-hydroxy acids, o-hydroxy benzoic acids or pyridine-2-carboxylic acids.

Exemplary amino acids can include, but are not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, each preferably in the L-isoform although, as discussed above, in an alternative embodiment one or more (optionally all) may be in the D-isoform. Mixtures of optical isomers of the same amino acid may, or may not, be used in some embodiments.

Exemplary α-hydroxy acids include, but are not limited to, quinic acid, lactic acid, glycolic acid, citric acid, tartaric acid, malic acid, and mandelic acid.

Exemplary o-hydroxy benzoic acids include, but are not limited to, salicylic acid.

Exemplary pyridine-2-carboxylic acids include, but are not limited to, α-Picolinic acid.

In certain embodiments, compounds are Fe III complexes, which may optionally bind to MOMPs or FlaA of *Campylobacter*, wherein the Fe III complexes are represented by the following chemical Formula I:

$$Fe(III)_x(ligand)_y \qquad \text{Formula I}$$

wherein x is an integer value of 1 to 2, more preferably 1, and y is an integer value of 1 to 3 and each ligand present is independently a conjugate base of a substituted or unsubstituted α-hydroxy acid selected from citric acid, malic acid, tartaric acid, lactic acid, glycolic acid, quinic acid, glycolic, isoleucic, valic, and mandelic acid; and salts and/or hydrates thereof. In preferred embodiments, all the ligands are the same. The α-hydroxy acids listed may contain more than one carboxylic acid moiety and the term conjugate base as used herein refers to acids having at least one acidic group in a deprotonated form. In some embodiments, all the acidic groups of an α-hydroxy acid derived ligand may be deprotonated.

In yet other embodiments of the Fe complexes according to Formula I, the one or more ligands present are independently a conjugate base of a substituted or unsubstituted amino acid selected from the group consisting of glycine, alanine, arginine, asparagine, aspartic acid, cysteine, glutamine, glutamic acid, histidine, isoleucine, leucine, lysine, methionine, phenylalanine, proline, serine, threonine, tryptophan, tyrosine, and valine, wherein x and y are as previously defined; and salts and/or hydrates thereof.

In some embodiments of Formula I described above, the ratio of x:y is such that the total charge of the Fe III complexes is neutral. In certain embodiments the ligands described above are bidentate or tridentate ligands which complex the Fe(III) ion. In an alternate embodiment, the total charge of the Fe III complexes may be neutral due to the presence of an anion or cation, such as, but not limited to, hydroxide, chloride, sodium, potassium, or lithium ion. In other embodiments, the Fe complexes may crystallize incorporating one or more molecules of base.

Exemplary compounds of Fe complexes according to Formula I include, but are not limited to, the compounds shown below:

1)
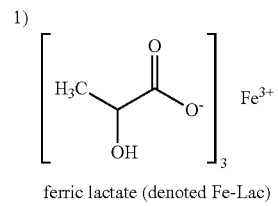
ferric lactate (denoted Fe-Lac)

2)
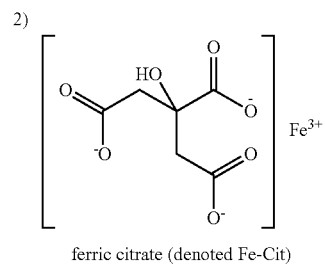
ferric citrate (denoted Fe-Cit)

3)

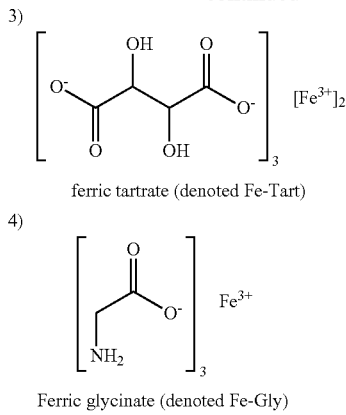

ferric tartrate (denoted Fe-Tart)

4)

$$\left[\begin{array}{c} \text{O} \\ \parallel \\ \text{C} \\ / \quad \backslash \\ \text{NH}_2 \quad \text{O}^- \end{array}\right]_3 \text{Fe}^{3+}$$

Ferric glycinate (denoted Fe-Gly)

In certain embodiments, the compounds which may bind to MOMPs or FlaA of *Campylobacter*, are Fe III complexes each containing three bidentate ligands, such as described herein.

In a further embodiment, a compound according to Formula I, may be a compound that inhibits biofilm formation by bacteria as measured in a plastic bead, wherein the bacteria is grown in a medium containing the compound to form a growth suspension of the bacteria at 0.0001 OD/ml, the growth suspension is allowed to grow with plastic coated UV beads (Lascells), and the beads are assayed after 24 hours for the presence of biofilm formation on the beads (by counting bacteria after release from the beads), and compared to a control group where the bacteria is not grown in the presence of the compound. Preferably the compound inhibits the binding of the bacteria to the plastic coated beads at a level of inhibition that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of inhibition of the binding of the bacteria to the plastic coated UV beads by either a complex of L-tyrosine with Fe III or a complex of quinic acid with Fe III at the same molar concentration. In particularly preferred embodiment, the bacteria can be *Enterococcus faecalis, Staphylococcus epidermidis, Staphylococcus aureus, Campylobacter jejuni, Pseudomonas aeruginosa*, Uropathogenic *Escherichia coli*, and Enteropathogenic *Escherichia coli*.

In a further embodiment, a compound according to Formula I may be a compound that inhibits binding of *Helicobacter pylori* to human gastric tissue (for example as determined by a method as described in Example 5) at a level of inhibition that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of inhibition of the binding of the bacteria to human gastric tissue by either a complex of L-tyrosine with Fe III or a complex of quinic acid with Fe III at the same molar concentration as measured by counting the average number of bacteria bound to the tissue.

In a further embodiment, a compound according to Formula I, may be a compound that inhibits biofilm formation of a bacteria, but does not inhibit planktonic growth of the bacteria, wherein the bacteria can be one or more of the following: *Enterococcus faecalis, Staphylococcus epidermidis, Staphylococcus aureus, Campylobacter jejuni, Pseudomonas aeruginosa*, Uropathogenic *Escherichia coli*, and Enteropathogenic *Escherichia coli*. Preferably the compounds inhibit biofilm formation (for example, as measured by coverage rate in Example 7), at a level that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of biofilm inhibition by a complex of L-tyrosine with Fe III or a complex of quinic acid with Fe III at the same molar concentration.

In a further embodiment, a compound according to Formula I, may be a compound that prevents attachment of bacteria to a surface, and the prevention of attachment of bacteria to the surface is at a level that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of bacteria attachment by a complex of L-tyrosine with Fe III or a complex of quinic acid with Fe III at the same molar concentration as measured by optical density. In particularly preferred embodiment, the bacteria can be *Enterococcus faecalis, Staphylococcus epidermidis, Staphylococcus aureus, Campylobacter jejuni, Pseudomonas aeruginosa*, Uropathogenic *Escherichia coli*, and Enteropathogenic *Escherichia coli*.

In a further embodiment, a compound according to Formula I, may be a compound that is capable of rendering an antibiotic resistant strain of bacteria sensitive to the antibiotic to which it is otherwise resistant (for example, when determined by a method that comprises immersing a patch in a solution of the compound and an antibiotic, such as kanamycin, for example at a concentration of 50 µg/mL as described in Example 9, placed on a plate with the antibiotic resistant strain (such as a kanamycin resistant strain of Enteropathogenic *Escherichia coli* or *Campylobacter jejuni*)), and causes the bacteria to fail to grow or reduces the rate of growth of the antibiotic resistant strain in the presence of the antibiotic by a level that is a level that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of reduction of the rate of growth caused by a complex of L-tyrosine with Fe III or a complex of quinic acid with Fe III at the same molar concentration.

In a further embodiment, a compound according to Formula I, for may be a compound that causes a decrease in the rate of growth to a level that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the decrease in the rate of growth measured by optical density of an antibiotic resistant bacteria when grow in the presence of the compound and the antibiotic.

In accordance with one embodiment, instead of the direct administration of the one or more compounds, it or they may be formed in vivo, by administering a suitable iron containing substance and one or more suitable ligands capable of forming the compounds in vivo with the iron compound (see: Campbell and Hasinoff, Ferrous sulfate reduces levodopa bioavailability: Chelation as a possible mechanism, *Clin. Pharmacol. Ther.* 45:220-5, 1989). For example, ferrous sulfate and tyrosine (as ligand) may be administered in order to form Fe-Tyr in vivo, ferrous sulfate and L-DOPA (as ligand) may be administered in order to form Fe-DOPA in vivo, ferrous sulfate and L-phenylalanine (as ligand) may be administered in order to form Fe-Phe in vivo or ferrous sulfate and quinic acid (as ligand) may be administered in order to from Fe-QA in vivo. In this example, $Fe^{2+}$ is oxidized to Fe' in vivo, and may complex with tyrosine, L-DOPA, or phenylalanine respectively. The compounds may also be formed in vivo from any substance that can be metabolized in vivo to the compounds. For example, phenylalanine could be administered with ferrous sulfate since it will be metabolized to tyrosine in vivo, and may then complex with the ferric iron (formed from oxidation of ferrous sulfate). Alternatively, ferric chloride could also be administered with, for example, tyrosine, quinic acid, L-DOPA and/or phenylalanine.

Optionally, one or more compounds for use in any of the first, methods disclosed above (which may or may not be compounds according to Formula I, are ligands for the major outer membrane proteins (MOMPs) or FlaA of *Campylobacter*, and/or may be capable of downregulating the expression of FlaA and/or FlaB proteins in a bacteria such as *Campylobacter*, such as to the extent of causing a reduced bacterial motility such as when determined by a method as described in Example 21 of the present application. The binding of the compounds to the MOMPs or FlaA inhibits the MOMPs or FlaA from attaching, binding, or associating with other proteins, biofilm components, surfaces or other bacteria.

The compound can be a mimetic or synthetic human histo-blood group antigen or a synthetic sugar. A synthetic human histo-blood group antigen may be a sugar, for example a saccharide having the same structure as a natural human histo-blood group antigen such as for example H-I antigen, H-II antigen, Lewis antigen, $Le^b$, $Le^x$ or $Le^y$. A preferred compound is ferric quinate (Fe-QA).

The compounds provided herein which bind to MOMPs or FlaA of *Campylobacter* include compounds with structures described in this section, in accordance with Formulae A or B, or further compounds as described below. It has been demonstrated that these compounds inhibit both gram negative bacteria, such as *Pseudomonas aeruginosa, Campylobacter jejuni, Helicobacter pylori, Escherichia coli*, Enteropathogenic *Escherichia coli* (EPEC), Uropathogenic *Escherichia coli* (UPEC) and gram positive bacteria, such as *Staphylococcus epidermidis, Staphylococcus aureus*, and *Enterococcus faecalis*, which are believed to be predictive of efficacy with other species There is low homology between the MOMP of *Campylobacter* and other bacteria. It is believed that the compounds interact with several surface porin-like bacterial proteins that have not yet been identified on other bacteria.

In the case of compounds which are Fe III complexes comprising ligands bound to the iron centre, in one option not all ligands will be the same in the compositions comprising the Fe III complex compounds. Therefore, for example, in a composition comprising an Fe III complex as described above, it may be that less than 100% of the Fe III ligands are identical, although preferably at least 50%, 60%, 70%, 80%, 85%, 90%, 91%, 92%, 93%, 94%, 95%, 96%, 97%, 98%, or 99% of the ligands in the composition are identical. In that context, in one embodiment the term "identical" discriminates between enantiomeric forms of ligand, that is, different enantiomers are not identical; whereas, in another embodiment, the term "identical" can be applied to different enantiomeric forms of ligand, that is, optionally different enantiomeric forms of the same ligand are considered to be identical.

1. Derivatives

Derivatives of the compounds may also be used. The term "derivative" does not mean that the derivative is synthesized from the parent compound either as a starting material or intermediate, although this may be the case. The term "derivative" can include salts (for example, pharmaceutically acceptable salts), prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds having one or more amino substituents or hydrogen groups replaced with substituted or unsubstituted alkyl, aminoalkyl, aryl, or heteroaryl groups having from 1 to 30 carbon atoms.

2. Salts

The compounds of the Formulae described herein such as the compounds defined above, can be in the form of a salt, for example, a pharmaceutically acceptable salt. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids and inorganic or organic bases. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts, and bases such as lithium hydroxide, sodium hydroxide, potassium hydroxide and ammonium hydroxide.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

B. Antimicrobial Agents

Antimicrobial agents that may be used therapeutically and/or non-therapeutically with the compounds disclosed herein above, for example for the treatment or prophylaxis of microbial infection in the methods disclosed above either separately, simultaneously or sequentially, include, but are not limited to: (i) Aminoglycosides, including amikacin, gentamicin, kanamycin, neomycin, netilmicin, tobramycin, paromomycin, streptomycin, spectinomycin; (ii) Ansaycins, including geldanamycin, herbimycin, rifaximin, (iii) Carbacephem, including loracarbef, (iv) Carbapenems, including ertapenem, doripenem, imipenem/cilastatin, meropenem, (v) Cephalosporins, including cefadroxil, cefazolin, cefalotin or cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, (vi) Glycopeptides, including teicoplanin, vancomycin, telavancin, dalbavancin, oritavancin, (vii) Lincosamides, including clindamycin, lincomycin, (viii) Lipopeptides including daptomycin, (ix) Macrolides including azithromycin, clarithromycin, dirithromycin, erythromycin, roxithromycin, troleandomycin, telithromycin, spiramyin, (x) Monobactams, including aztreonam, (xi) Nitrofurans, including furazolidone, nitrofurantoin, (xii) Oxazolidinones, including linezolid, posizolid, radezolid, torezolid, (xiii) Penicillins, including amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, peperacillin/tazobactam, ticarcillin/clavulanate (xiv) Polypeptides including bacitracin, colistin, polymyxin B, (xv) Quinolones/Fluoroquinolone, including ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, (xvi) Sulfonamides, including mafenide, sulfacetamide, sulfadiazine, silver sulfadiazine, sulfadimethoxine, sulfamethizole, sulfamethoxazole, sulfanilamide, sulfasalazine, sulfisoxazole, trimethoprim-sulfamethoxazole(co-trimoxazoale), sulfonamidochrysoidine, (xvii) Tetracyclines, including demeclocycline, doxycycline, minocycline, oxytetracycline, tetracycline, (xviii) clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim; and combinations thereof. The compounds may also be combined with triclosan and chlorhexidine. Other antimicrobial agents include: aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes.

C. Excipients and Carriers

The compounds above can be formulated for use in any of the methods disclosed above, and may, for example, be formulated in a way that is suitable for enteral, parenteral, topical, or pulmonary administration.

The compounds above can be combined with one or more pharmaceutically acceptable carriers and/or excipients that are considered safe and effective and may be administered to an individual without causing undesirable biological side effects or unwanted interactions.

The carrier can include all components present in the pharmaceutical formulation other than the active ingredient or ingredients. The compounds are included in the formulation in an effective amount to achieve the desired effect, for example in an amount that is effective to inhibit biofilm formation or reduce biofilm buildup. An effective amount of a compound provided to a subject may be an amount that is enough to provide the required degree of reduction of microbial colonization. This may depend on the type of compound and/or the size of the animal.

In one embodiment an effective amount of the compound may be an amount that is effective to deliver the compound to the site at which action is required in a concentration that ranges from 1 µm to 1 M, preferably greater than 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM, 200 µM or more. A suitable concentration may be within the range of about 1 µm to about 1 mM, or about 30 µm to about 0.5 mM, or about 60 µM to about 0.3 mM. These concentrations may particularly apply in the context of the second and/or third aspects of the present disclosure.

In a further embodiment an effective amount of the compound may be 0.3 to 32 mg/day/kg bodyweight of the subject such as a chicken. In another embodiment an effective concentration of the compound may be between 0.001 to 1 mM for use in coatings or devices, or solutions.

The compounds can also be formulated for use as a disinfectant, for example, in a hospital environment or for industrial application.

1. Parenteral Formulations

The compounds above may be formulated for parenteral administration for use in the methods disclosed above.

Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium ions of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® (triblock copolymer of polyoxyethylene, followed by a block of polyoxypropylene, followed by a block of polyoxyethylene) 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers. It is to be noted that FeQ and some of the other compounds of the application are acidic, and so advantageously are formulated with a buffer in order to achieve a suitable pH, particularly in the context of preparing injectable formulation, including formulations for intravenous injection.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

(a) Controlled Release Formulations

The parenteral formulations described herein comprising one or more compounds above may be formulated for controlled release including immediate release, delayed release, extended release, pulsatile release, and combinations thereof.

1. Nano- and Microparticles

For parenteral administration, the one or more compounds and optionally one or more additional active agents, can be incorporated into microparticles, nanoparticles, or combinations thereof that provide controlled release of the compounds and/or one or more additional active agents. In embodiments wherein the formulations contains two or more active components, such as drugs, then they can be formulated for the same type of controlled release (e.g., delayed, extended, immediate, or pulsatile) or they can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the active agent(s). Release of the active agent (s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyesters, such as polylactide (PLA), polyglycolide (PGA), poly(lactide-co-glycolide) (PLGA), polydioxanone, poly-3-hydroxybutyrate (PHB) and copolymers thereof, poly-4-hydroxybutyrate (P4HB) and copolymers thereof, polycaprolactone and copolymers thereof, polymers including, but not limited to, polymers of glycolic acid, lactic acid, 1,4-dioxanone, trimethylene carbonate, 3-hydroxybutyric acid, 4-hydroxybutyrate, e-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly (orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly (alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone and copolymers thereof, including random copolymers and block copolymers thereof. and combinations thereof.

Alternatively, the active agent can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name STEROTEX®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of active agent containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

2. Method of Making Nano- and Microparticles

Encapsulation or incorporation of active agent, such as the one or more compounds into carrier materials to produce drug-containing microparticles can be achieved through known pharmaceutical formulation techniques. In the case of formulation in fats, waxes or wax-like materials, the carrier material is typically heated above its melting temperature and the active agent is added to form a mixture comprising active agent particles suspended in the carrier material, active agent dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, active agent is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce active agent-containing microparticles. In this case active agent and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, active agent in a particulate form is homogeneously dispersed in a water-insoluble or slowly water soluble material. To minimize the size of the active agent particles within the composition, the active agent powder itself may be milled to generate fine particles prior to formulation. The process of jet milling, known in the pharmaceutical art, can be used for this purpose. In some embodiments active agent in a particulate form is homogeneously dispersed in a wax or wax like substance by heating the wax or wax like substance above its melting point and adding the active agent particles while stirring the mixture. In this case a pharmaceutically acceptable surfactant may be added to the mixture to facilitate the dispersion of the active agent particles.

The particles can also be coated with one or more modified release coatings. Solid esters of fatty acids, which are hydrolyzed by lipases, can be spray coated onto microparticles or active agent particles. Zein is an example of a naturally water-insoluble protein. It can be coated onto active agent containing microparticles or active agent particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding active agent containing microparticles or active agent particles, a water-soluble protein can be spray coated onto the microparticles and subsequently cross-linked by the one of the methods described above. Alternatively, active agent-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

(b) Injectable/Implantable Formulations

The one or more compounds above can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods. Further alternative polymers for use in this context include polymers include, but are not limited to, polymers of glycolic acid, lactic acid, 1,4-dioxanone, trimethylene carbonate, 3-hydroxybutyric acid, 4-hydroxybutyrate, e-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolcatone and copolymers thereof, including random copolymers and block copolymers thereof.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

2. Enteral Formulations

The compounds above may be formulated for enteral administration.

Suitable oral dosage forms include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

(a) Controlled Release Enteral Formulations

Oral dosage forms, such as capsules, tablets, solutions, and suspensions, can be formulated for controlled release, for example, for the controlled release of the one or more compounds above. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the active agent and a controlled release polymer or matrix. Alternatively, the active agent particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

(1) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and CARBOPOL® 934 (cross-linked polyacrylate polymer), polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT®. In further preferred embodiments, the acrylic polymer comprises a mixture of two acrylic resin lacquers commercially available from Rohm Pharma under the trade names EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(2) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating an active agent or an active agent-containing composition with a selected coating material. The active agent-containing composition may be, e.g., a tablet for incorporation into a capsule, a tablet for use as an inner core in a "coated core" dosage form, or a plurality of active agent-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 3 wt. % to 50 wt. %", or 10 wt % to 50 wt. %, relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Topical Formulations

The compounds as defined in section III. may be formulated for topical administration and use in the methods disclosed herein.

The formulations may contain the one or more compounds discussed above, alone or in combination, in an effective amount to prevent or inhibit biofilm formation on a surface, or reduce the amount of biofilm on a surface being treated. 1000 colony forming units (cfu) of *Campylobacter* are enough to infect a human and cause disease in a human.

Therefore, in one embodiment, an effective amount of the one or more compounds of this application is, or are, enough of the compound(s), alone, or in combination with other compounds, to reduce the number of cfu of *Campylobacter* or other microorganism of interest on the surface being treated to a number that is unlikely to, or which will not, cause infection in humans.

Suitable dosage forms for topical administration include creams, ointments, salves, sprays, gels, lotions, irrigants, and emulsions.

"Buffers" are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, *ceratonia* extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

(a) Emulsions

An emulsion is a preparation of one liquid distributed in small globules throughout the body of a second liquid. In particular embodiments, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These delivery systems are typically capsules (hard shell or soft shell) comprised of the compound dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

(b) Lotions

A lotion can contain finely powdered substances that are insoluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

(c) Creams

Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

(d) Ointments

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy than ointments prepared with the same components.

(e) Gels

Gels are semisolid systems containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkylene glycols, such as propylene glycol; dimethyl isosorbide; alcohols, such as isopropyl alcohol and ethanol. The solvents are typically selected for their ability to dissolve the compound. Other additives, which improve the skin feel and/or emolliency of the formulation, may also be incorporated. Examples of such additives include, but are not limited to, isopropyl myristate, ethyl acetate, $C_{12}$-$C_{15}$ alkyl benzoates, mineral oil, squalane, cyclomethicone, capric/caprylic triglycerides, and combinations thereof.

(f) Foams

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

4. Disinfecting and Cleaning Formulations

The compounds above may be formulated into cleaning formulations.

The cleaning formulations include formulations that are highly efficacious for household cleaning applications (e.g., hard surfaces like floors, countertops, tubs, tile, dishes and softer cloth materials like clothing, sponges, paper towels, etc.), personal care applications (e.g. lotions, shower gels, soaps, shampoos, sprays, wipes, toothpaste, acne treatments, skin cleansers, mouthwash, wound irrigation solutions, towelettes, contact lenses and lens cases) and industrial and hospital applications (e.g., antifouling coatings, and disinfection of instruments, medical devices, gloves, filters, membranes, tubing, drains, pipes including gas pipes, oil pipes, drilling pipes, fracking pipes, sewage pipes, drainage pipes, hoses, animal carcasses, fish tanks, showers, children's toys, boat hulls, and cooling towers). These formulations are efficacious for cleaning surfaces which are infected or contaminated with biofilm or for preventing the formation of biofilm on these surfaces.

The compounds can be formulated into a solution in a suitable solvent for administration in a spray bottle, the compounds can be formulated as an aerosol, as a foam, suitable for spraying onto surfaces, or, they can be imbibed into a cloth or other item suitable for wiping down a surface to be disinfected. Methods for making formulations for use as a disinfectant in the forms are known in the art.

One embodiment provides the compounds or a derivative thereof in a composition containing a pH dye indicator and an alkaline substance. The pH indicator dye indicates what surface has been disinfected and ensures that a sufficient time has passed to disinfect the surface. See for example, U.S. Publication No. 20140057987.

Cleaning formulations can include the compounds and an acceptable carrier. The carrier can be in a wide variety of forms. For example, the carrier may be an aqueous-based solution or cleanser, an alcohol-based solution or gel or an emulsion carrier, including, but not limited to, oil-in-water, water-in-oil, water-in-oil-in-water, and oil-in-water-in-silicone emulsions. The carrier solution containing the compound(s) can be applied directly to the surface to be treated or delivered via a suitable substrate.

The cleaning formulations can be formulated for use on the skin. In these embodiments the compounds can be formulate in a dermatologically acceptable carrier. The dermatologically acceptable carriers can also be, for example, formulated as alcohol or water based hand cleansers, toilet bars, liquid soaps, shampoos, bath gels, hair conditioners, hair tonics, pastes, or mousses.

Cleaning formulations can contain one or more surfactants. The surfactant is suitably selected from anionic, nonionic, zwitterionic, amphoteric and ampholytic surfactants, as well as mixtures of these surfactants. Such surfactants are well known to those skilled in the detergency art. Non limiting examples of possible surfactants include isoceteth-20, sodium methyl cocoyl taurate, sodium methyl oleoyl taurate, and sodium lauryl sulfate. Examples of a broad variety of additional surfactants are described in McCutcheon's Detergents and Emulsifiers. North American Edition (1986), published by Allured Publishing Corporation. The cleansing formulations can optionally contain, at their art-established levels, other materials which are conventionally used in cleansing formulations.

Additional carriers suitable for the cleaning formulations may include various substrate-based products. In such instances, the present formulations may be impregnated into or onto the substrate products and may be allowed to remain wet or may be subjected to a drying process. For instance, suitable carriers include, but are not limited to, dry and wet wipes suitable for personal care and household use (e.g., nonwoven baby wipes, household cleaning wipes, surgical preparation wipes, etc.); diapers; infant changing pads; dental floss; personal care and household care sponges or woven cloths (e.g., washcloths, towels, etc.); tissue-type products (e.g. facial tissue, paper towels, etc.); and disposable garments (e.g., gloves, smocks, surgical masks, infant bibs, socks, shoe inserts, etc.). Cleaning formulations can be incorporated into various household care products including, but not limited to, hard surface cleaners (e.g., disinfectant sprays, liquids, or powders); dish or laundry detergents (liquid or solid), floor waxes, glass cleaners, etc.

Exemplary carriers can include aqueous solutions, e.g. having from about 0% to about 98.8%, by weight of the composition, of water. Additionally, carriers may contain an aqueous alcohol solution. The amount of alcohol present in the alcohol solution will vary depending on the type of product in which the composition is incorporated, i.e. say a wipe where the preferred amount of alcohol present would be from about 0% to about 25% whereas a hand sanitizer preferably contains from about 60% to about 95%, of alcohol. Therefore, suitable dermatologically acceptable alcohol solutions or gels may contain from about 0% to about 95%, by weight of the composition, of an alcohol.

Alcohols suitable for inclusion in the alcohol solutions of the carrier include, but are not limited to, monohydric alcohols, dihydric alcohols, and combinations thereof. More preferred alcohols are selected from the group consisting of monohydric linear or branched C2-C18 alcohols. The most preferred alcohols are selected from the group consisting of ethanol, isopropanol, n-propanol, butanol, and combinations thereof. The cleaning formulations which contain an alcohol solution may be anhydrous or water containing.

Thickeners can be added to the water or alcohol based to form a gel. Examples of suitable thickeners include, but are not limited to, naturally-occurring polymeric materials such as sodium alginate, xanthan gum, quince seed extract, tragacanth gum, starch, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, and polyvinylidene chloride polymers. Inorganic thickeners may also be used such as aluminum silicates, such as, for example, bentonites, or a mixture of polyethylene glycol and polyethylene glycol stearate or distearate.

The cleaning formulations can contain, in addition to the compounds described above, one or more antimicrobial or antifungal agents. Such agents are capable of destroying microbes, preventing the development of microbes or preventing the pathogenic action of microbes. Examples of additional antimicrobial and antifungal agents include β-lactam drugs, quinolone drugs, ciprofloxacin, norfloxacin, tetracycline, erythromycin, amikacin, 2,4,4'-trichloro-2'-hydroxy diphenyl ether (TRICLOSAN®), phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, pyrithiones (especially zinc pyrithione which is also known as ZPT), dimethyldimethylol hydantoin (GLYDANT®), methylchloroisothiazolinone/methylisothiazolinone (KATHON CG®), sodium sulfite, sodium bisulfite, imidazolidinyl urea (Germall 115®), diazolidinyl urea (GERMAILL II®), benzyl alcohol, 2-bromo-2-nitropropane-1,3-diol (BRONOPOL®), formalin (formaldehyde), iodopropenyl butylcarbamate (POLYPHASE P100®), chloroacetamide, methanamine, methyldibromonitrile glutaronitrile (1,2-Dibromo-2,4-dicyanobutane or TEKTAMER®), glutaraldehyde, 5-bromo-5-nitro-1,3-dioxane (BRONIDOX®), phenethyl alcohol, o-phenylphenol/sodium o-phenylphenol, sodium hydroxymethylglycinate (SUTTOCIDE A®), polymethoxy bicyclic oxazolidine (NUOSEPt C®), dimethoxane, thimersal dichlorobenzyl alcohol, captan, chloφphenenesin, dichlorophene, chlorbutanol, glyceryl laurate, halogenated diphenyl ethers like 2,4,4'-trichloro-2'-hydroxy-diphenyl ether (TRICLOSAN® or TCS), 2,2'-dihydroxy-5,5'-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl pPhenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethy 1-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol, 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol (PCMX), chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4'-chloro 2,4-dihydroxydiphenyl methane, 5-bromo 2,4-dihydroxydiphenyl methane, and 4'-bromo 2,4-dihydroxydiphenyl methane, bisphenolic compounds like 2,2'-methylene bis (4-chlorophenol), 2,2'-methylene bis (3,4,6-trichlorophenol), 2,2'-methylene bis (4-chloro-6-bromophenol), bis (2-hydroxy-3,5-dichlorophenyl) sulphide, and bis (2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4'-trichlorocarbanilides (TRICLOCARBAN® or TCC), 3-trifluoromethyl-4,4'-dichlorocarbanilide, 3,3',4-trichlorocarbanilide, etc.), cationic actives such as benzalkonium chloride, and clotrimazole. Another class of antimicrobial agents (specifically antibacterial agents) which are useful, are the so-called "natural" antibacterial actives, referred to as natural essential oils. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, *eucalyptus*, vervain, peppermint, gum benzoin, basil, fennel, fir, balsam, menthol, ocmea *origanum*, Hydastis carradensis, Berberidaceae daceae, Ratanhiae and *Curcuma longa*.

The cleaning formulations may be packaged in a variety of suitable packaging known to those skilled in the art. The liquid formulations may desirably be packaged in manually operated spray dispensing containers, which are usually made of synthetic organic polymeric plastic materials. Accordingly, disinfecting formulations containing the compounds and packaged in a spray dispenser, preferably in a trigger spray dispenser or a pump spray dispenser, are envisioned. Spray-type dispensers allow to uniformly apply to a relatively large area of a surface to be disinfected a liquid cleaning formulations described herein.

The compounds can be impregnated into a nonwoven absorbent wipe. Disinfectant wet wipes are also disclosed for example in U.S. Pat. No. 8,563,017.

The compounds can be in an aqueous foam with a special surfactant system capable of generating a foam. See U.S. Pat. Nos. 8,097,265, 5,891,922 and 4,889,645.

The compounds can also be in a pressurized spray aerosol. See also, U.S. Publication No. 20010053333 which discloses a liquid flash-dry aerosol disinfectant composition with a flash vaporization component and an effective amount of an antimicrobial agent.

It is within the abilities of one of ordinary skill in the art to determine the effective amount of the compounds to include in an aerosol, foam, solution or disinfectant cloth for the purpose of sterilizing for example, high risk hospital surfaces.

D. Conjugation and Immobilization of Compounds

The one or more compounds may be presented as conjugated and/or immobilized compounds. The compounds may be conjugated with other agents in order to retain the compounds on surfaces, for example, to prevent biofilm formation on a surface. In one embodiment, the compounds may be conjugated to an agent that has affinity for a surface in order to retain the compounds on that surface. For example, the compounds may be conjugated to an agent wherein the agent is a polymer or oligomer, and the polymer or oligomer has a high affinity for the surface.

In another embodiment the compounds may be conjugated to an agent wherein the agent comprises a reactive moiety suitable for anchoring to a surface. The reactive moiety may, for example, be photo-reactive, or capable of coupling covalently to a surface. The reactive moiety may also incorporate spacers and linkers and other functional groups in order to place the compound in a desired location relative to the surface. Examples of how compound may be conjugated to an agent comprising a reactive moiety suitable for anchoring to a surface are shown below.

In the examples, FeQ is conjugated to a calix[4] arene frame that comprises a reactive moiety. In a first example, FeQ is conjugated via a linker to a calix[4] arene frame that contains a photoreactive functional group. A second example shows that the reactive moiety can be positioned at a different location on the calix[4] arene frame. A third example shows FeQ conjugated to a calix[4] arene frame, wherein the latter is functionalized with thiol groups that are capable of reacting with surfaces. It should be understood that different linkers or no linkers may be used, and that other agents may be used instead of the calix[4] arene frame, including cyclodextrins and other polymers and oligomers.

In yet another embodiment, the compounds may be conjugated to an agent that comprises a substance with an affinity for a surface. The agent may incorporate spacers and linkers and other functional groups in order to place the compound in the desired location relative to the surface. In one embodiment, the agent contains hydroxyapatite.

Examples of how the compounds may be conjugated via a linker to hydroxyapatite are shown below. For example, the linkers are attached in different positions to one of the quinic acid ligands via a functional group, Y', and at the other end of the linker are attached to hydroxyapatite (HA) via a second functional group, X'. In an alternative embodiment, the HA group may be replaced with a reactive group that can attach (or be attached) to a surface, such as a photo-reactive compound, isocyanate, hydroxy group, amine, trialkoxysilyl ether, such as a triethoxysilyl ether, or phosphate ester. These groups may be attached directly to the polyethylene glycol, or an additional linker inserted between the reactive group and the polyethylene glycol.

E. Feeds and Feed Supplements

The compounds can be formulated into growth promoting formulations, for example, in an animal feed or formula to improve the growth of the animal. The one or more compounds may be added to drinking water for any of the animals to improve growth The compounds may be useful in treatment of ponds, tanks, or other aquatic or marine environments containing fish (include freshwater and saltwater fish, farmed fish and ornamental fish), other marine and aquatic animals, including shellfish or crustaceans such as shrimp, oysters, mussels, clams, prawns, lobsters, crayfish, crabs, cuttlefish, octopus and crawfish.

The one or more compounds may be used alone or in combination with other anti-microbial, bactericidal or bacteriostatic compounds and/or growth enhancing agents.

The compounds can improve growth performance, and can be used to increase average body weight during growth. The compounds can also be used to improve feed conversion ratio. In particular, the compounds can be used to decrease the mortality adjusted feed conversion ratios (MFCR). The compounds may be used to produce animals with higher average body weight in a given period of time, or may be used to reach a target average body weight in a shorter period of time. The compounds may be used to decrease the amount of feed necessary for an animal to attain a target weight. In addition, the compounds may be used in stressed environments to improve growth and MFCR. These environments include but are not limited to high stocking densities of animals, dirty pen litter, presence of pathogens, presence of *Campylobacter* and other bacteria, and high temperature environments.

The compositions are particularly useful in feeds for commercial birds such as chickens, turkeys, pheasants, and ducks. Exemplary poultry feeds in which the compounds can be included, include poultry feeds that are referred to as "complete" feeds, because they are designed to contain all the protein, energy, vitamins, minerals, and other nutrients necessary for proper growth, egg production, and health of the birds. Feeding any other ingredients, mixed with the feed or fed separately, upsets the balance of nutrients in the "complete" feed. Feeding additional grain or supplement with the complete poultry feed is not recommended.

F. Treatment to Promote Growth

As discussed above in more detail above, it has been discovered that the one or more compounds of this application, above, are particularly useful in promoting growth. The compounds may be added to animal feed or animal drinking water in order to promote growth. Addition of the compounds to feed or drinking water results in improved growth. It has also been discovered that the compounds can be added to animal feed or animal drinking water in order to decrease the mortality adjusted feed conversion ratio. Thus it is possible to use the compounds to decrease the amount of feed necessary for an animal to grow. The compounds may further be administered with other animal additives, and may be administered in commercial feeds. In a preferred embodiment, the compounds are administered in feeds.

It has also been discovered that the compounds can be administered to animals that are in a stressed environment in order to improve their growth performance. In a stressed environment the compounds promote growth that yields animals with higher average body weights. The compounds also decrease mortality adjusted feed conversion ratios in stressed environments.

EXAMPLES

Example 1. Efficacy of FeQ and FeTyr to Reduce *Campylobacter* Carriage in Chickens and Promote Growth in Chickens Materials and Methods A study was performed to evaluate growth promotion and reduction of *Campylobacter* carriage using FeQ and FeTyr in Ross 308 male broilers with 7 treatment groups. Each treatment group comprised four replicates of 10 birds per pen (40 birds/treatment group and 4 pens of 10 birds/treatment group), with 2 control groups and 5 test groups. All the test groups and one of the control groups were exposed at day 20 of the trial to dirty litter, which tested positive for *Campylobacter*. This method was used to provide a more natural method to *Campylobacter* challenge the birds. Thus there was a positive control where one treatment group was challenged with *Campylobacter* and one negative control group where the birds were not challenged, and five treatment groups that were all challenged with *Campylobacter*. The total number of birds used in the 7 treatment groups was 280. Details of the treatments are provided in Table 1. Treatment group 1 was a negative control where birds just received the commercial feed, and were not challenged with dirty litter containing *Campylobacter*. Treatment group 2 was the positive control where the birds received the commercial feed, and were challenged with dirty litter containing *Campylobacter* at day 20. Treatment group 3 received 0.22 g/L of FeQ in their drinking water and 0.22 g/Kg FeQ in their feed during the entire trial, and was challenged with dirty litter containing *Campylobacter* at day 20. Treatment group 5 received 0.22 g/L of FeQ in their drinking water during the entire trial, and was challenged with dirty litter containing *Campylobacter* at day 20. Treatment group 6 received 0.22 g/kg FeQ in their feed during the entire trial, and was challenged with dirty litter containing *Campylobacter* at day 20. Treatment group 7 received 0.022 g/L FeQ in their drinking water during the entire trial, and was challenged with dirty litter containing *Campylobacter* at day 20. Treatment group 8 received 0.02 g/L FeTyr in their drinking water during the entire trial, and was challenged with dirty litter containing *Campylobacter* at day 20. The FeTyr was pre-dissolved in DMSO, and diluted to provide a solution of 0.02 g/L of FeTyr in water. (An additional treatment group 4 was terminated due to solubility issues.)

TABLE 1

Treatment Details

| Treatment | Description | *Campylobacter* Challenge |
|---|---|---|
| 1 | Control -1 Commercial feed | No |
| 2 | Control -2 Commercial feed | Yes |
| 3 | 0.22 g/L FeQ in water + 0.22 g/kg FeQ in feed | Yes |
| 5 | 0.22 g/L FeQ in water | Yes |
| 6 | 0.22 g/kg FeQ in feed | Yes |
| 7 | 0.022 g/L FeQ in water | Yes |
| 8 | 0.02 g/L FeTyr in water | Yes |

The birds were fed with a commercial three-phase feeding program using starter, grower and finisher feeds with formulations shown in Table 2. All diets had coccidiostat (MAXIBAN® at 0.0625% in starter and finisher phase diets and MONTEBAN® at 0.06% in finisher phase). Xylanase (RONOZYME® WX at 200 g per ton) and phytase (RONOZYME® P at 150 grams per ton) were added to all diets.

TABLE 2

Basal feed formulation for starter, grower and finisher diets

| Raw Material | STARTER % | GROWER % | FINISHER % |
|---|---|---|---|
| Barley | 10.5 | 8.4 | 7.2 |
| Wheat | 50.0 | 55.0 | 60.0 |
| Soya Ext Hipro | 26.0 | 23.0 | 19.0 |
| Full fat Soya Cherwell | 5.0 | 5.0 | 5.0 |
| L Lysine HCl | 0.40 | 0.30 | 0.30 |
| DL-methionine | 0.40 | 0.35 | 0.30 |
| L-threonine | 0.15 | 0.15 | 0.15 |
| Soya Oil | 4.0 | 4.50 | 4.75 |
| Limestone | 1.25 | 1.25 | 1.25 |
| MonoCal phosphate | 1.50 | 1.25 | 1.25 |
| Salt | 0.25 | 0.25 | 0.25 |
| Sodium bicarbonate | 0.15 | 0.15 | 0.15 |
| Broiler Premix | 0.40 | 0.40 | 0.40 |
| Nutrient | Analysis | Analysis | Analysis |
| Fat (ether extract) | 6.34 | 6.85 | 7.11 |
| Protein | 21.85 | 20.64 | 19.14 |
| Fibre | 3.08 | 3.02 | 2.97 |
| Ash | 6.01 | 5.68 | 5.50 |
| ME-P | 12.78 | 13.04 | 13.22 |
| Total lysine | 1.45 | 1.28 | 1.17 |

TABLE 2-continued

Basal feed formulation for starter, grower and finisher diets

| | | | |
|---|---|---|---|
| Available lysine | 1.35 | 1.19 | 1.09 |
| Methionine | 0.69 | 0.62 | 0.55 |
| Total methionine and cysteine | 1.03 | 0.95 | 0.85 |
| Threonine | 0.91 | 0.86 | 0.79 |
| Tryptophan | 0.25 | 0.23 | 0.21 |
| Calcium | 0.95 | 0.91 | 0.89 |
| Phosphorus | 0.72 | 0.66 | 0.65 |
| Available phosphorus | 0.48 | 0.42 | 0.42 |
| Salt | 0.30 | 0.30 | 0.30 |
| Sodium | 0.17 | 0.17 | 0.17 |
| Vit A | 13.20 | 13.5 | 13.50 |
| Vit D3 | 5.0 | 5.0 | 5.00 |
| Vit E | 100 | 100 | 100 |

The feeding program is show in Table 3. The birds were reared in floor pens to day 42, and fed starter, grower and finisher feed at day 0 to 11, 11 to 24, and 24 to 42 days, respectively. All birds were weighed individually and feed weigh backs recorded per pen at day 0, 11, 21, 24 and 42 days.

TABLE 3

Feeding Program

| Feeding Phase | Starter | Grower | Finisher |
|---|---|---|---|
| (days of age) | 0-11 | 11-24 | 24-42 |

Prior to challenging the chickens with dirty litter containing Campylobacter at day 20, each pen was tested for Campylobacter using cloacal swabs. All pens tested negative for Campylobacter prior to the challenge. At day 20, litter, which was naturally Campylobacter-contaminated, was tested to confirm the presence of Campylobacter, and then added (approximately 2 kg/pen) to the litter in all pens except in pens for treatment group 1 (the negative control). At day 28, the pen litter was sampled to confirm the presence or absence of Campylobacter. At day 41 and 42, caecal samples were taken from 3 birds per pen (12 birds per treatment group) and tested for Campylobacter enumeration. At day 42, digesta, fecal samples, and caecal content was taken from all birds, and pooled per pen. Two birds per pen were also taken from treatment groups 1-3, euthanized, and blood samples taken. Samples were analyzed for blood chemistry, including analysis for alkaline phosphatase, aspartate amino transferase, alanine amino transferase, gamma-glutamyl transferase, lactate dehydrogenase, total protein, albumin, globulin, amylase and glucose.

In order to minimize risk of cross-contamination, standard industry biosecurity measures were used including: disinfecting boots, changing overshoes and gloves between pens/treatments, entering Campylobacter negative pens before entering Campylobacter positive pens, and leaving adjacent pens empty. Daily health, culls, and mortality were recorded. All bird weights were recorded at 0, 11, 21, 24, 33 and 42 days. Weight gains, feed intake and feed conversion ratio (FCR) were derived for each feeding period.

Results

Tables 4-13 show the effects on the treatment groups compared to the negative control group (treatment group 1) and the positive control group (treatment group 2) for the periods 0-11 days, 11-20 days, 20-25 days, 11-25 days, 25-42 days, 20-42 days, 0-20 days, and 0-42 days.

FIG. 1 shows the average body weight at day 42 for all treatment groups, and a comparison to a commercial control labeled "Target". The figure shows that treatment group 1 (the negative control labeled "CNC") attained an average body weight (ABW) of 3.437 kg at day 42 (which was higher than the commercial target of 2.979 kg). The positive control (labeled "CC"), which was challenged with dirty litter containing Campylobacter at day 20, in contrast only attained an ABW of 3.186 kg at day 42, which was significantly less than the negative control (treatment group 1). This result demonstrates that challenging with dirty litter contaminated with Campylobacter resulted in a reduction of growth of the chicken by an average of 251 grams. However, when the chickens were challenged with dirty litter containing Campylobacter but treated with FeQ or FeTyr in treatment groups 3, 5, 6, 7 and 8, all treatment groups performed better than the positive control, demonstrating that FeQ and FeTyr treatment had a positive effect on growth. In fact, FeQ in feed at 0.22 g/kg (treatment group 6) produced chicken with an ABW of 3.464 kg, which was higher than the negative control ABW of 3.437 kg even though treatment group 6 had been challenged with dirty litter containing Campylobacter.

Figure 2:
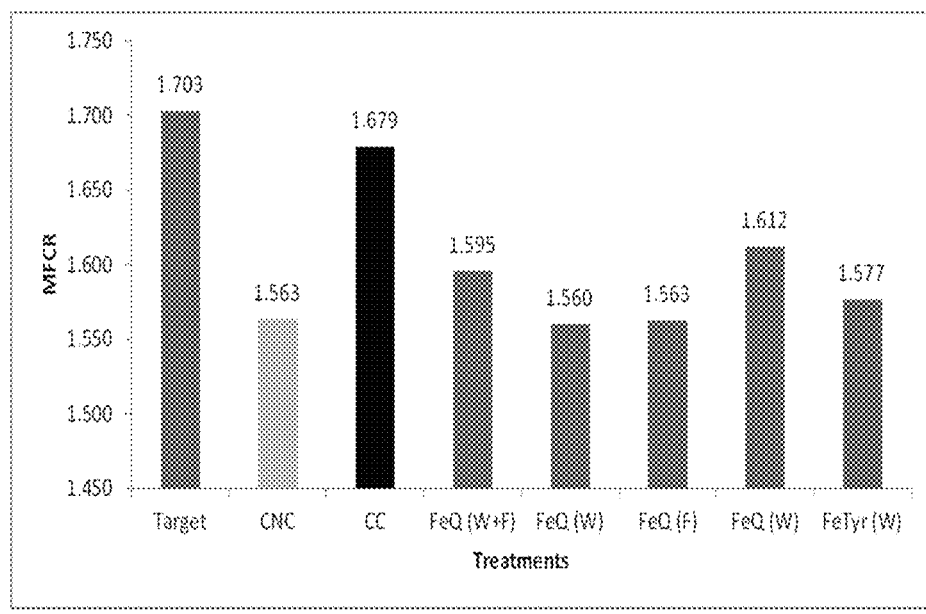
FIG. 2 is a bar graph of the mortality adjusted feed conversion rate (MFCR) at day 42 for all chicken treatment groups described in Example 1, and a comparison to a commercial control labeled "Target".

FIG. 2 shows the mortality adjusted feed conversion rate (MFCR) at day 42 for all treatment groups, and a comparison to a commercial control labeled "Target". (A lower MFCR number is a better result.) The figure shows that treatment group 1 (the negative control labeled "CNC") had a MFCR of 1.563, which was lower than the commercial target of 1.703. The positive control, labeled "CC" which was challenged with the dirty litter containing Campylobacter at day 20 had a significantly higher MFCR of 1.679 than the negative control. Thus challenging with dirty litter infected with Campylobacter resulted in a higher MFCR. However, when the chickens were challenged with dirty litter infected with Campylobacter but treated with FeQ or FeTyr in treatment groups 3, 5, 6, 7 and 8, all treatment groups performed better than the positive control demonstrating that FeQ and FeTyr treatment had a positive effect on MFCR (i.e. decreasing the numerical MFCR). The results show that treatment groups 3, 5, 6, 7 and 8 had MFCR values of 1.595, 1.560, 1.563, 1.612 and 1.577, respectively. Furthermore, treatment groups 5 and 6 performed as well as the negative control even when challenged with dirty litter containing Campylobacter.

Figure 3:
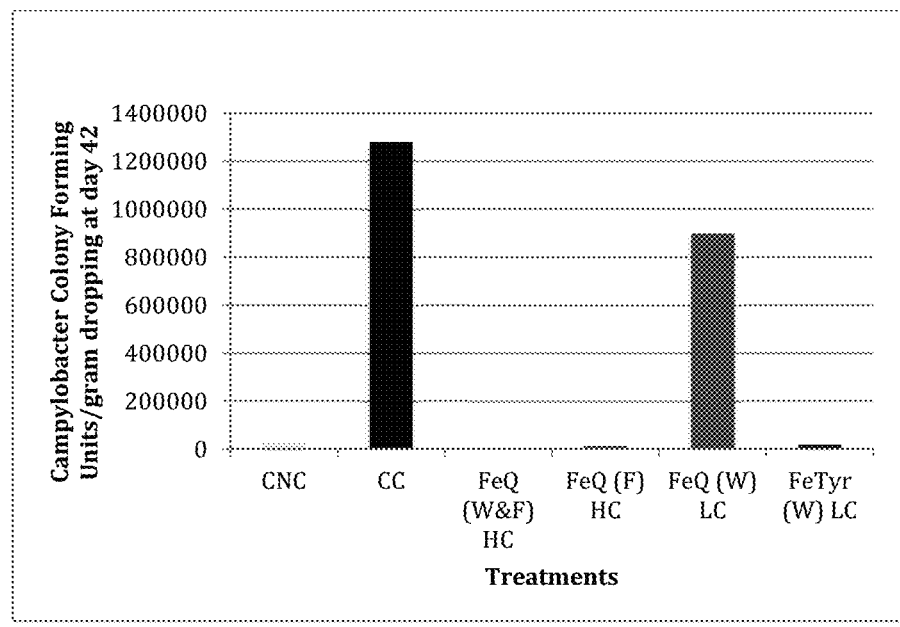
FIG. 3 is a bar graph of the number of *Campylobacter* colony forming units per gram (cfu/g) of bird droppings at day 42 for treatment groups 1-3 and 6-8 of Example 1.

FIG. 3 shows the number of Campylobacter colony forming units per gram (cfu/g) of bird droppings at day 42 for treatment groups 1-3 and 6-8. (A lower number is a better result.) The results show that treatment groups 3 and 6-8 all performed better than the positive control (treatment group 2) demonstrating that FeQ and FeTyr had a positive effect on reducing Campylobacter infection of poultry. Notably, chicken treated with FeTyr, FeQ in feed, and FeQ in feed and water all had colony forming units of Campylobacter per gram of dropping that were similar to, or less than, those of the negative control group (treatment group 1). The detection of low levels of Campylobacter in the negative controls demonstrates how highly contagious the bacterium is, and is likely to be an indication that a small number of birds in the negative control group became infected despite not being experimentally challenged with dirty litter. The results in FIG. 3 for the low concentration of FeQ in water (0.022 g/L; treatment group 7) appears to show less of an effect than the other treatment groups, although this difference was considered more likely due to experimental error for example following cross contamination of samples.

Figure 4:
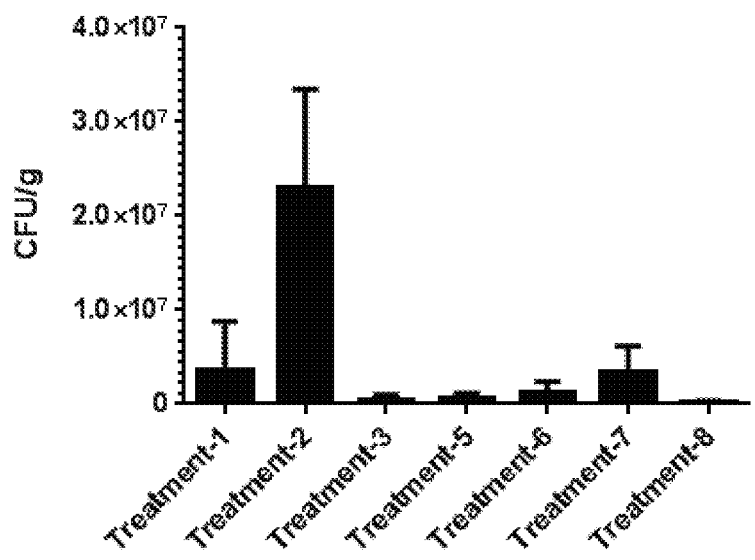
FIG. 4 is a bar graph of the average number of *Campylobacter* colony forming units per gram (cfu/g) of caeca samples at day 42 for treatment groups 1-3 and 5-8 of Example 1.

The results in FIG. 4 confirm that treatment group 7 also had a highly beneficial effect. FIG. 4 shows the average number of Campylobacter colony forming units per gram (cfu/g) of caeca samples at day 42 for treatment groups 1-3 and 5-8. The results show that all the treatment groups (3 and 5-8) all performed better than the positive control (treatment group 2) demonstrating that FeQ and FeTyr had a positive effect on reducing *Campylobacter* infection of poultry.

The effect of the treatments on overall livability and European production and efficiency factor (EPEF) is shown in Table 12. (EPEF=[(Liveability×Live weight in kg at end of trial/Age in Days×FCR commercial)×100].

The effect of FeQ treatment on growth performance in the absence of *Campylobacter* challenge during the starter phase (0-11 days) and period from 0-20 days is shown in Table 13. Since the negative and positive controls (treatment groups 1 and 2) are identical prior to challenge with the dirty litter at day 20, these groups may be pooled for comparison to treatment groups 3, 5, 6, and 7 in order to see if FeQ had an effect on growth in the absence of a challenge by dirty litter contaminated with *Campylobacter* during the first 20 days of growth. The results demonstrate that FeQ promotes growth of chicken even in the absence of a challenge from dirty litter contaminated with *Campylobacter*. At day 20, the average body weight (ABW) for the control groups (treatment groups 1 and 2) is 0.927 kg versus 0.963 kg for treatment groups 3, 5, 6 and 7 which all received FeQ. This improvement in body weight is also reflected in a significantly better MFCR for the FeQ treated birds. Table 13 shows the MFCR for the birds treated in groups 3, 5, 6 and 7 is 1.2996 versus 1.3374 for the control groups (treatment groups 1 and 2). Notably the P-value is less than 0.05.

The same positive effect of FeTyr treatment on growth performance in the absence of *Campylobacter* challenge is also evident from Table 10. The AWG during the first 20 days of production for chicken treated with FeTyr (treatment group 8) is 0.895 kg compared to 0.884 and 0.889 kg for treatment groups 1 and 2 (negative and positive controls). Furthermore, the MFCR during the first 20 days of production for chicken treated with FeTyr (treatment group 8) is 1.311 versus 1.32 and 1.355 for treatment groups 1 and 2, respectively. (A lower MFCR value is an improvement.)

The results of this study demonstrate that both FeQ and FeTyr promote growth and decrease the mortality adjusted feed conversion ratio (MFCR) in the absence or presence of dirty litter contaminated with *Campylobacter*.

TABLE 4

Effect of treatments on growth performance during starter phase (day 0-11)

| Treatment | ABW Day 0 | ABW Day 11 | AFD Day 0-11 | AWG Day 0-11 | MFCR Day 0-11 |
|---|---|---|---|---|---|
| 1 | 0.040 | 0.331 | 0.348 | 0.291 | 1.239$^b$ |
| 2 | 0.040 | 0.337 | 0.359 | 0.297 | 1.228$^b$ |
| 3 | 0.040 | 0.346 | 0.356 | 0.306 | 1.181$^{ab}$ |
| 5 | 0.040 | 0.334 | 0.352 | 0.294 | 1.210$^{ab}$ |
| 6 | 0.041 | 0.351 | 0.360 | 0.310 | 1.168$^a$ |
| 7 | 0.040 | 0.325 | 0.348 | 0.285 | 1.236$^b$ |
| 8 | 0.040 | 0.329 | 0.353 | 0.289 | 1.229$^b$ |
| P-value | 0.136 | 0.418 | 0.979 | 0.463 | 0.005 |
| SED | 0.000 | 0.013 | 0.016 | 0.013 | 0.018 |
| P-value for contrast | | | | | |
| 1 vs 2 | 0.512 | 0.667 | 0.519 | 0.682 | 0.584 |
| 1 vs 2 to 8 | 0.666 | 0.573 | 0.603 | 0.583 | 0.045 |
| 2 vs 3567 | 0.632 | 0.844 | 0.723 | 0.834 | 0.054 |
| 5 vs 6 | 0.099 | 0.213 | 0.627 | 0.233 | 0.033 |
| 5 vs 7 | 0.141 | 0.466 | 0.804 | 0.494 | 0.170 |
| 2 vs 8 | 0.645 | 0.538 | 0.709 | 0.549 | 0.982 |

$^{ab}$within a column reflects differences between treatments when P < 0.05; SED = Standard errors of difference of means; ABW = average body weight (kg); AFD = average feed intake (kg); AWG = average weight gain (kg); MFCR = Mortality adjusted feed conversion ratio; FCR = Feed conversion ratio -commercial.

TABLE 5

Effect of treatments on growth performance during grower phase (day 11-20)

| Treatment | ABW Day 20 | AFD Day 11-20 | AWG Day 11-20 | MFCR Day 11-20 |
|---|---|---|---|---|
| 1 | 0.924 | 0.799 | 0.593 | 1.362 |
| 2 | 0.929 | 0.838 | 0.592 | 1.421 |
| 3 | 0.972 | 0.857 | 0.625 | 1.375 |
| 5 | 0.943 | 0.821 | 0.609 | 1.348 |
| 6 | 0.991 | 0.841 | 0.640 | 1.343 |
| 7 | 0.947 | 0.829 | 0.622 | 1.333 |
| 8 | 0.935 | 0.809 | 0.606 | 1.351 |
| P-value | 0.358 | 0.311 | 0.279 | 0.279 |
| SED | 0.032 | 0.025 | 0.021 | 0.036 |
| P-value for contrast | | | | |
| 1 vs 2 | 0.875 | 0.133 | 0.977 | 0.115 |
| 1 vs 2 to 8 | 0.248 | 0.094 | 0.175 | 0.987 |
| 2 vs 3567 | 0.189 | 0.961 | 0.075 | 0.020 |
| 5 vs 6 | 0.145 | 0.427 | 0.160 | 0.884 |
| 5 vs 7 | 0.913 | 0.737 | 0.546 | 0.673 |
| 2 vs 8 | 0.850 | 0.253 | 0.516 | 0.065 |

SED = Standard errors of difference of means; ABW = average body weight (kg); AFD = average feed intake (kg); AWG = average weight gain (kg); MFCR = Mortality adjusted FCR; FCR = FCR commercial.

TABLE 6

Effect of treatments on growth performance during period day 20-25.

| Treatment | ABW Day 25 | AFD Day 20-25 | AWG Day 20-25 | MFCR Day 20-25 |
|---|---|---|---|---|
| 1 | 1.366 | 0.662 | 0.442 | 1.500 |
| 2 | 1.371 | 0.652 | 0.442 | 1.550 |
| 3 | 1.424 | 0.667 | 0.453 | 1.477 |
| 5 | 1.384 | 0.658 | 0.441 | 1.495 |
| 6 | 1.426 | 0.685 | 0.434 | 1.599 |
| 7 | 1.388 | 0.661 | 0.441 | 1.513 |
| 8 | 1.377 | 0.662 | 0.442 | 1.499 |
| P-value | 0.723 | 0.916 | 0.999 | 0.882 |
| SED | 0.044 | 0.026 | 0.030 | 0.096 |
| P-value for contrast | | | | |
| 1 vs 2 | 0.912 | 0.685 | 0.998 | 0.604 |
| 1 vs 2 to 8 | 0.403 | 0.932 | 0.996 | 0.759 |
| 2 vs 3567 | 0.339 | 0.444 | 0.990 | 0.707 |
| 5 vs 6 | 0.361 | 0.311 | 0.826 | 0.294 |
| 5 vs 7 | 0.930 | 0.902 | 0.988 | 0.854 |
| 2 vs 8 | 0.892 | 0.693 | 0.999 | 0.604 |

SED = Standard errors of difference of means; ABW = average body weight (kg); AFD = average feed intake (kg); AWG = average weight gain (kg); MFCR = Mortality adjusted FCR; FCR = FCR commercial.

TABLE 7

Effect of treatments on overall growth performance during grower phase (day 11-25)

| Treatment | AFD | AWG Day 11-25 | MFCR |
|---|---|---|---|
| 1 | 1.462 | 1.035 | 1.421 |
| 2 | 1.490 | 1.034 | 1.457 |
| 3 | 1.524 | 1.078 | 1.417 |
| 5 | 1.479 | 1.050 | 1.409 |
| 6 | 1.526 | 1.075 | 1.440 |
| 7 | 1.490 | 1.064 | 1.406 |
| 8 | 1.471 | 1.048 | 1.414 |
| P-value | 0.660 | 0.804 | 0.598 |
| SED | 0.042 | 0.036 | 0.030 |
| P-value for contrast | | | |
| 1 vs 2 | 0.516 | 0.984 | 0.241 |
| 1 vs 2 to 8 | 0.293 | 0.406 | 0.891 |
| 2 vs 3567 | 0.657 | 0.267 | 0.118 |
| 5 vs 6 | 0.280 | 0.498 | 0.300 |
| 5 vs 7 | 0.787 | 0.707 | 0.925 |
| 2 vs 8 | 0.664 | 0.695 | 0.165 |

SED = Standard errors of difference of means; ABW = average body weight (kg); AFD = average feed intake (kg); AWG = average weight gain (kg); MFCR = Mortality adjusted FCR.

TABLE 8

Effect of treatments on overall growth performance during finisher phase (day 25-42)

| Treatment | ABW Day 42 | AFD | AWG Day 25-42 | MFCR |
|---|---|---|---|---|
| 1 | 3.437 | 3.479 | 2.070$^b$ | 1.688 |
| 2 | 3.186 | 3.480 | 1.814$^a$ | 1.889 |
| 3 | 3.342 | 3.387 | 1.918$^{ab}$ | 1.773 |
| 5 | 3.407 | 3.357 | 2.023$^b$ | 1.706 |
| 6 | 3.464 | 3.315 | 2.039$^b$ | 1.704 |
| 7 | 3.304 | 3.362 | 1.916$^{ab}$ | 1.793 |
| 8 | 3.341 | 3.434 | 1.964$^{ab}$ | 1.716 |
| P-value | 0.027 | 0.56 | 0.009 | 0.211 |
| SED | 0.075 | 0.099 | 0.062 | 0.081 |
| P-value for contrast | | | | |
| 1 vs 2 | 0.004 | 0.997 | <.001 | 0.022 |
| 1 vs 2 to 8 | 0.110 | 0.247 | 0.016 | 0.233 |
| 2 vs 3567 | 0.004 | 0.129 | 0.004 | 0.035 |
| 5 vs 6 | 0.455 | 0.680 | 0.800 | 0.988 |
| 5 vs 7 | 0.187 | 0.960 | 0.101 | 0.294 |
| 2 vs 8 | 0.053 | 0.649 | 0.027 | 0.046 |

$^{ab}$within a column reflects differences between treatments when $P < 0.05$; SED = Standard errors of difference of means; ABW = average body weight (kg); AFD = average feed intake (kg); AWG = average weight gain (kg); MFCR = Mortality adjusted FCR; FCR = FCR commercial.

TABLE 9

Effect of treatments on the growth performance during the experimental period of day 20-42 (after the birds were challenged)

| Treatment | AFD | AWG Day 20-42 | MFCR |
|---|---|---|---|
| 1 | 4.142 | 2.512$^b$ | 1.653 |
| 2 | 4.131 | 2.256$^a$ | 1.820 |
| 3 | 4.054 | 2.370$^{ab}$ | 1.713 |
| 5 | 4.015 | 2.464$^{ab}$ | 1.665 |
| 6 | 4.001 | 2.473$^{ab}$ | 1.678 |
| 7 | 4.023 | 2.357$^{ab}$ | 1.739 |
| 8 | 4.096 | 2.406$^{ab}$ | 1.676 |
| P-value | 0.767 | 0.025 | 0.344 |
| SED | 0.110 | 0.068 | 0.075 |
| P-value for contrast | | | |
| 1 vs 2 | 0.926 | 0.001 | 0.038 |
| 1 vs 2 to 8 | 0.306 | 0.028 | 0.290 |
| 2 vs 3567 | 0.229 | 0.008 | 0.055 |
| 5 vs 6 | 0.898 | 0.894 | 0.856 |
| 5 vs 7 | 0.941 | 0.138 | 0.331 |
| 2 vs 8 | 0.752 | 0.042 | 0.070 |

$^{ab}$within a column reflects differences between treatments when $P < 0.05$; SED = Standard errors of difference of means; ABW = average body weight (kg); AFD = average feed intake (kg); AWG = average weight gain (kg); MFCR = Mortality adjusted.

TABLE 10

Overall effect of treatments on growth performance during the experimental period of day 0-20 (before birds were challenged).

| Treatment | AFD | AWG Day 0-20 | MFCR |
|---|---|---|---|
| 1 | 1.147 | 0.884 | 1.320 |
| 2 | 1.196 | 0.889 | 1.355 |
| 3 | 1.213 | 0.931 | 1.310 |
| 5 | 1.173 | 0.903 | 1.303 |
| 6 | 1.201 | 0.951 | 1.284 |
| 7 | 1.178 | 0.907 | 1.302 |
| 8 | 1.161 | 0.895 | 1.311 |
| P-value | 0.623 | 0.368 | 0.225 |
| SED | 0.038 | 0.032 | 0.025 |
| P-value for contrast | | | |
| 1 vs 2 | 0.215 | 0.881 | 0.181 |
| 1 vs 2 to 8 | 0.191 | 0.251 | 0.627 |
| 2 vs 3567 | 0.860 | 0.188 | 0.012 |
| 5 vs 6 | 0.476 | 0.150 | 0.469 |
| 5 vs 7 | 0.907 | 0.899 | 0.978 |
| 2 vs 8 | 0.371 | 0.846 | 0.094 |

SED = Standard errors of difference of means; ABW = average body weight (kg); AFD = average feed intake (kg); AWG = average weight gain (kg); MFCR = Mortality adjusted.

TABLE 11

Overall effect of treatment groups on growth performance (day 0-42)

| Treatment | AFD | AWG Day 0-42 | MFCR |
|---|---|---|---|
| 1 | 5.289 | 3.397$^b$ | 1.563 |
| 2 | 5.328 | 3.145$^a$ | 1.679 |
| 3 | 5.267 | 3.302$^{ab}$ | 1.595 |
| 5 | 5.188 | 3.367$^{ab}$ | 1.560 |
| 6 | 5.201 | 3.423$^b$ | 1.563 |
| 7 | 5.201 | 3.265$^{ab}$ | 1.612 |
| 8 | 5.258 | 3.301$^{ab}$ | 1.577 |
| P-value | 0.920 | 0.028 | 0.193 |
| SED | 0.132 | 0.075 | 0.047 |
| P-value for contrast | | | |
| 1 vs 2 | 0.773 | 0.004 | 0.024 |
| 1 vs 2 to 8 | 0.633 | 0.111 | 0.352 |
| 2 vs 3567 | 0.29 | 0.004 | 0.018 |
| 5 vs 6 | 0.920 | 0.461 | 0.954 |
| 5 vs 7 | 0.924 | 0.190 | 0.284 |
| 2 vs 8 | 0.601 | 0.053 | 0.043 |

$^{ab}$within a column reflects differences between treatments when $P < 0.05$; SED = Standard errors of difference of means; ABW = average body weight (kg); AFD = average feed intake (kg); AWG = average weight gain (kg); MFCR = Mortality adjusted.

TABLE 12

The effect of treatments on overall liveability and
European production and efficiency factor (EPEF)

| | EPEF | |
|---|---|---|
| Treatment | Day 20 | Day 42 |
| 1 | 318.3 | 282.8 |
| 2 | 334.7 | 250.7 |
| 3 | 350.4 | 262.9 |
| 5 | 352.0 | 278.3 |
| 6 | 364.8 | 265.0 |
| 7 | 354.5 | 276.2 |
| 8 | 336.4 | 296.0 |
| P-value | 0.547 | 0.842 |
| SED | 23.83 | 31.68 |
| P-value for contrast | | |
| 1 vs 2 | 0.500 | 0.323 |
| 1 vs 2 to 8 | 0.111 | 0.645 |
| 2 vs 3567 | 0.285 | 0.437 |
| 5 vs 6 | 0.599 | 0.680 |
| 5 vs 7 | 0.919 | 0.949 |
| 2 vs 8 | 0.945 | 0.170 |

TABLE 13

Effect of treatments on growth performance in
absence of *Campylobacter* challenge during
starter phase (0-11 days) and period 0-20 days.

| Treatment | ABW Day 11 | ABW Day 20 | AFD 0-20 days | AWG 0-20 days | MFCR 0-20 |
|---|---|---|---|---|---|
| Groups 1 & 2 | 0.334 | 0.927 | 1.172 | 0.887 | 1.3374 |
| FeQ (Groups 3, 5, 6, 7) | 0.339 | 0.963 | 1.191 | 0.923 | 1.2996 |
| P-value | 0.584 | 0.079 | 0.432 | 0.078 | 0.029 |
| SED | 0.009 | 0.020 | 0.024 | 0.020 | 0.016 |

ABW = average body weight (kg);
AFD = average feed intake (kg);
AWG = average weight gain (kg);
MFCR = mortality adjusted feed conversion ratio

Example 2. Fe-Lac Prevention of Biofilm Formation by *Pseudomonas aeruginosa*

Materials and Methods

*Pseudomonas aeruginosa* PAO-1 strain was routinely grown on either LB (Luria-Bertani, Oxoid, UK) agar plates at 37° C. or in broth at 37° C. with 200 rpm shaking. UV-sterilized glass slides were incubated in either 15 mL RPMI-1640 defined medium (Sigma, UK) or 15 mL RPMI-1640 with Fe-Lac inoculated with diluted ($OD_{600}$=0.01) bacteria from overnight cultures at 37° C. with 60 rpm shaking for 72 hours. The slides were removed from bacterial culture and washed with 15 mL phosphate buffered saline at room temperature for 5 minutes three times and then rinsed with distilled $H_2O$. After washing, the slides were stained with 20 μM SYTO17 dye (Invitrogen, UK) at room temperature for 30 minutes. After removing excess staining dye and air-drying, the samples were examined using a Carl Zeiss LSM 700 Laser Scanning Microscope with ZEN 2009 imaging software (Carl Zeiss, Germany). The coverage rate of bacteria on the surface was analysed using open source Image J 1.44 software (National Institute of Health, US).

Results

Figure 5:
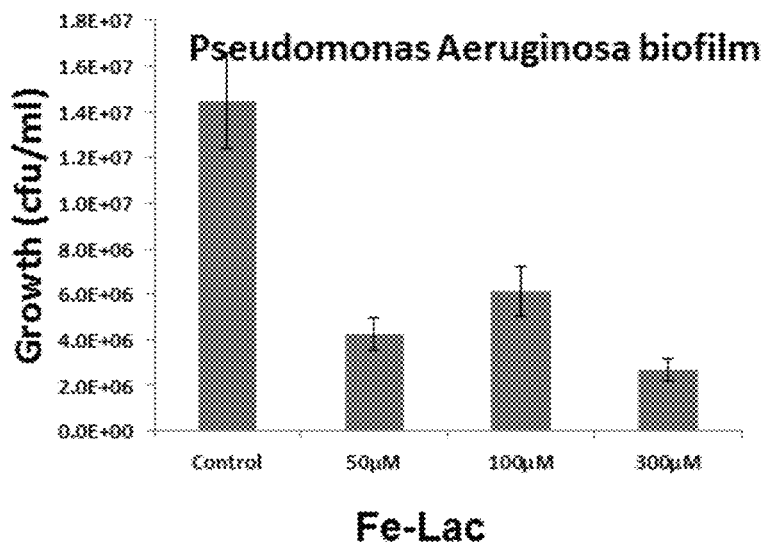
FIG. 5 is a bar graph showing the biofilm coverage rate of PAO1 *Pseudomonas aeruginosa* on the surface of a glass slide, comparing PAO1 *Pseudomonas* with no Fe-Lac and PAO1 *Pseudomonas*+50, 100, and 300 µM Fe-Lac treatment, described in Example 2.

FIG. 5A shows the titration effect on biofilm formation wherein Fe-Lac at 50, 100, and 300 μM inhibits the formation of biofilm by *Pseudomonas aeruginosa*. In the absence of Fe-Lac (control), a higher coverage rate was measured for *Pseudomonas aeruginosa* than in the presence of Fe-Lac.

FIG. 5B shows the dispersion effect on biofilm formation wherein Fe-Lac at 10, 50, and 100 μM inhibits the formation of biofilm by *Pseudomonas aeruginosa*. In the absence of Fe-Lac (control), a higher coverage rate was measured for *Pseudomonas aeruginosa* than in the presence of Fe-Lac.

Example 3. Fe-Cit Prevention of Biofilm Formation by *Pseudomonas aeruginosa*

Materials and Methods

*Pseudomonas aeruginosa* PAO-1 strain was routinely grown on either LB (Luria-Bertani, Oxoid, UK) agar plates at 37° C. or in broth at 37° C. with 200 rpm shaking. UV-sterilized glass slides were incubated in either 15 mL RPMI-1640 defined medium (Sigma, UK) or 15 mL RPMI-1640 with Fe-Cit inoculated with diluted ($OD_{600}$=0.01) bacteria from overnight cultures at 37° C. with 60 rpm shaking for 72 hours. The slides were removed from bacterial culture and washed with 15 mL phosphate buffered saline at room temperature for 5 minutes three times and then rinsed with distilled $H_2O$. After washing, the slides were stained with 20 μM SYTO17 dye (Invitrogen, UK) at room temperature for 30 minutes. After removing excess staining dye and air-drying, the samples were examined using a Carl Zeiss LSM 700 Laser Scanning Microscope with ZEN 2009 imaging software (Carl Zeiss, Germany). The coverage rate of bacteria on the surface was analysed using open source Image J 1.44 software (National Institute of Health, US).

Results

Figure 6:
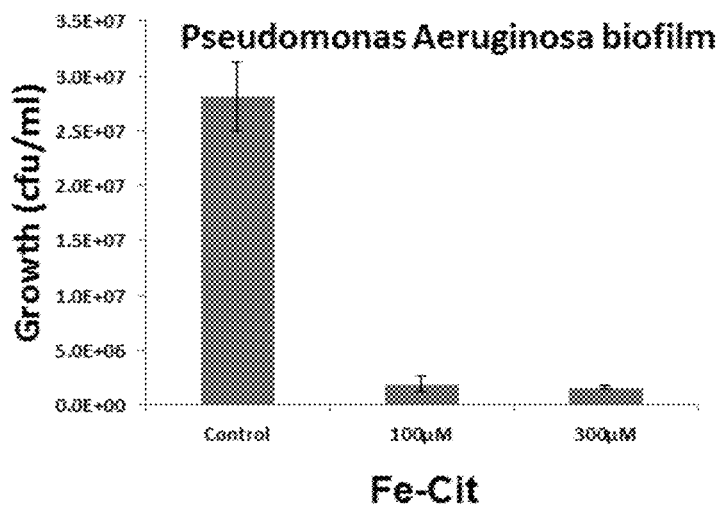
FIG. 6 is a bar graph showing the biofilm coverage rate of PAO1 *Pseudomonas aeruginosa* on the surface of a glass slide, comparing PAO1 *Pseudomonas* with no Fe-Cit and PAO1 *Pseudomonas*+100 and 300 µM Fe-Lac treatment, described in Example 3.

FIG. 6 shows the effect on biofilm formation wherein Fe-Cit at 100 and 300 μM inhibits the formation of biofilm by *Pseudomonas aeruginosa*. In the absence of Fe-Cit (control), a higher coverage rate was measured for *Pseudomonas aeruginosa* than in the presence of Fe-Cit.

Example 4. Fe-Tart Prevention of Biofilm Formation by *Pseudomonas aeruginosa*

Materials and Methods

*Pseudomonas aeruginosa* PAO-1 strain was routinely grown on either LB (Luria-Bertani, Oxoid, UK) agar plates at 37° C. or in broth at 37° C. with 200 rpm shaking. UV-sterilized glass slides were incubated in either 15 mL RPMI-1640 defined medium (Sigma, UK) or 15 mL RPMI-1640 with Fe-Tart inoculated with diluted ($OD_{600}$=0.01) bacteria from overnight cultures at 37° C. with 60 rpm shaking for 72 hours. The slides were removed from bacterial culture and washed with 15 mL phosphate buffered saline at room temperature for 5 minutes three times and then rinsed with distilled $H_2O$. After washing, the slides were stained with 20 μM SYTO17 dye (Invitrogen, UK) at room temperature for 30 minutes. After removing excess staining dye and air-drying, the samples were examined using a Carl Zeiss LSM 700 Laser Scanning Microscope with ZEN 2009 imaging software (Carl Zeiss, Germany). The coverage rate of bacteria on the surface was analysed using open source Image J 1.44 software (National Institute of Health, US).

Results

Figure 7:
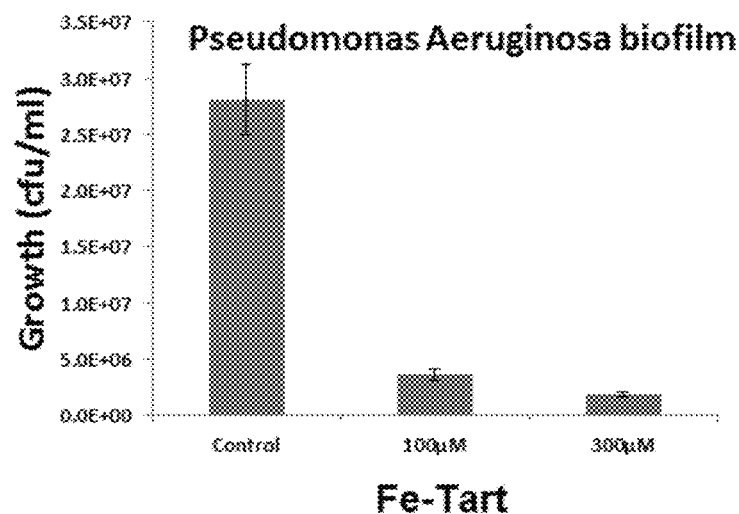
FIG. 7 is a bar graph showing the biofilm coverage rate of PAO1 *Pseudomonas aeruginosa* on the surface of a glass slide, comparing PAO1 *Pseudomonas* with no Fe-Tart and PAO1 *Pseudomonas*+100 and 300 µM Fe-Tart treatment, described in Example 4.

FIG. 7 shows the effect on biofilm formation wherein Fe-Tart at 100 and 300 μM inhibits the formation of biofilm by *Pseudomonas aeruginosa*. In the absence of Fe-Tart (control), a higher coverage rate was measured for *Pseudomonas aeruginosa* than in the presence of Fe-Tart.

Example 5. Fe-Gly Prevention of Biofilm Formation by *Pseudomonas aeruginosa*

Materials and Methods

*Pseudomonas aeruginosa* PAO-1 strain was routinely grown on either LB (Luria-Bertani, Oxoid, UK) agar plates at 37° C. or in broth at 37° C. with 200 rpm shaking. UV-sterilized glass slides were incubated in either 15 mL RPMI-1640 defined medium (Sigma, UK) or 15 mL RPMI-1640 with Fe-Gly inoculated with diluted ($OD_{600}$=0.01) bacteria from overnight cultures at 37° C. with 60 rpm shaking for 72 hours. The slides were removed from bacterial culture and washed with 15 mL phosphate buffered saline at room temperature for 5 minutes three times and then rinsed with distilled $H_2O$. After washing, the slides were stained with 20 μM SYTO17 dye (Invitrogen, UK) at room temperature for 30 minutes. After removing excess staining dye and air-drying, the samples were examined using a Carl Zeiss LSM 700 Laser Scanning Microscope with ZEN 2009 imaging software (Carl Zeiss, Germany). The coverage rate of bacteria on the surface was analysed using open source Image J 1.44 software (National Institute of Health, US).

Results

Figure 8:
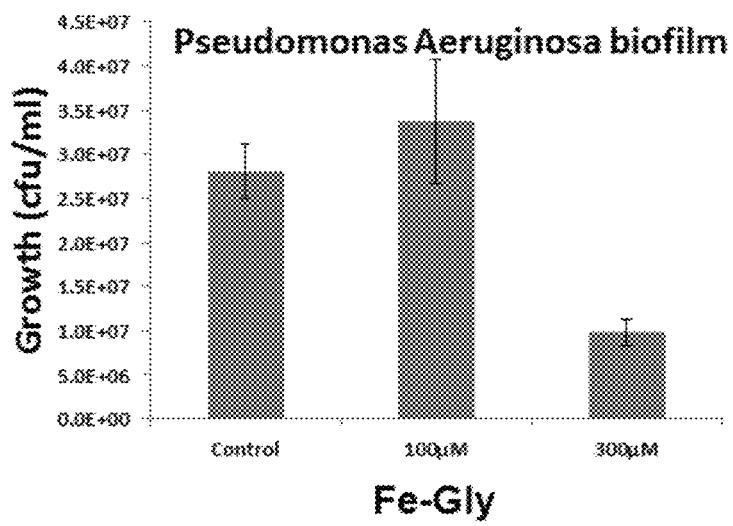
FIG. 8 is a bar graph showing the biofilm coverage rate of PAO1 *Pseudomonas aeruginosa* on the surface of a glass slide, comparing PAO1 *Pseudomonas* with no Fe-Gly and PAO1 *Pseudomonas*+100 and 300 µM Fe-Gly treatment, described in Example 5.

FIG. 8 shows the effect on biofilm formation wherein Fe-Gly at 100 and 300 μM inhibits the formation of biofilm by *Pseudomonas aeruginosa*. At 300 μM Fe-Gly was able to inhibit biofilm formation as compared to the absence of Fe-Gly (control) where a higher coverage rate was measured for *Pseudomonas aeruginosa* than in the presence of Fe-Gly.

Example 6. Inhibition of Biofilm Formation on Beads Surface by *Campylobacter jejuni* NCTC 11168 Using Fe-Tart, FeQ (QPLEX), and Fe-Cit Materials and Methods The effect of Fe-Tart, Fe-Cit and Fe-Q (QPLEX) on biofilm formation by *Campylobacter jejuni* NCTC 1168 was tested as described in the materials and methods of Example 1 of PCT/US2015/044603 and examples above.

Results

Figure 9:
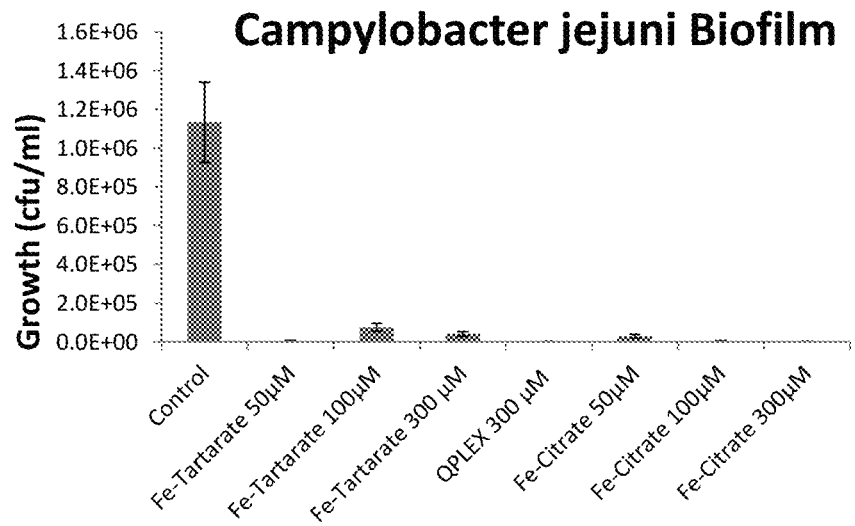
FIG. 9 is a bar graph showing the biofilm coverage rate of *Campylobacter jejuni* NCTC11168 strain on the surface of beads, comparing the effect of Fe-Tart at 50 µM, 100 µM, and 300 µM, the effect of FeQ (QPLEX) at 300, and the effect of Fe-Cit at 50 µM, 100 µM, as described in Example 6. A control sample shows the biofilm formation in the absence of any additives.

The effect of Fe-Tart, FeQ (QPLEX), and Fe-Cit on biofilm formation on a bead surface by *Campylobacter jejuni* NCTC 11168 tested as described in the materials and methods. The data in FIG. 9 shows that Fe-Tart, FeQ (QPLEX), and Fe-Cit inhibited *C. jejuni* biofilm formation on plastic coated UV beads. Fe-Tart at 50, 100, and 300 μM, as well as Fe-Cit at 50, 100, and 300 μM inhibit the formation of biofilm by *C. jejuni*. A control (without addition of Fe-Tart, FeQ (QPLEX), or Fe-Cit) demonstrated a significantly higher coverage rate of *C. jejuni* biofilm on the bead surface.

Example 7: Enhancement of Weight Gain in Weanling Pigs by Administration of Water Soluble Fe-Complexes The objective of this pilot study is to evaluate the effect of three water soluble Fe-complexes (ferric lactate, ferric citrate and ferric tartrate) on growth performance and colonic microbiota of weaner pigs.

Materials and Methods

Animal Details

Number of treatments: 4 treatments
Number of replicates: 4 pens
Number of animals per pen: 4 pigs (balanced for sex as much as possible)
Number of pens in study: 16 pens
Animal species and breed: newly weaned pigs (Large White×Landrace)
Total number of animals: 64

Experimental Design

There were four (4) treatments, each having 4 replicate pens with 4 pigs per replicate pen, i.e. 16 pigs per treatment or 64 pigs in total. Treatment 1 were control diets, whilst Treatment 2 to 4 were through providing water that includes different Fe-complexes (Table 14).

TABLE 14

Experimental treatments and treatment structure

| Treatment | Additive | Fe-tartrate (g/L) | Fe-citrate (g/L) | Fe-lactate (g/L) | Pens per trt |
|---|---|---|---|---|---|
| 1 | No | — | — | — | 4 |
| 2 | Yes | 0.2 | | | 4 |
| 3 | Yes | | 0.2 | | 4 |
| 2 | Yes | | | 0.2 | 4 |

Feeds

The feeds used were standard commercial, non-medicated feeds, tailored for weaner pigs. The feeds were offered as a 3 mm pellet and ad libitum. Water will also be available ad libitum.

Housing

The Ethology 3 building of SRUC's Easter Howgate Pig Unit were used in this study. This house consists of 6 rooms, each with 4 pens, so holds up to 24 pens of 4 $m^2$ each; for this study, 4 rooms were used. The animal house, which is an environmentally controlled building, were sanitized prior to use and between rounds. Pigs were placed at weaning on a thick layer of fresh white wood shavings or straw in pens. Pens were balanced as much as possible for litter origin and sex (2 intact males and 2 females). Pens were bedded with additional sawdust or straw as required, and were equipped with a single feeder and nipple drinker. Foods were available ad libitum throughout. Water were supplied via measured bottles per pen, and also available. Environmental temperature were maintained at 26° C. for the first 4 days after weaning and then decreased by 2° C. for the remainder of the experiment. Lights were on from 08:00 am till 18:00 pm and night-lights maintained between 18:00 pm and 08:00 am.

Parameters Measured

The diet was analyzed for proximate analysis (dry matter, protein, fat and fibre [Neutral Detergent Fibre]). See Table 16.

Pigs were individually weighed at day 0, 6 and 13. Pigs removed or found dead weighed, and date noted.

The volume of feed offered per pen was recorded daily from day 0 until day 12, inclusive. Feed refusals were recorded daily from day 1 until day 13, inclusive.

Pig weights, feed offered and feed refusals were used to determine averaged daily weight gain, daily feed intake and feed conversion ratio, over day 0 to 6,6 to 13, as well as 0 to 13.

From day 0 until day 13, the volume of water offered per pen was recorded daily and water levels were recorded from the water bottles prior to morning feeding before tupping up.

Faeces, cleanliness and health scores was taken daily (Appendix). Faecal scores especially are indicative of diarrhea incidence, and are used in the industry as a general easy to observe gut health indicator. Faecal samples were taken from a randomly selected male pig at days 0 (weaning), 4, 6, and 13. Faecal samples were stored under conditions allowing submission to SAC Veterinary Services for quantification of lactobacilli and coliforms, and their ratio (L:C ratio). These are used as key indicators for gut health, with a greater L:C ratio being indicative to better gut health.

The same male pig used for sampling was subjected to post mortem on day 13, with an emphasis on assessment of gut lesion types and scores. Daily health, cull and mortality records were kept. Cause of death and culls were recorded and any inexplicable deaths or unexpected deaths or pigs in ill-health were subjected to post-mortem by SAC Veterinary Services. Mortality corrected feed conversion ratio was calculated if mortality occurs.

TABLE 15

Summarized sampling and analysis

| Sample | Nr | Analysis | Lab | Notes |
|---|---|---|---|---|
| Feed | 1 | Dry matter, crude protein, fat, fibre (NDF). | DM Scientific | One feed sample only |
| Faeces | 64 | *Lactobacilli* and coliforms | SAC Veterinary Services | Data were in cfu/g, and their ratio (L:C ratio) is calculated |
| Postmortem | 16 | Gross PM, with emphasis on gut lesions | SAC Veterinary Services | Same pig as used for faecal sampling |

Data gathered were analyzed using analysis of variance (ANOVA), to test for the effect of Fe-complex provision per se and Fe-complex type. Treatments were allocated in blocks within Ethology 3, as each of the four proposed treatments were in each of the four rooms used. As such, rooms were used as block in the model. Effects were considered significant at $P<0.05$.

APPENDIX. HEALTH, FAECES AND CLEANLINESS SCORES

| Type | Score | Description |
|---|---|---|
| Health | 1 | Pigs lying, sitting, standing or walking and actively responds to human presence; skin pink, bright eyes, upright ears |
|  | 2 | Pigs lying/sleeping, responding normally to human presence upon gentle stimulation; skin pink, bright eyes, upright ears |
|  | 3 | Pigs lying and slightly shivering, not responding normally following gentle stimulation, skin pink-greyish, eyes somewhat sunken, ears slightly dropping |
|  | 4 | Pigs showing pain, e.g. abdomen kicking, lying twisted, hunched back, skin grey, sunken eyes, ears dropping |
| Faeces | 1 | Firm stool shape (1.5 for soft faeces but compact, clay-type) |
|  | 2 | No formed stool, little spreading ('normal diarrhea') |
|  | 3 | No formed stool, watery, readily spreading ('watery diarrhea') |
|  | 4 | No formed stool, very watery, flecks of blood, rapidly spreading ('dysentery') |
| Cleanliness | 1 | All pigs are clean |
|  | 2 | 1 or 2 pigs are little dirty |
|  | 3 | 3 or 4 pigs are little dirty |
|  | 4 | All pigs are very dirty |

Actions:
If health score=1 or 2, then no further action required.
If health or faeces score=3 raise awareness with NACWO
If health score=4, or faeces score=4, then seek veterinary advice.

Results
The results are shown in the following tables.

TABLE 16

Body weights (kg/pig)

| Treatments[1] | Days post weaning | | | |
|---|---|---|---|---|
|  | 0 | 4 | 7 | 14 |
| Water | 9.77 | 10.88 | 11.92 | 15.61 |
| Ferric Lactate | 9.74 | 10.35 | 10.94 | 15.05 |
| Ferric Tartrate | 9.81 | 10.81 | 11.46 | 15.27 |
| Ferric Citrate | 9.78 | 10.80 | 11.60 | 15.91 |
| s.e.d. | 0.11 | 0.29 | 0.20 | 0.38 |
| P-values |  |  |  |  |
| Treatment | 0.929 | 0.297 | 0.006 | 0.185 |
| Contrasts |  |  |  |  |
| Water vs all | 0.955 | 0.353 | 0.006 | 0.543 |
| Water vs Fe-lactate | 0.773 | 0.097 | <.001 | 0.175 |
| Water vs Fe-tartrate | 0.725 | 0.798 | 0.046 | 0.400 |
| Water vs Fe-citrate | 0.940 | 0.785 | 0.141 | 0.441 |

[1]four pens per treatment; four pigs per pen (two males and two females)

TABLE 17

Averaged daily feed intake (g/day/pig)

| Treatments[1] | Days post weaning | | | | |
|---|---|---|---|---|---|
|  | 0 to 4 | 4 to 7 | 0 to 7 | 7 to 14 | 0 to 14 |
| Water | 220 | 445 | 316 | 555 | 436 |
| Ferric Lactate | 154 | 315 | 223 | 532 | 378 |
| Ferric Tartrate | 190 | 410 | 284 | 516 | 400 |
| Ferric Citrate | 202 | 428 | 299 | 590 | 445 |
| s.e.d. | 40 | 46 | 37 | 33 | 26 |
| P-values |  |  |  |  |  |
| Treatment | 0.455 | 0.075 | 0.134 | 0.204 | 0.100 |
| Contrasts |  |  |  |  |  |
| Water vs all | 0.280 | 0.139 | 0.149 | 0.750 | 0.221 |
| Water vs Fe-lactate | 0.137 | 0.019 | 0.033 | 0.510 | 0.055 |
| Water vs Fe-tartrate | 0.476 | 0.465 | 0.408 | 0.270 | 0.209 |
| Water vs Fe-citrate | 0.671 | 0.718 | 0.649 | 0.318 | 0.744 |

[1]four pens per treatment; four pigs per pen (two males and two females)

TABLE 18

Averaged body weight gain (g/day/pig)

| Treatments[1] | Days post weaning | | | | |
|---|---|---|---|---|---|
|  | 0 to 4 | 4 to 7 | 0 to 7 | 7 to 14 | 0 to 14 |
| Water | 278 | 345 | 307 | 527 | 417 |
| Ferric Lactate | 153 | 197 | 172 | 587 | 380 |
| Ferric Tartrate | 249 | 217 | 235 | 545 | 390 |
| Ferric Citrate | 256 | 265 | 260 | 617 | 438 |
| s.e.d. | 78 | 91 | 30 | 45 | 27 |
| P-values |  |  |  |  |  |
| Treatment | 0.436 | 0.417 | 0.009 | 0.254 | 0.196 |
| Contrasts |  |  |  |  |  |
| Water vs all | 0.380 | 0.144 | 0.007 | 0.164 | 0.531 |
| Water vs Fe-lactate | 0.144 | 0.138 | 0.001 | 0.215 | 0.199 |

TABLE 18-continued

Averaged body weight gain (g/day/pig)

| Treatments[1] | Days post weaning | | | | |
|---|---|---|---|---|---|
| | 0 to 4 | 4 to 7 | 0 to 7 | 7 to 14 | 0 to 14 |
| Water vs Fe-tartrate | 0.717 | 0.193 | 0.039 | 0.699 | 0.346 |
| Water vs Fe-citrate | 0.781 | 0.401 | 0.146 | 0.079 | 0.452 |

[1] four pens per treatment; four pigs per pen (two males and two females)

TABLE 19

Feed conversion ratio (g/g)

| Treatments[1] | Days post weaning | | | | |
|---|---|---|---|---|---|
| | 0 to 4 | 4 to 7 | 0 to 7 | 7 to 14 | 0 to 14 |
| Water | 0.80 | 1.56 | 1.07 | 1.08 | 1.05 |
| Ferric Lactate | 0.54 | −1.65 | 2.67 | 0.91 | 1.00 |
| Ferric Tartrate | 0.79 | 2.98 | 1.23 | 0.95 | 1.03 |
| Ferric Citrate | 0.79 | 1.81 | 1.17 | 0.98 | 1.03 |
| s.e.d. | 0.19 | 2.61 | 1.01 | 0.05 | 0.05 |
| P-values | | | | | |
| Treatment Contrasts | 0.463 | 0.378 | 0.388 | 0.067 | 0.806 |
| Water vs all | 0.542 | 0.815 | 0.469 | 0.017 | 0.500 |
| Water vs Fe-lactate | 0.191 | 0.249 | 0.147 | 0.013 | 0.359 |
| Water vs Fe-tartrate | 0.960 | 0.599 | 0.873 | 0.048 | 0.657 |
| Water vs Fe-citrate | 0.932 | 0.926 | 0.922 | 0.109 | 0.774 |

[1] four pens per treatment; four pigs per pen (two males and two females)

TABLE 20

Daily averaged water intake (g/day/pig)

| Treatments[1] | Days post weaning | | | | |
|---|---|---|---|---|---|
| | 0 to 4 | 4 to 7 | 0 to 7 | 7 to 14 | 0 to 14 |
| Water | 766 | 1120 | 921 | 1368 | 1148 |
| Ferric Lactate | 641 | 885 | 746 | 1335 | 1040 |
| Ferric Tartrate | 711 | 1115 | 884 | 1359 | 1122 |
| Ferric Citrate | 664 | 1146 | 871 | 1451 | 1161 |
| s.e.d. | 102 | 105 | 92 | 97 | 90 |
| P-values | | | | | |
| Treatment Contrasts | 0.639 | 0.109 | 0.312 | 0.669 | 0.562 |
| Water vs all | 0.289 | 0.427 | 0.274 | 0.870 | 0.592 |
| Water vs Fe-lactate | 0.251 | 0.052 | 0.089 | 0.739 | 0.260 |
| Water vs Fe-tartrate | 0.605 | 0.961 | 0.698 | 0.929 | 0.773 |
| Water vs Fe-citrate | 0.345 | 0.809 | 0.598 | 0.418 | 0.894 |

[1] four pens per treatment; four pigs per pen (two males and two females)

TABLE 21

Faecal *E. coli* counts ($^{10}$log cfu/g)

| Treatments[1] | Days post weaning | | | |
|---|---|---|---|---|
| | 0 | 4 | 7 | 14 |
| Water | 8.26 | 7.12 | 6.30 | 5.15 |
| Ferric Lactate | 8.40 | 7.80 | 6.37 | 5.98 |
| Ferric Tartrate | 8.67 | 6.42 | 6.51 | 6.43 |
| Ferric Citrate | 7.08 | 7.30 | 6.17 | 4.73 |
| s.e.d. | 0.40 | 1.34 | 1.20 | 0.55 |
| P-values | | | | |
| Treatment Contrasts | 0.027 | 0.599 | 0.996 | 0.103 |
| Water vs all | 0.542 | 0.946 | 0.946 | 0.143 |
| Water vs Fe-lactate | 0.737 | 0.503 | 0.933 | 0.085 |
| Water vs Fe-tartrate | 0.332 | 0.526 | 0.829 | 0.028 |
| Water vs Fe-citrate | 0.024 | 0.908 | 0.925 | 0.512 |

[1] four pens per treatment; four pigs per pen (two males and two females); one male pig was sampled for this parameter, and the same pig was sampled throughout

TABLE 22

Faecal *lactobacilli* counts ($^{10}$log cfu/g)

| Treatments[1] | Days post weaning | | | |
|---|---|---|---|---|
| | 0 | 4 | 7 | 14 |
| Water | 8.81 | 7.33 | 8.44 | 8.79 |
| Ferric Lactate | 8.68 | 8.76 | 8.97 | 8.77 |
| Ferric Tartrate | 8.84 | 8.94 | 9.48 | 8.79 |
| Ferric Citrate | 9.10 | 8.74 | 8.48 | 8.43 |
| s.e.d. | 0.28 | 0.83 | 0.55 | 0.55 |
| P-values | | | | |
| Treatment Contrasts | 0.531 | 0.256 | 0.275 | 0.906 |
| Water vs all | 0.783 | 0.067 | 0.257 | 0.782 |
| Water vs Fe-lactate | 0.661 | 0.130 | 0.355 | 0.976 |
| Water vs Fe-tartrate | 0.918 | 0.092 | 0.098 | 0.995 |
| Water vs Fe-citrate | 0.330 | 0.155 | 0.944 | 0.552 |

[1] four pens per treatment; four pigs per pen (two males and two females); one male pig was sampled for this parameter, and the same pig was sampled throughout

TABLE 23

*Lactobacilli* to *E. coli* ratio (L:C)

| Treatments[1] | Days post weaning | | | |
|---|---|---|---|---|
| | 0 | 4 | 7 | 14 |
| Water | 1.08 | 1.00 | 1.33 | 1.75 |
| Ferric Lactate | 1.03 | 1.08 | 1.33 | 1.45 |
| Ferric Tartrate | 1.02 | 1.27 | 1.45 | 1.28 |
| Ferric Citrate | 1.27 | 1.57 | 1.65 | 1.91 |
| s.e.d. | 0.05 | 0.41 | 0.27 | 0.31 |
| P-values | | | | |
| Treatment Contrasts | 0.010 | 0.498 | 0.615 | 0.263 |
| Water vs all | 0.477 | 0.223 | 0.332 | 0.261 |
| Water vs Fe-lactate | 0.449 | 0.788 | 0.962 | 0.193 |
| Water vs Fe-tartrate | 0.342 | 0.382 | 0.523 | 0.071 |
| Water vs Fe-citrate | 0.010 | 0.274 | 0.329 | 0.669 |

[1] four pens per treatment; four pigs per pen (two males and two females); one male pig was sampled for this parameter, and the same pig was sampled throughout In summary, piglets tend to get very stressed when they are weaned, and can easily become infected during the two week period that follows weaning. This results in a decrease in performance. As the results demonstrate, piglets that were administered the water soluble iron (III) complexes had improved feed conversion rates (lower numbers) for the period 7 to 14 days when compared to the control group receiving only water. It is believed that this is a result of inhibiting proliferation of *E. coli* infection which shows up in the second week after weaning. These results are consistent with the poultry data in Example 1 where lower levels of *E. coli* are measured upon treatment with ferric quinate and tyrosinate.

Example 8: Inhibition of BioFilm by Iron Complex Compounds—Results Ferric EDTA, Ferric Malate and Ferric Oxalate Hydroxylate Titrations in Clinical Strains from CF Lung Isolate No. 11 from SED Strains'

Materials and Methods

Iron Complex Compounds: Ferric EDTA, Ferric Malate and Ferric Oxalate Hydroxylate were tested using clinical strains from CF Lung Isolate No. 11 from SED Strains.

Sterile beads were placed into 3 ml of Dulbecco's Modified Eagle Medium (DMEM), alongside the desired concentration of the iron-complex and inoculated with PAO SED #11 to $OD_{600}$ of 0.05. The beads were then incubated at 37° C. for 24 hours.

The beads were gently washed three times in PBS, placed into 1 ml of PBS and water bath sonicated for 12 minutes. Biofilm on each bead was quantitated by counting colony forming units. The PBS containing biofilm bacterial cells was serially diluted and 10 µl of each dilution was spotted onto LB Agar. These plates were incubated at 30° C. for 24 hours and the colonies were counted.

Figure 10:
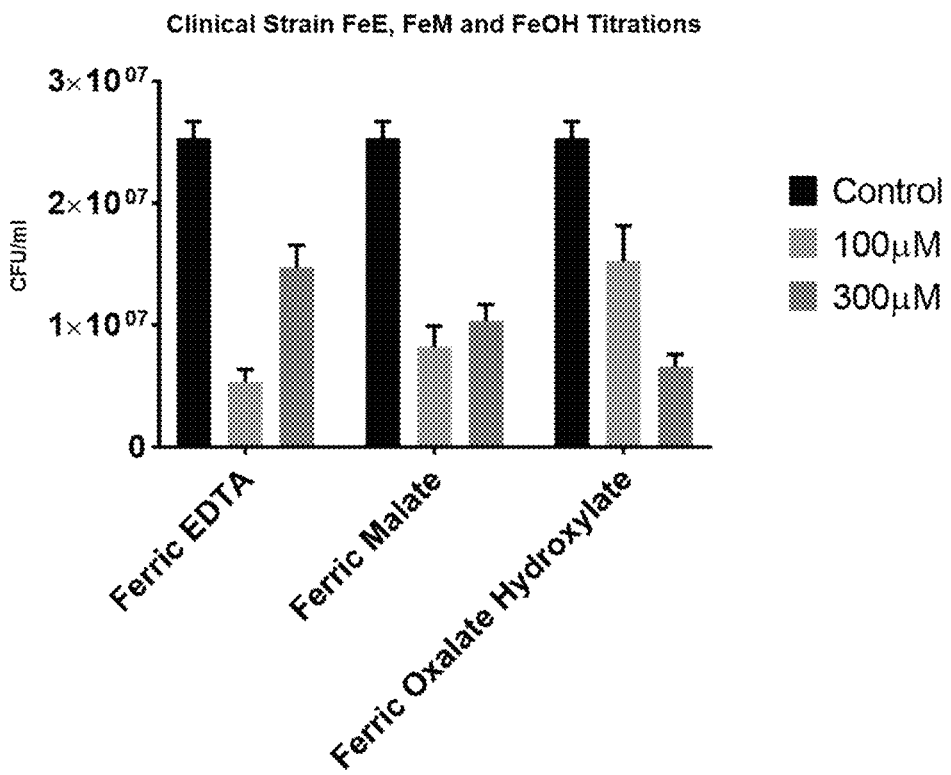
FIG. 10 is a bar graph showing the average number of colony forming units perml (cfu/ml) of CF Lung Isolate No. 11 from SED Strains versus no, 100 and 300 µg treated with Ferric EDTA, Ferric Malate and Ferric Oxalate.

The results are shown in FIG. 10. All Fe compounds tested displayed statistically significant inhibition of biofilms formed of clinical isolates.

Example 9. Efficacy of Ferric Lactate and FeQ (Q-PLEX) to Reduce *Campylobacter* Carriage in Chickens Materials and Methods A study was performed to evaluate reduction of *Campylobacter* carriage in chickens using ferric lactate in one treatment group, and FeQ (Q-PLEX) in a second treatment group. A third treatment group served as a positive control. The ferric lactate and FeQ were administered to the treatment groups at a concentration of 340 µM in the drinking water. Each treatment group comprised 12 birds per pen. All three treatment groups were orally challenged with 105 cfu of *Campylobacter jejuni* at day 14 of the trial. At day 35 all birds were euthanized, and quantitative bacteriology performed on caecal contents.

Results

Figure 11:
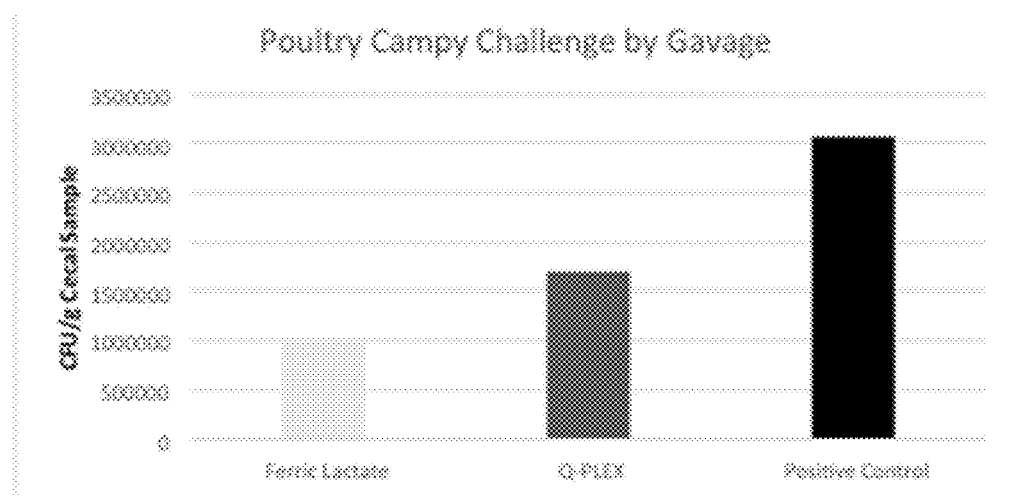
FIG. 11 is a bar graph showing the average number of *Campylobacter* colony forming units per gram (cfu/g) of caeca samples at day 35 for groups treated with Ferric.lactate, FeQ (Q-PLEX), and a positive control, of Example 9.

The results are shown in FIG. 11. Birds that were treated with ferric lactate and FeQ (Q-PLEX) in their drinking water had lower levels of *Campylobacter* in their caeca than birds in the positive control group with the lowest levels achieved using ferric lactate.

Example 10. Dose Ranging Study of FeTyr Administered in Feed to Reduce *Campylobacter* Carriage in Chickens and Promote Growth in Chickens As described above, FeTyr can be used to promote growth in chickens. This study demonstrates the most effective dosages in chickens to enhance weight gain.

Materials and Methods

A study was performed to evaluate growth promotion and reduction of *Campylobacter* carriage using FeTyr in Ross 308 male broilers with 7 treatment groups. Each treatment group comprised eight replicates of 10 birds per pen (80 birds/treatment group), with 2 control groups and 6 test groups. All the test groups and both of the control groups were exposed at day 20 of the trial to dirty litter, which tested positive for *Campylobacter*. This method was used to provide a more natural method to *Campylobacter* challenge the birds. Thus there were two positive controls where each treatment group was challenged with *Campylobacter*, and five treatment groups that were all challenged with *Campylobacter*. The total number of birds used in the 7 treatment groups was 560.

Details of the treatments are provided in Table 24. Treatment group 1 was a positive control where birds just received the commercial feed, and were challenged with dirty litter containing *Campylobacter* at day 20. Treatment group 2 received 0.01 g/kg of TYPLEX (FeTyr) in their feed, and were challenged with dirty litter containing *Campylobacter* at day 20. Treatment group 3 received 0.02 g/kg of TYPLEX (FeTyr) in their feed, and was challenged with dirty litter containing *Campylobacter* at day 20. Treatment group 4 received 0.05 g/kg of TYPLEX (FeTyr) in their feed, and was challenged with dirty litter containing *Campylobacter* at day 20. Treatment group 5 received 0.1 g/kg of TYPLEX (FeTyr) in their feed, and was challenged with dirty litter containing *Campylobacter* at day 20. Treatment group 6 received 0.2 g/kg of TYPLEX (FeTyr) in their feed, and was challenged with dirty litter containing *Campylobacter* at day 20. Treatment group 7 was a second control group and received 0.022 g/kg FeQ in their feed, and was challenged with dirty litter containing *Campylobacter* at day 20. The birds were fed with a commercial three-phase feeding program using starter, grower and finisher feeds as described in Example 1. The birds were reared in floor pens to day 42, and fed starter, grower and finisher feed at day 0 to 11, 11 to 24, and 24 to 42 days, respectively. All birds were weighed individually and feed weigh backs recorded per pen at day 0, 11, 21, 24 and 42 days.

At day 20, litter, which was naturally *Campylobacter*-contaminated, was tested to confirm the presence of *Campylobacter*, and then added (approximately 2 kg/pen) to the litter in all pens. At day 42, caecal samples were taken and tested for *Campylobacter*, *E. coli* and *Salmonella* enumeration.

In order to minimize risk of cross-contamination, standard industry biosecurity measures were used including: disinfecting boots, changing overshoes and gloves between pens/treatments, entering *Campylobacter* negative pens before entering *Campylobacter* positive pens, and leaving adjacent pens empty. Daily health, culls, and mortality were recorded. All bird weights were recorded at 0, 11, 21, 24, 33 and 42 days. Weight gains, feed intake and feed conversion ratio (FCR) were derived for each feeding period.

Results

The growth results are summarized in Tables 24 to 34 and show the effects on the treatment groups of FeTyr at five different doses (T2-T6) in feed compared to the control group (treatment group 1, T1) and the FeQ control group (treatment group 7, T7) for the periods 0-11 days, 11-20 days, 20-25 days, 25-35 days, 11-25 days, 25-42 days, 35-42 days, 0-25 days, 0-35 days and 0-42 days.

TABLE 24

Zootechnical performance from 1 to 11 days of age (d)

| Treatment | ABW kg 1 d | ABW kg 11 d | AWG kg 1 to 11 d | AFI kg | MFCR feed:gain |
|---|---|---|---|---|---|
| T1 Control | 0.039 | 0.338$^{ab}$ | 0.299$^{ab}$ | 0.353$^{ab}$ | 1.179$^{xy}$ |
| T2 0.01 g TYPLEX ™/kg feed | 0.040 | 0.337$^{ab}$ | 0.297$^{ab}$ | 0.347$^{ab}$ | 1.225$^{y}$ |
| T3 0.02 g TYPLEX ™/kg feed | 0.040 | 0.345$^{b}$ | 0.305$^{b}$ | 0.353$^{ab}$ | 1.202$^{xy}$ |
| T4 0.05 g TYPLEX ™/kg feed | 0.040 | 0.326$^{a}$ | 0.286$^{a}$ | 0.338$^{a}$ | 1.180$^{xy}$ |
| T5 0.10 g TYPLEX ™/kg feed | 0.039 | 0.336$^{ab}$ | 0.296$^{ab}$ | 0.348$^{ab}$ | 1.174$^{xy}$ |
| T6 0.20 g TYPLEX ™/kg feed | 0.040 | 0.337$^{ab}$ | 0.297$^{ab}$ | 0.345$^{ab}$ | 1.185$^{xy}$ |
| T7 0.22 g Q-PLEX/kg feed | 0.040 | 0.350$^{b}$ | 0.310$^{b}$ | 0.357$^{b}$ | 1.150$^{x}$ |
| SED | 0.000 | 0.006 | 0.006 | 0.006 | 0.023 |
| P (probability) | 0.154 | 0.009 | 0.007 | 0.035 | 0.088 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Different superscript within a column indicates significant differences (a-b P ≤ 0.05; x-y 0.05 < P ≤ 0.1).

TABLE 25

Zootechnical performance from 11 to 20 days of age (d)

| Treatment | ABW kg 20 d | AWG kg | AFI kg 11 to 20 d | MFCR feed:gain |
|---|---|---|---|---|
| T1 Control | 0.931 | 0.593 | 0.846$^{ab}$ | 1.429$^{b}$ |
| T2 0.01 g TYPLEX ™/kg feed | 0.963 | 0.626 | 0.856$^{b}$ | 1.367$^{ab}$ |
| T3 0.02 g TYPLEX ™/kg feed | 0.972 | 0.628 | 0.848$^{ab}$ | 1.352$^{ab}$ |
| T4 0.05 g TYPLEX ™/kg feed | 0.944 | 0.618 | 0.790$^{a}$ | 1.300$^{a}$ |
| T5 0.10 g TYPLEX ™/kg feed | 0.963 | 0.627 | 0.845$^{ab}$ | 1.347$^{ab}$ |
| T6 0.20 g TYPLEX ™/kg feed | 0.959 | 0.622 | 0.851$^{ab}$ | 1.367$^{ab}$ |
| T7 0.22 g Q-PLEX/kg feed | 0.968 | 0.618 | 0.836$^{ab}$ | 1.357$^{ab}$ |
| SED | 0.021 | 0.035 | 0.020 | 0.035 |
| P (probability) | 0.462 | 0.456 | 0.042 | 0.042 |

Notes:
no pen replicates = 8; Birds/replicate pen = 10; 80 birds/treatment; SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different (P ≤ 0.05)

TABLE 26

Zootechnical performance from 11 to 25 days of age (d)

| Treatment | ABW kg 25 d | AWG kg | AFI kg 11 to 25 d | MFCR feed:gain |
|---|---|---|---|---|
| T1 Control | 1.388$^{a}$ | 1.050$^{a}$ | 1.578 | 1.511$^{b}$ |
| T2 0.01 g TYPLEX ™/kg feed | 1.450$^{bc}$ | 1.113$^{b}$ | 1.570 | 1.411$^{a}$ |
| T3 0.02 g TYPLEX ™/kg feed | 1.449$^{bc}$ | 1.105$^{ab}$ | 1.580 | 1.431$^{a}$ |
| T4 0.05 g TYPLEX ™/kg feed | 1.400$^{ab}$ | 1.074$^{ab}$ | 1.512 | 1.414$^{a}$ |
| T5 0.10 g TYPLEX ™/kg feed | 1.458$^{c}$ | 1.122$^{b}$ | 1.560 | 1.391$^{a}$ |
| T6 0.20g TYPLEX ™/kg feed | 1.444$^{bc}$ | 1.107$^{ab}$ | 1.566 | 1.415$^{a}$ |
| T7 0.22 g Q-PLEX/kg feed | 1.463$^{c}$ | 1.113$^{b}$ | 1.541 | 1.387$^{a}$ |
| SED | 0.025 | 0.020 | 0.030 | 0.025 |
| P (probability) | 0.021 | 0.010 | 0.279 | <0.001 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different (P ≤ 0.05)

TABLE 27

Zootechnical performance from 20-25 days of age (d)

| Treatment | AWG/bird/period kg | AFI/bird/period kg 20-25 d | MFCR feed:gain |
|---|---|---|---|
| T1 Control | 0.457 | 0.732 | 1.617$^{bc}$ |
| T2 0.01 g TYPLEX ™/kg feed | 0.487 | 0.714 | 1.467$^{ab}$ |
| T3 0.02 g TYPLEX ™/kg feed | 0.477 | 0.732 | 1.537$^{abc}$ |
| T4 0.05 g TYPLEX ™/kg feed | 0.456 | 0.723 | 1.64F |
| T5 0.10 g TYPLEX ™/kg feed | 0.495 | 0.715 | 1.446$^{a}$ |
| T6 0.20 g TYPLEX ™/kg feed | 0.484 | 0.715 | 1.479$^{abc}$ |
| T7 0.22 g Q-PLEX/kg feed | 0.495 | 0.705 | 1.430$^{a}$ |
| SED | 0.018 | 0.017 | 0.076 |
| P (probability) | 0.177 | 0.677 | 0.039 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different (P ≤ 0.05)

TABLE 28

Zootechnical performance from 25-35 days of age (d)

| Treatment | AWG/bird/period kg | AFI/bird/period kg 25-35 d | MFCR feed:gain |
|---|---|---|---|
| T1 Control | 1.183$^{a}$ | 1.960 | 1.659$^{b}$ |
| T2 0.01 g TYPLEX ™/kg feed | 1.267$^{bc}$ | 1.962 | 1.556$^{a}$ |
| T3 0.02 g TYPLEX ™/kg feed | 1.218$^{abc}$ | 1.914 | 1.571$^{a}$ |
| T4 0.05 g TYPLEX ™/kg feed | 1.206$^{ab}$ | 1.897 | 1.572$^{a}$ |

TABLE 28-continued

Zootechnical performance from 25-35 days of age (d)

| Treatment | AWG/bird/period kg | AFI/bird/period kg 25-35 d | MFCR feed:gain |
|---|---|---|---|
| T5 0.10 g TYPLEX ™/kg feed | 1.245[abc] | 1.911 | 1.579[a] |
| T6 0.20 g TYPLEX ™/kg feed | 1.281[c] | 1.974 | 1.546[a] |
| T7 0.22g Q-PLEX/kg feed | 1.236[abc] | 1.917 | 1.607[ab] |
| SED | 0.032 | 0.040 | 0.030 |
| P (probability) | 0.050 | 0.319 | 0.010 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different ($P \leq 0.05$)

TABLE 29

Zootechnical performance from 20-35 days of age (d)

| Treatment | ABW kg 35 d | AWG kg | AFI kg 20 to 35 d | MFCR feed:gain |
|---|---|---|---|---|
| T1 Control | 2.571[a] | 1.640[a] | 2.692 | 1.645[b] |
| T2 0.01 g TYPLEX ™/kg feed | 2.717[b] | 1.754[ab] | 2.676 | 1.531[a] |
| T3 0.02 g TYPLEX ™/kg feed | 2.668[ab] | 1.696[ab] | 2.646 | 1.561[ab] |
| T4 0.05 g TYPLEX ™/kg feed | 2.607[ab] | 1.663[ab] | 2.619 | 1.579[ab] |
| T5 0.10 g TYPLEX ™/kg feed | 2.703[ab] | 1.740[ab] | 2.625 | 1.540[a] |
| T6 0.20 g TYPLEX ™/kg feed | 2.725[b] | 1.766[b] | 2.688 | 1.527[a] |
| T7 0.22 g Q-PLEX/kg feed | 2.698[ab] | 1.730[ab] | 2.622 | 1.554[a] |
| SED | 0.047 | 0.040 | 0.087 | 0.028 |
| P (probability) | 0.011 | 0.021 | 0.372 | 0.002 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different ($P \leq 0.05$)

TABLE 30

Zootechnical performance from 25-42 days of age (d)

| Treatment | ABW kg 28 d | ABW kg 30 d | ABW kg 42 d | AWG kg | AFI kg 25-42 d | MFCR feed:gain |
|---|---|---|---|---|---|---|
| T1 Control | 1.746[a] | 1.921[a] | 3.344[a] | 1.956[a] | 3.427 | 1.781[b] |
| T2 0.01 g TYPLEX ™/kg feed | 1.837[b] | 2.014[ab] | 3.482[ab] | 2.032[ab] | 3.378 | 1.681[a] |
| T3 0.02 g TYPLEX ™/kg feed | 1.828[b] | 1.996[ab] | 3.465[ab] | 2.015[ab] | 3.373 | 1.675[a] |
| T4 0.05 g TYPLEX ™/kg feed | 1.773[ab] | 1.943[ab] | 3.398[ab] | 1.998[ab] | 3.355 | 1.682[a] |
| T5 0.10 g TYPLEX ™/kg feed | 1.835[b] | 2.023[b] | 3.530[b] | 2.072[ab] | 3.440 | 1.686[a] |
| T6 0.20 g TYPLEX ™/kg feed | 1.837[b] | 2.023[b] | 3.532[b] | 2.088[b] | 3.433 | 1.656[a] |
| T7 0.22 g Q-PLEX/kg feed | 1.836[b] | 2.031[b] | 3.488[ab] | 2.026[ab] | 3.381 | 1.703[ab] |
| SED | 0.032 | 0.032 | 0.051 | 0.039 | 0.064 | 0.026 |
| P (probability) | 0.025 | 0.006 | 0.006 | 0.030 | 0.752 | <0.001 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different ($P \leq 0.05$)

TABLE 31

Zootechnical performance from 35-42 days of age (d)

| Treatment | AWG Kg | AFI kg 35 to 42 d | MFCR feed:gain |
|---|---|---|---|
| T1 Control | 0.773 | 1.467 | 2.001 |
| T2 0.01 g TYPLEX ™/kg feed | 0.765 | 1.415 | 1.953 |
| T3 0.02 g TYPLEX ™/kg feed | 0.797 | 1.459 | 1.833 |
| T4 0.05 g TYPLEX ™/kg feed | 0.792 | 1.458 | 1.853 |
| T5 0.10 g TYPLEX ™/kg feed | 0.827 | 1.529 | 1.852 |
| T6 0.20 g TYPLEX ™/kg feed | 0.807 | 1.460 | 1.839 |
| T7 0.22 g Q-PLEX/kg feed | 0.790 | 1.464 | 1.864 |
| SED | 0.027 | 0.047 | 0.093 |
| P (probability) | 0.328 | 0.424 | 0.454 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different ($P \leq 0.05$)

TABLE 32

Zootechnical performance from 0-25 days of age (d)

| Treatment | AWG kg | AFI kg 0-25 d | MFCR feed:gain |
|---|---|---|---|
| T1 Control | 1.349[a] | 1.931 | 1.436[b] |
| T2 0.01 g TYPLEX ™/kg feed | 1.410[bc] | 1.918 | 1.360[a] |
| T3 0.02 g TYPLEX ™/kg feed | 1.410[bc] | 1.933 | 1.373[a] |
| T4 0.05 g TYPLEX ™/kg feed | 1.360[ab] | 1.850 | 1.362[a] |
| T5 0.10 g TYPLEX ™/kg feed | 1.418[c] | 1.908 | 1.345[a] |

TABLE 32-continued

Zootechnical performance from 0-25 days of age (d)

| Treatment | AWG kg | AFI kg 0-25 d | MFCR feed:gain |
|---|---|---|---|
| T6 0.20 g TYPLEX ™/kg feed | 1.404$^{bc}$ | 1.911 | 1.364$^a$ |
| T7 0.22 g Q-PLEX/kg feed | 1.422$^c$ | 1.898 | 1.335$^a$ |
| SED | 0.025 | 0.033 | 0.020 |
| P (probability) | 0.021 | 0.207 | <0.001 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different (P ≤ 0.05)

TABLE 33

Zootechnical performance from 0-35 days of age (d)

| Treatment | AWG/bird/period kg | AFI/bird/period kg 0-35 d | MFCR feed:gain |
|---|---|---|---|
| T1 Control | 0.651 | 3.891 | 1.538$^b$ |
| T2 0.01 g TYPLEX ™/kg feed | 0.704 | 3.880 | 1.451$^a$ |
| T3 0.02 g TYPLEX ™/kg feed | 0.672 | 3.847 | 1.465a |
| T4 0.05 g TYPLEX ™/kg feed | 0.664 | 3.747 | 1.460a |
| T5 0.10 g TYPLEX ™/kg feed | 0.680 | 3.819 | 1.452$^a$ |
| T6 0.20 g TYPLEX ™/kg feed | 0.702 | 3.885 | 1.450$^a$ |
| T7 0.22 g Q-PLEX/kg feed | 0.668 | 3.815 | 1.458$^a$ |
| SED | 0.024 | 0.061 | 0.019 |
| P (probability) | 0.252 | 0.218 | <0.001 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different (P ≤ 0.05)

TABLE 34

Zootechnical performance from 0-42 days of age (d)

| Treatment | AWG/bird/period kg | AFI/bird/period kg 0-42 d | MFCR feed:gain |
|---|---|---|---|
| T1 Control | 3.305$^a$ | 5.358 | 1.637$^b$ |
| T2 0.01 g TYPLEX ™/kg feed | 3.442$^{ab}$ | 5.295 | 1.546$^a$ |
| T3 0.02 g TYPLEX ™/kg feed | 3.425$^{ab}$ | 5.306 | 1.550$^a$ |
| T4 0.05 g TYPLEX ™/kg feed | 3.358$^{ab}$ | 5.205 | 1.550$^a$ |
| T5 0.10 g TYPLEX ™/kg feed | 3.490$^b$ | 5.348 | 1.543$^a$ |
| T6 0.20 g TYPLEX ™/kg feed | 3.492$^b$ | 5.345 | 1.536$^a$ |
| T7 0.22 g Q-PLEX/kg feed | 3.448$^{ab}$ | 5.279 | 1.547$^a$ |
| SED | 0.051 | 0.081 | 0.018 |
| P (probability) | 0.006 | 0.524 | <0.001 |

Notes:
no pen replicates = 8; Birds/replicate pen = 10; 80 birds/treatment;
SED = Standard error of deviation
ABW = average body weight/pen;
AWG = mean weight gain/pen;
AFI = mean feed intake/pen;
MFCR = total feed intake per pen/(total live weight of pen + total weight of dead birds in pen) − total live weight of pen at start of period.
Values in same column with no common superscript are significantly different (P ≤ 0.05)

Figure 12:
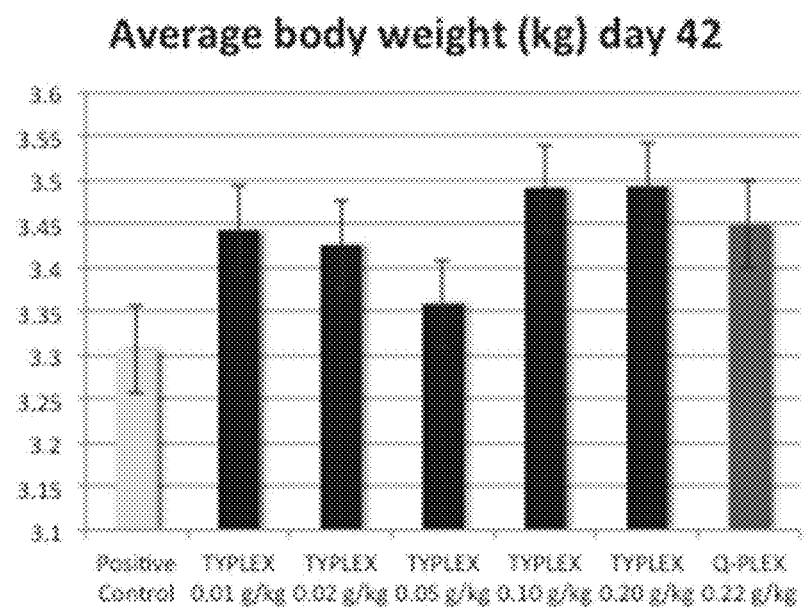
FIG. 12 is a bar graph showing the average body weight at day 42 for all treatment groups described in Example 9.

FIG. 12 shows the average body weight at day 42 for all treatment groups. The figure shows that all treatment groups receiving FeTyr (TYPLEX) and FeQ (Q-PLEX) had higher average body weight at day 42 than the control group.

Figure 13:
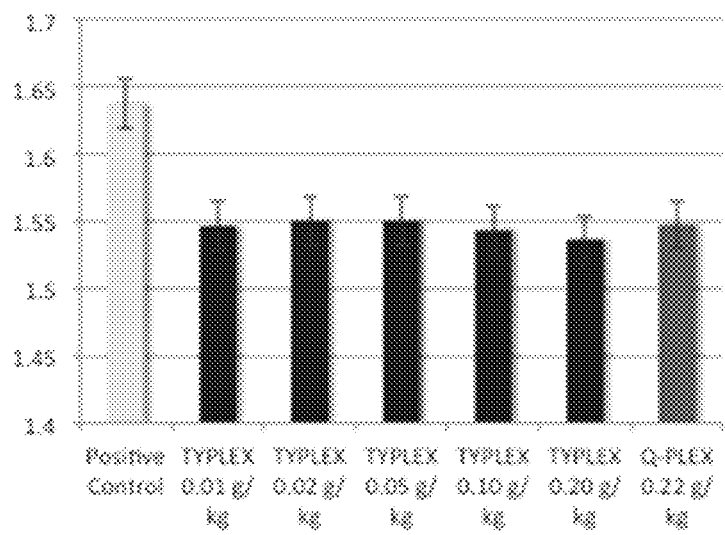
FIG. 13 is a graph showing the mortality adjusted feed conversion rate (MFCR) at day 42 for all treatment groups described in Example 9.

FIG. 13 shows the mortality adjusted feed conversion rate (MFCR) at day 42 for all treatment groups. (A lower MFCR number is a better result.) The figure shows that all treatment groups receiving FeTyr (TYPLEX) and FeQ (Q-PLEX) had improved MFCR values compared to the control group.

Figure 14:
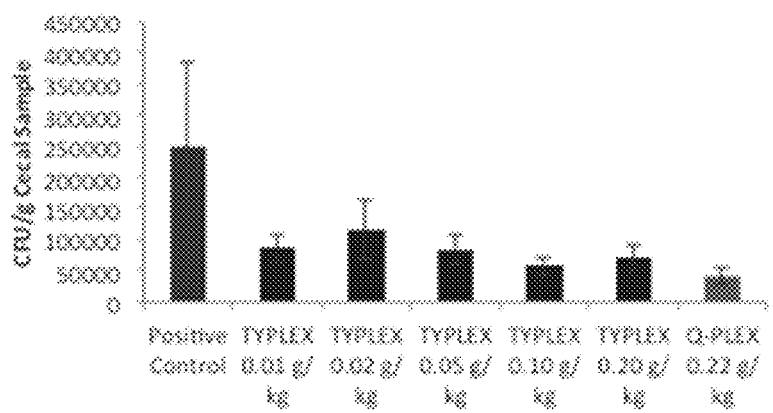
FIG. 14 is a graph showing the number of *Campylobacter* colony forming units per gram (cfu/g) of caeca at day 42 for all treatment groups described in Example 9.

FIG. 14 shows the number of *Campylobacter* colony forming units per gram (cfu/g) of caeca at day 42 for all treatment groups. (A lower number is a better result.) The results show that feeding FeTyr (TYPLEX) or FeQ (Q-PLEX) in feed had a positive effect on reducing *Campylobacter* infection of poultry.

Figure 15:
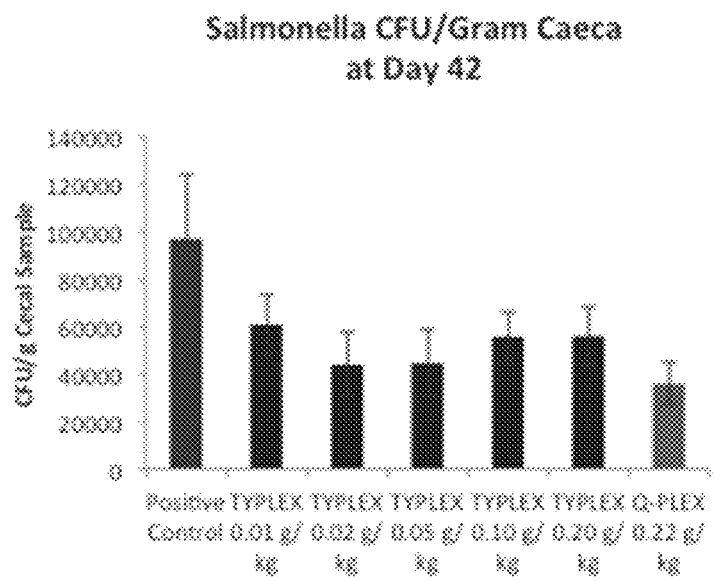
FIG. 15 is a graph showing the number of *Salmonella* colony forming units per gram (cfu/g) of caeca at day 42 for all treatment groups in Example 9.

FIG. 15 shows the number of *Salmonella* colony forming units per gram (cfu/g) of caeca at day 42 for all treatment groups. (A lower number is a better result.) The results show that feeding FeTyr (TYPLEX) or FeQ (Q-PLEX) in feed had a positive effect on reducing *Campylobacter* infection of poultry.

Figure 16:
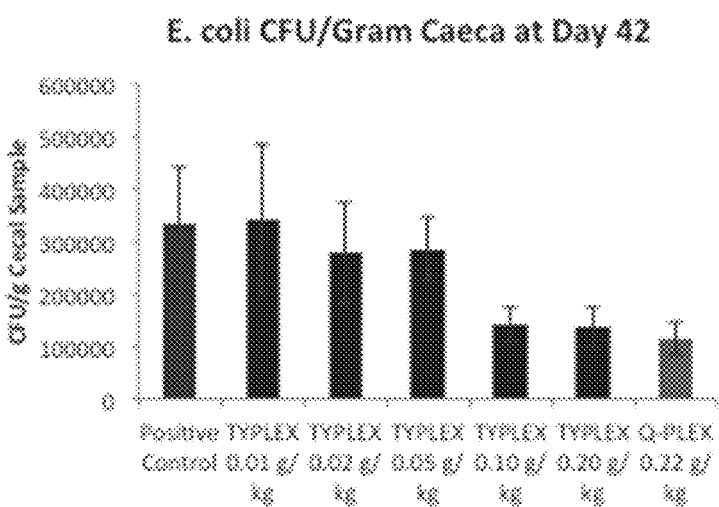
FIG. 16 is a graph showing the number of *E. coli* colony forming units per gram (cfu/g) of caeca at day 42 for all treatment groups described in Example 9.

FIG. 16 shows the number of *E. coli* colony forming units per gram (cfu/g) of caeca at day 42 for all treatment groups. (A lower number is a better result.) The results show that feeding FeTyr (TYPLEX) or FeQ (Q-PLEX) in feed had a positive effect on reducing *Campylobacter* infection of poultry.

Example 11. Zootechnical Efficacy of Ferric Citrate in Rearing Calves

Materials and Methods

A study was performed to evaluate the potential of ferric citrate (CI-PLEX™ CHELATE) to improve calf health, welfare, and performance. A total of 80 rearing calves (German Holstein) were used from d 12 to d 68 of age. 40 calves were fed a basal milk replacer (T1 Control). For comparison, 40 calves were fed the basal milk replacer with addition of ferric (III) citrate (T2 CI-PLEX™ CHELATE, 500 g/tonne feed) with a microtracer present at a rate of 10%, equivalent to 50 g/tonne for product identification purposes only. The basal milk replacer was supplemented with ferrous (II) sulfate at normal commercial rates (supplying 85 g Fe/tonne feed). T2 was also supplemented with normal commercial practice of Fe (ferrous (II) sulfate at 85 g Fe/tonne feed) with Fe at 85 g/tonne feed from the ferric (III) citrate (CI-PLEX™ CHELATE). No diet exceeded the maximum EU permitted Fe for rearing calf feeds. The treatments are summarized in Table 35. The basal milk replacer batch was produced, and then split into 2 aliquots prior to adding the different inorganic or organic Fe sources to T1, and T2 diets. Calves were housed in rearing units, each unit with pens on either side of a central aisle.

TABLE 35

Study treatments, Fe content in the milk replacer

| Treatment | Basal feed + Fe products | Fe product g/tonne feed | Target added Fe g/tonne feed |
|---|---|---|---|
| T1* | Control (basal milk replacer containing Ferrous(II) sulfate, ca. 32% Fe) | 266 g FeSO$_4$ | 85 |
| T2** | CI-PLEX ™ CHELATE (basal milk replacer containing Ferrous(II) sulfate + microtraced CI-PLEX ™ CHELATE) | 550 g microtraced ferric citrate + 255 g FeSO$_4$ | 170 |
| 2 treatments | 40 pens × 1 calve/pen per treatment[1] | | |

The following parameters were measured: mean pen body weight (BW), feed intake (FI), body weight gain (BWG), feed conversion ratio (FCR, feed:gain) at study start and on days 7, 14, 21, 28, 35, 42, 49 and 56 days on trial. In addition, the following were also recorded: body temperature, faeces quality, coughing score, and nasal discharge.

The composition of the basal calf milk replacer is shown in Table 36, and the feeding schedule in Table 37.

TABLE 36

Composition of basal calf milk replacer

| | | Basal milk replacer |
|---|---|---|
| Feed ingredients: | | |
| Skimmed milk | % | 34.0 |
| Dried whey | % | 28.1 |
| Plant fat | % | 17.0 |
| Soya protein, hydrolysed | % | 9.0 |
| Dried whey, delactated | % | 7.0 |
| Wheat meal, hydrolysed | % | 2.5 |
| Premix* | % | 2.2 |
| L-Lysine | % | 0.2 |
| Nutritional composition: | | |
| Metabolisable Energy | MJ/kg | 18.70 |
| Crude protein | g/kg | 220.00 |
| Lysine | g/kg | 18.00 |
| Crude fat | g/kg | 180.00 |
| Crude ash | g/kg | 80.00 |
| Crude fibre | g/kg | 2.00 |
| Calcium | g/kg | 9.00 |
| Phosphorus | g/kg | 7.00 |
| Sodium | g/kg | 5.00 |

[1]Contents per kg premix: 400,000 I.U. vit. A (acetate); 120,000 I.U. vit. D$_3$; 8,000 mg vit. E (α-tocopherol acetate); 200 mg vit. K$_3$ (MSB); 250 mg vit. B$_1$ (mononitrate); 420 mg vit. B$_2$ (cryst. riboflavin); 2,500 mg niacin (niacinamide); 400 mg Vit. B$_6$ (HCl); 2,000 μg vit. B$_{12}$; 25,000 μg Biotin (commercial, feed grade); 1,000 mg pantothenic acid (Ca d-pantothenate); 100 mg folic acid (cryst. commercial feed grade); 4,000 mg Zn (sulfate); 6,000 mg Mn (sulfate); 800 mg Cu (sulfate-pentahydrate); 15 mg Se (Na-selenite); 45 mg I (Ca-iodate); 130 g Na (NaCl); 55 g Mg (sulfate).

TABLE 37

Feeding schedule for calf milk replacer

| Day on trial | Milk replacer (l/feed time) 07:00 | Milk replacer (l/feed time) 17:00 | Milk replacer (l/day) | Milk replacer (powder) (g/day) |
|---|---|---|---|---|
| 01-04 | 2.00 | 2.00 | 4.0 | 500 |
| 05-07 | 2.25 | 2.25 | 4.5 | 560 |

TABLE 37-continued

Feeding schedule for calf milk replacer

| Day on trial | Milk replacer (l/feed time) 07:00 | Milk replacer (l/feed time) 17:00 | Milk replacer (l/day) | Milk replacer (powder) (g/day) |
|---|---|---|---|---|
| 08-10 | 2.50 | 2.50 | 5.0 | 625 |
| 11-14 | 2.75 | 2.75 | 5.5 | 690 |
| 15-18 | 3.00 | 3.00 | 6.0 | 750 |
| 19-21 | 3.00 | 3.00 | 6.0 | 750 |
| 22-28 | 3.00 | 3.00 | 6.0 | 750 |
| 29-35 | 3.00 | 3.00 | 6.0 | 750 |
| 36-42 | 2.50 | 2.50 | 5.0 | 625 |
| 43-49 | 2.00 | 2.00 | 4.0 | 500 |
| 50-56 | 2.00 | 2.00 | 2.0 | 250 |

The milk replacer was dissolved in warm water at around 50° C. The concentration was 125 grams per liter. The drinking temperature was kept at 38 to 40° C.

Additionally, a commercial calf starter feed (mash) without phytogenics, probiotics, organic acids or enzymes was provided. The ingredient composition of the calf starter feed is shown in Table 38. The daily allocated amounts of this feed are shown in Table 39. Straw was also provided in pre-weighed amounts throughout the 56 day feeding period.

TABLE 38

Ingredient and nutritional composition of calf starter feed

| Feed ingredients: | | |
|---|---|---|
| Wheat | % | 30.00 |
| Corn | % | 28.40 |
| Soybean meal | % | 23.00 |
| Sugar beet pulp | % | 10.00 |
| Wheat semolina | % | 3.00 |
| Soybean hulls | % | 2.00 |
| Calcium carbonate | % | 1.30 |
| Monocalcium phosphate | % | 0.60 |
| Sodium chloride | % | 0.40 |
| Premix* | % | 1.30 |
| Proximate composition: | | |
| Metabolisable energy | MJ/kg | 10.80 |
| Crude protein | g/kg | 170.00 |
| Crude fat | g/kg | 30.00 |
| Crude ash | g/kg | 66.00 |
| Crude fibre | g/kg | 70.00 |
| Calcium | g/kg | 10.00 |
| Phosphorus | g/kg | 5.00 |
| Sodium | g/kg | 4.00 |

*Content per kg calf starter feed: 13500 IU vit. A; 2700 IU vit. D$_3$; 135 mg vit, E;. 135 Zn (zinc oxide); 45 mg Fe (iron (II) sulfate); 45 mg Mn(manganese (II) oxide); 23 mg Cu (copper (II) sulfate-pentahydrate); 1.8 mg I (calcium Iodate; 0.36 mg Se (sodium selenite).

TABLE 39

Feeding schedule for calf starter during the 56 day feeding period

| Day of the feeding trial | Calf starter feed (g/day as is) |
|---|---|
| 01-04 | 100 |
| 05-07 | 200 |
| 08-10 | 200 |
| 11-14 | 300 |
| 15-18 | 500 |
| 19-21 | 700 |
| 22-28 | 900 |
| 29-35 | 1200 |
| 36-42 | 1500 |
| 43-49 | 1800 |
| 50-56 | 2000 |

Results

Key proximate analytical parameters (crude protein, crude fat, ash and moisture) are summarized in Table 40. The proximate analysis of the milk replacer, calf starter and straw were within acceptable tolerances.

TABLE 40

Key analyzed values of calf feeds

| Feed | Dry matter (%) | Crude protein (%)* | Crude fat (%) | Ash (%) | Fe (mg/kg) |
|---|---|---|---|---|---|
| Milk replacer ||||||
| T1 Fe (II) sulfate | 98.12 | 21.25 | 18.63 | 7.33 | 92.7 |
| T2 CI-PLEX ™ + Fe (II) sulfate | 97.96 | 21.22 | 18.59 | 7.36 | 189.6 |
| Calf starter ||||||
| T1 Fe (II) sulfate | 89.36 | 18.36 | 3.11 | 6.63 | 126.2 |
| T2 CI-PLEX ™ + Fe (II) sulfate ||||||
| Straw ||||||
| T1 Fe (II) sulfate | 86.80 | 3.64 | 1.23 | 5.51 | 211.4 |
| T2 CI-PLEX ™ + Fe (II) sulfate ||||||

Throughout the 56-day treatment period no calf died or had to be excluded from the study. The trial was run without any adverse technical events (e.g. power failure, feed/water failures, etc.). Four calves showed clinical signs of respiratory infection (n=1), claw injuries (n=2) and diarrhea (n=1), and were appropriately treated. The scoring of faecal consistency and of rectal temperature, coughing, nasal discharge as well as eye and ear scores were ranked daily. As a result of the excellent health status the overall scores were within the physiological range. Therefore, even partly significant, health relevant treatment effects were not evident (see Table 41.) The effects of ferric citrate supplementation are also shown in Table 41.

TABLE 41

Effect of ferric citrate on rearing calves

| Parameter | T1 Fe (II)sulfate | T2 Ferric Citrate (CI-PLEX ™ CHELATE) & Fe (II)sulfate | SEM | P |
|---|---|---|---|---|
| Mean age at start of rearing (d) | 12.2 ± 1.0 | 12.0 ± 0.8 | 0.106 | 0.348 |
| No replicate pens at rearing | 40 | 40 | | |
| No calves per pen at rearing | 1 | 1 | | |
| Mean BW at start of rearing (kg) | 51.4 ± 1.9 | 50.9 ± 1.9 | 0.217 | 0.251 |
| Mean BW at d 56 of rearing (kg) | 91.9 ± 2.0$^a$ | 94.3 ± 2.2$^b$ | 0.271 | <0.001 |
| ADG 1-21 d of rearing (g) | 268 ± 30$^a$ | 296 ± 21$^b$ | 3.293 | <0.001 |
| ADG 22-56 d of rearing (g) | 792 ± 48$^a$ | 837 ± 29$^b$ | 5.057 | <0.001 |
| ADG 1-56 d of rearing (g) | 723 ± 36$^a$ | 775 ± 23$^b$ | 4.445 | <0.001 |
| ADFI 1-21 d of rearing (g) | 804 ± 38 | 811 ± 34 | 4.043 | 0.435 |
| ADFI 22-56 d of rearing (kg) | 1.90 ± 0.02 | 1.90 ± 0.03 | 0.003 | 0.401 |
| ADFI 1-56 d of rearing (kg) | 1.49 ± 0.02 | 1.49 ± 0.02 | 0.002 | 0.273 |
| FCR 1-21 d of rearing (feed:gain) | 1.339 ± 0.142$^a$ | 1.215 ± 0.087$^b$ | 0.015 | <0.001 |
| FCR 22-56 d of rearing (feed:gain) | 2.408 ± 0.148$^a$ | 2.278 ± 0.086$^b$ | 0.015 | <0.001 |
| FCR 1-56 d of rearing (feed:gain) | 2.065 ± 0.100$^a$ | 1.931 ± 0.066$^b$ | 0.012 | <0.001 |
| Mean daily faecal score* 1-56 d of rearing | 0.68 ± 0.14 | 0.65 ± 0.24 | 0.022 | 0.467 |
| Mean daily body temperature score* 1-56 d of rearing | 0.09 ± 0.11$^a$ | 0.04 ± 0.10$^b$ | 0.012 | 0.035 |
| Mean daily coughing score* 1-56 d of rearing | 0.51 ± 0.13 | 0.48 ± 0.18 | 0.017 | 0.516 |
| Mean daily nasal discharge score* 1-56 d of rearing | 0.44 ± 0.12 | 0.40 ± 0.25 | 0.022 | 0.314 |
| Mean daily eye score* 1-56 d of rearing | 0.04 ± 0.07 | 0.04 ± 0.07 | 0.008 | 0.953 |
| Mean daily ear score* 1-56 d of rearing | 0.04 ± 0.07 | 0.03 ± 0.05 | 0.007 | 0.426 |
| No calves treated with antibiotics, 1-56 d of rearing | 3 | 1 | | |
| No calves excluded, 1-56 d of rearing | 1 | 0 | | |
| % excluded, 1-56 d of rearing | 0 | 0 | | |

Notes:
Values are means of 5 piglets/pen.
SEM = Standard Error of the Mean.
Different superscripts in same row are significant or trending (a/b: P ≤ 0.05; x/y 0.05 < P ≤ 0.10).
*Score 0: normal; 1: slightly disorder; 2: middle disorder; 3: severe disorder.

CONCLUSIONS

The results of this study demonstrate that ferric citrate (CI-PLEX™ Chelate) and Fe (II) sulfate added at 85 mg/kg each to the basal milk replacer from d 01 to d 56 on trial (12 to d 67 of age):
  Significantly enhanced body weight from d 1 to d 21 of rearing by 10.4% (P: <0.001) in comparison to calves fed Fe (II) sulfate added at 85 mg/kg feed,
  Significantly improved body weight from d 22 to d 56 of rearing by 5.7% (P: <0.001) in comparison to calves fed Fe (II) sulfate added at 85 mg/kg feed,
  Significantly increased body weight from d 1 to d 56 of rearing by 7.2% (P: <0.001) in comparison to calves fed Fe (II) sulfate added at 85 mg/kg feed,
  Significantly reduced feed conversion ratio from d 1 to d 21 of rearing by 9.3% (P: <0.001) in comparison to calves fed Fe (II) sulfate added at 85 mg/kg feed,
  Significantly diminished feed conversion ratio from d 22 to d 56 of rearing by 5.4% (P: <0.001) in comparison to calves fed Fe (II) sulfate added at 85 mg/kg feed,
  Significantly decreased feed conversion ratio from d 1 to d 56 of rearing by 6.5% (P: <0.001) in comparison to calves fed Fe (II) sulfate added at 85 mg/kg feed, Significantly improved scoring of body temperature from d 1 to d 56 of rearing in comparison to calves fed Fe (II) sulfate added at 85 mg/kg feed (0.04 vs. 0.09).

Slightly improved scoring of faecal consistency, coughing, and nasal discharge from d 1 to d 56 of rearing in comparison to calves fed Fe (II) sulfate added at 85 mg/kg feed.

Slightly reduced antibiotic treatments from d 1 to d 56 of rearing in comparison to calves fed Fe (II) sulfate added at 85 mg/kg feed.

In conclusion, the calf milk replacer efficacy study showed, that supplementation of the basal milk replacer with ferrous (II) sulfate at normal commercial rates (supplying 85 g Fe/tonne feed) with ferric citrate (CI-PLEX) at 85 mg/kg significantly improved the overall daily body weight gain during the 56-d rearing period (d 12 to d 67 of age). Regarding the two rearing phases (d 1 to d 21 on trial; d 22 to d 56 on trial) positive responses were also significant. Because of the significant benefits of adding ferric citrate (CI-PLEX™) as well as Fe (II) sulfate on body weight gain the corresponding feed conversion ratios were significantly decreased by 9.3% (d 1 to d 21 on trial), 5.4% (d 22 to d 56 on trial), and by 6.5% (d 1 to d 56 on trial), respectively. The results of scoring showed significant benefits on body temperature, and benefits on other parameters (scoring of faeces, coughing, nasal discharge). The findings demonstrate that the addition of ferric citrate (CI-PLEX™) to rearing bull calves from d 12 to d 67 of age (56-d rearing period) provides statistically relevant performance benefits.

We claim:

1. A milk replacer composition comprising one or more Fe III complex compounds of Formula I:

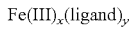

Fe(III)$_x$(ligand)$_y$      Formula I wherein x is an integer value of 1-2, y is an integer value of 1-3 and each ligand present is independently a conjugate base of an α-hydroxy acid selected from citric acid, tartaric acid, lactic acid, glycolic acid, quinic acid, glycolic acid, isoleucic acid, valic acid, malic acid, and mandelic acid; or each ligand is a conjugate base of an amino acid independently selected from the group consisting of, alanine, arginine, asparagine, aspartic acid, cysteine, glutamine, glutamic acid, histidine, isoleucine, leucine, lysine, methionine, phenylalanine, proline, serine, threonine, tryptophan, tyrosine, and valine; and salts and/or hydrates thereof; or a salt and/or hydrate thereof, and wherein at least one of the one or more Fe III complexes is in a concentrations ranging from 0.01 g/Kg of the milk replacer composition to 20 g/Kg of the milk replacer composition.

2. The composition of claim 1, wherein the one or more compounds having the structure of Formula I are selected from the group consisting of ferric lactate, ferric citrate, ferric and tartrate.

3. The composition of claim 1, wherein the milk replacer composition is for livestock or humans.

4. The composition of claim 3, wherein the livestock is selected from the group consisting of goat, sheep, cattle, rabbits, swine, camelids, bison, cat, deer, dog, donkey, gayal, rodents, horse, mule, reindeer, water buffalo, yak, and horses.

5. The composition of claim 1, wherein the milk replacer composition is a calf milk replacer.

6. The composition of claim 1, wherein when the ligand is a conjugate base of citric acid, the concentration of the compound ranges from 0.1 g/kg of the milk replacer composition to 5 g/kg of the milk replacer composition.

7. The composition of claim 1, further comprising ferrous sulfate.

8. The composition of claim 1, wherein the compound is in an effective amount to enhanced growth in mammals.

9. The composition of claim 8, wherein the enhanced growth is based on measurements of one or more characteristics selected from the group consisting of body weight, average body weight (ABW), feed intake or average feed intake (AFD), weight gain or average weight gain (AWG), and mortality adjusted feed conversion ratio (MFCR).

10. The composition of claim 1, wherein the composition is in the form of a liquid, gel, powder, tablet, capsule, solution, suspension, or syrup.

11. The composition of claim 1, wherein the concentration of the Fe III complex compound is present in a concentration between 0.1 g/Kg and 20 g/Kg of the milk replacer composition.

12. The composition of claim 1, wherein the concentration of the Fe III complex compound is present in a concentration between 0.1 g/Kg and 1 g/Kg of the milk replacer composition.

* * * * *

UNITED STATES PATENT AND TRADEMARK OFFICE
CERTIFICATE OF CORRECTION

PATENT NO. : 11,311,511 B2
APPLICATION NO. : 16/877190
DATED : April 26, 2022
INVENTOR(S) : Jafar Mahdavi, Dlawer Ala'Aldeen and Panos Soultanas It is certified that error appears in the above-identified patent and that said Letters Patent is hereby corrected as shown below:

In the Claims
Claim 1, Column 104, Line 4; replace "one or more Fe III complexes is in a concentrations" with --one or more Fe III complex compounds is in a concentration--
Claim 2, Column 104, Line 10; replace "ferric and tartrate." with --and ferric tartrate.--
Claim 8, Column 104, Line 27; replace "amount to enhanced growth" with --amount to enhance growth--

Signed and Sealed this
Twenty-third Day of August, 2022

Katherine Kelly Vidal
*Director of the United States Patent and Trademark Office*